United States Patent
Reddy et al.

(10) Patent No.: US 12,077,502 B2
(45) Date of Patent: *Sep. 3, 2024

(54) FORMULATIONS OF T-TYPE CALCIUM CHANNEL MODULATORS AND METHODS OF USE THEREOF

(71) Applicant: PRAXIS PRECISION MEDICINES, INC., Boston, MA (US)

(72) Inventors: Kiran Reddy, Boston, MA (US); Margaret S. Lee, Middleton, MA (US); Gabriel Maurice Belfort, Cambridge, MA (US); Sapna Makhija Garad, Malden, MA (US); Mahesh Padval, Cambridge, MA (US); Randall Wagner, Bend, OR (US); Marion Wittmann, Medford, MA (US)

(73) Assignee: Praxis Precision Medicines, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/871,065

(22) Filed: Jul. 22, 2022

(65) Prior Publication Data

US 2023/0192612 A1 Jun. 22, 2023

Related U.S. Application Data

(63) Continuation of application No. 17/387,648, filed on Jul. 28, 2021, now Pat. No. 11,427,540, which is a continuation of application No. PCT/US2020/041530, filed on Jul. 10, 2020.

(60) Provisional application No. 62/958,923, filed on Jan. 9, 2020, provisional application No. 62/934,820, filed on Nov. 13, 2019, provisional application No. 62/873,022, filed on Jul. 11, 2019.

(51) Int. Cl.
| | |
|---|---|
| *C07D 211/34* | (2006.01) |
| *A61K 9/00* | (2006.01) |
| *A61K 9/20* | (2006.01) |
| *A61K 9/48* | (2006.01) |
| *A61K 31/445* | (2006.01) |
| *A61K 47/38* | (2006.01) |
| *A61P 25/14* | (2006.01) |
| *C07D 211/26* | (2006.01) |

(52) U.S. Cl.
CPC .......... *C07D 211/34* (2013.01); *A61K 9/0053* (2013.01); *A61K 9/2009* (2013.01); *A61K 9/2013* (2013.01); *A61K 9/2018* (2013.01); *A61K 9/2054* (2013.01); *A61K 9/4825* (2013.01); *A61K 9/4858* (2013.01); *A61K 9/4866* (2013.01); *A61K 31/445* (2013.01); *A61K 47/38* (2013.01); *A61P 25/14* (2018.01); *C07D 211/26* (2013.01); *C07B 2200/13* (2013.01)

(58) Field of Classification Search
CPC .................................................... C07D 211/34
See application file for complete search history.

(56) References Cited

U.S. PATENT DOCUMENTS

| | | | |
|---|---|---|---|
| 3,845,770 | A | 11/1974 | Theeuwes et al. |
| 4,326,525 | A | 4/1982 | Swanson et al. |
| 4,902,514 | A | 2/1990 | Barclay et al. |
| 4,992,445 | A | 2/1991 | Lawter et al. |
| 5,001,139 | A | 3/1991 | Lawter et al. |
| 5,023,252 | A | 6/1991 | Hseih |
| 5,616,345 | A | 4/1997 | Geoghegan et al. |
| 5,624,677 | A | 4/1997 | El-Rashidy et al. |
| 5,852,014 | A | 12/1998 | Gaster et al. |
| 5,989,920 | A | 11/1999 | Gerald et al. |
| 6,544,997 | B1 | 4/2003 | Bosmans et al. |
| 6,984,637 | B2 | 1/2006 | Gong et al. |
| 7,067,665 | B2 | 6/2006 | Nazare et al. |
| 7,244,758 | B2 | 7/2007 | Pajouhesh et al. |
| 7,259,157 | B2 | 8/2007 | Liverton et al. |
| 7,319,098 | B2 | 1/2008 | Cho et al. |
| 7,507,760 | B2 | 3/2009 | Pajouhesh et al. |
| 8,377,968 | B2 | 2/2013 | Pajouhesh et al. |
| 8,569,344 | B2 | 10/2013 | Pajouhesh et al. |
| 9,096,522 | B2 | 8/2015 | Pajouhesh et al. |
| 11,427,540 | B2 * | 8/2022 | Reddy .................. A61K 31/445 |
| 11,649,207 | B2 | 5/2023 | Reddy et al. |

(Continued)

FOREIGN PATENT DOCUMENTS

| | | |
|---|---|---|
| CA | 2286870 A1 | 10/1998 |
| CN | 1252798 A | 5/2000 |

(Continued)

OTHER PUBLICATIONS

Astles et al., Diamine containing VLA-4 antagonists. Bioorg Med Chem. Aug. 2001;9(8):2195-202.

(Continued)

*Primary Examiner* — Nizal S Chandrakumar
(74) *Attorney, Agent, or Firm* — McCarter & English, LLP; Jonathan M. Sparks

(57) ABSTRACT

Described herein, in part, are dosage forms and compositions useful for preventing and/or treating a disease or condition relating to aberrant function of a T-type calcium channel, such as epilepsy and epilepsy syndromes (e.g., absence seizures, juvenile myoclonic epilepsy, or a genetic epilepsy), tremor (e.g., essential tremor), and psychiatric disorder (e.g., mood disorders (e.g., major depressive disorder)). The present invention further comprises methods for modulating the function of a T-type calcium channel.

35 Claims, 12 Drawing Sheets

(56) References Cited

U.S. PATENT DOCUMENTS

| | | |
|---|---|---|
| 2003/0086980 A1 | 5/2003 | Shin et al. |
| 2003/0087799 A1 | 5/2003 | Wolfart et al. |
| 2003/0125269 A1 | 7/2003 | Li |
| 2004/0197825 A1 | 10/2004 | Karicheti et al. |
| 2005/0245535 A1 | 11/2005 | Hangeland et al. |
| 2006/0003985 A1 | 1/2006 | Renger et al. |
| 2006/0025397 A1 | 2/2006 | Shin et al. |
| 2007/0010671 A1 | 1/2007 | Sekiguchi et al. |
| 2007/0037836 A1 | 2/2007 | Sekiguchi et al. |
| 2007/0129347 A1 | 6/2007 | Hinze et al. |
| 2008/0090863 A1 | 4/2008 | Sekiguchi et al. |
| 2008/0280900 A1 | 11/2008 | Pajouhesh et al. |
| 2009/0105249 A1 | 4/2009 | Benjamin et al. |
| 2009/0270413 A1 | 10/2009 | Galemmo, Jr. et al. |
| 2009/0298834 A1 | 12/2009 | Pajouhesh et al. |
| 2009/0298883 A1 | 12/2009 | Pajouhesh et al. |
| 2010/0004286 A2 | 1/2010 | Cho et al. |
| 2010/0056545 A1 | 3/2010 | Shin et al. |
| 2010/0094006 A1 | 4/2010 | Nam et al. |
| 2013/0065926 A1 | 3/2013 | Pajouhesh et al. |
| 2014/0011996 A1 | 1/2014 | Pajouhesh et al. |
| 2016/0175315 A1 | 6/2016 | Pajouhesh et al. |
| 2018/0312471 A1 | 11/2018 | Xie et al. |
| 2021/0128537 A1 | 5/2021 | Reddy et al. |
| 2022/0241258 A1 | 8/2022 | Reddy et al. |

FOREIGN PATENT DOCUMENTS

| | | |
|---|---|---|
| EP | 370498 A2 | 5/1990 |
| EP | 1464335 A2 | 10/2004 |
| EP | 1568695 A1 | 8/2005 |
| EP | 1757590 A1 | 2/2007 |
| FR | 2769914 A1 | 4/1999 |
| GB | 1003885 A | 9/1965 |
| JP | 2007-512350 A | 5/2007 |
| JP | 2016-516031 A | 6/2016 |
| JP | 2017-137299 A | 8/2017 |
| KR | 10-0754325 B1 | 9/2007 |
| KR | 10-0758317 B1 | 9/2007 |
| KR | 10-2009-0044924 A | 5/2009 |
| RU | 2007137266 A | 4/2009 |
| WO | WO-1993/004047 A1 | 3/1993 |
| WO | WO-1997/020823 A2 | 6/1997 |
| WO | WO-1997/046250 A1 | 12/1997 |
| WO | WO-2002/006245 A1 | 1/2002 |
| WO | WO-2003/007953 A1 | 1/2003 |
| WO | WO-2003/018563 A1 | 3/2003 |
| WO | WO-2003/086980 A1 | 10/2003 |
| WO | WO-2004/000311 A2 | 12/2003 |
| WO | WO-2004/035000 A2 | 4/2004 |
| WO | WO-2004/046110 A1 | 6/2004 |
| WO | WO-2005/007124 A2 | 1/2005 |
| WO | WO-2005/009392 A2 | 2/2005 |
| WO | 2005/051325 A2 | 6/2005 |
| WO | WO-2005/077082 A2 | 8/2005 |
| WO | WO-2005/086971 A2 | 9/2005 |
| WO | WO-2005/092882 A1 | 10/2005 |
| WO | WO-2005/095357 A2 | 10/2005 |
| WO | WO-2006/023881 A2 | 3/2006 |
| WO | WO-2006/023883 A2 | 3/2006 |
| WO | WO-2006/098969 A2 | 9/2006 |
| WO | WO-2006/104280 A1 | 10/2006 |
| WO | WO-2007/002361 A2 | 1/2007 |
| WO | WO-2007/002884 A2 | 1/2007 |
| WO | WO-2007/053819 A2 | 5/2007 |
| WO | WO-2007/073497 A2 | 6/2007 |
| WO | WO-2007/075852 A2 | 7/2007 |
| WO | WO-2007/077508 A2 | 7/2007 |
| WO | WO-2007/078990 A2 | 7/2007 |
| WO | WO-2007/120729 A2 | 10/2007 |
| WO | WO-2008/007835 A1 | 1/2008 |
| WO | WO-2008/018655 A1 | 2/2008 |
| WO | WO-2008/031227 A1 | 3/2008 |
| WO | WO-2008/033456 A1 | 3/2008 |
| WO | WO-2008/033460 A2 | 3/2008 |
| WO | WO-2008/033464 A2 | 3/2008 |
| WO | WO-2008/033465 A1 | 3/2008 |
| WO | WO-2008/050200 A1 | 5/2008 |
| WO | WO-2008/110008 A1 | 9/2008 |
| WO | WO-2008/117148 A1 | 10/2008 |
| WO | WO-2008/132679 A1 | 11/2008 |
| WO | WO-2009/009015 A1 | 1/2009 |
| WO | WO-2009/035307 A2 | 3/2009 |
| WO | WO-2009/054982 A1 | 4/2009 |
| WO | WO-2009/054983 A1 | 4/2009 |
| WO | WO-2009/054984 A1 | 4/2009 |
| WO | WO-2009/056934 A1 | 5/2009 |
| WO | WO-2009/130679 A1 | 10/2009 |
| WO | WO-2009/146539 A1 | 12/2009 |
| WO | WO-2009/146540 A1 | 12/2009 |
| WO | WO-2010/004857 A1 | 1/2010 |
| WO | WO-2010/046855 A1 | 4/2010 |
| WO | WO-2010/046869 A2 | 4/2010 |
| WO | WO-2010/083264 A1 | 7/2010 |
| WO | WO-2011/032291 A1 | 3/2011 |
| WO | 2012/088033 A2 | 6/2012 |
| WO | WO-2012/094615 A2 | 7/2012 |
| WO | 2014/149674 A1 | 9/2014 |
| WO | WO-2015/186056 A1 | 12/2015 |
| WO | WO-2016/041892 A1 | 3/2016 |
| WO | WO-2017/083867 A1 | 5/2017 |
| WO | WO-2018/109152 A1 | 6/2018 |
| WO | WO-2018/118101 A1 | 6/2018 |
| WO | WO-2019/094724 A1 | 5/2019 |
| WO | WO-2020/072773 A1 | 4/2020 |
| WO | WO-2021/007487 A1 | 1/2021 |
| WO | WO-2021/222342 A1 | 11/2021 |

OTHER PUBLICATIONS

Augustine et al., Calcium action in synaptic transmitter release. Annu Rev Neurosci. 1987;10:633-93.

Barton et al., The antihyperalgesic effects of the T-type calcium channel blockers ethosuximide, trimethadione, and mibefradil. Eur J Pharmacol. Oct. 3, 2005;521(1-3):79-85.

Barzegar-Jalali et al., Formulation and Evaluation of Sustained Release Dosage Form of Nifedipine Hydrochloride Using Hydrophilic Polymers. Journal of Reports in Pharmaceutical Sciences. 2013;2(1):32-37.

Berg et al., How well can epilepsy syndromes be identified at diagnosis? A reassessment 2 years after initial diagnosis. Epilepsia. Oct. 2000;41(10):1269-75.

Berge et al., Pharmaceutical salts. J Pharm Sci. Jan. 1977;66(1):1-19.

Bourinet et al., T-type calcium channels in neuropathic pain. Pain. Feb. 2016;157 Suppl 1:S15-S22.

Brittain et al., Effects of Pharmaceutical Processing on Drug Polymorphs and Solvates. Polymorphism in Pharmaceutical Solids. Drugs and the Pharmaceutical Sciences. Marcel Dekker, Inc., New York, Harry G. Brittain, (Ed.). Chapter 8, vol. 95, pp. 331-361, (1999).

Casillas-Espinosa et al., Z944, a Novel Selective T-Type Calcium Channel Antagonist Delays the Progression of Seizures in the Amygdala Kindling Model. PLoS One. Aug. 14, 2015;10(8):e0130012, 12 pages.

Catterall, Structure and regulation of voltage-gated Ca2+ channels. Annu Rev Cell Dev Biol. 2000;16:521-55.

Chaplan et al., Quantitative assessment of tactile allodynia in the rat paw. J Neurosci Methods. Jul. 1994;53(1):55-63.

Cheong et al., T-type Ca2+ channels in absence epilepsy. Pflugers Arch. Apr. 2014;466(4):719-34.

Clark et al., A virtual screening approach to finding novel and potent antagonists at the melanin-concentrating hormone 1 receptor. J Med Chem. Jul. 29, 2004;47(16):3962-71.

Coenen et al., Genetic animal models for absence epilepsy: a review of the WAG/Rij strain of rats. Behav Genet. Nov. 2003;33(6):635-55.

Deuschl et al., Treatment of patients with essential tremor. Lancet Neurol. Feb. 2011;10(2):148-61.

(56) References Cited

OTHER PUBLICATIONS

Diouf et al., Synthesis and preliminary pharmacological results on new naphthalene derivatives as 5-HT(4) receptor ligands. Eur J Med Chem. Jul.-Aug. 2000;35(7-8):699-706.

Dixon, Efficient analysis of experimental observations. Annu Rev Pharmacol Toxicol. 1980;20:441-62.

Dogrul et al., Reversal of experimental neuropathic pain by T-type calcium channel blockers. Pain. Sep. 2003;105(1-2):159-68.

Elble et al., Task force report: scales for screening and evaluating tremor: critique and recommendations. Mov Disord. Nov. 2013;28(13):1793-800.

Emeje et al., Effect of the molecular size of carboxymethylcellulose and some polymers on the sustained release of theophylline from a hydrophilic matrix. Acta Pharm. Sep. 2006;56(3):325-35.

Ferreira et al., MDS evidence-based review of treatments for essential tremor. Mov Disord. Jul. 2019;34(7):950-958.

Fritch et al., Design, syntheses, and SAR of 2,8-diazaspiro[4.5]decanones as T-type calcium channel antagonists. Bioorg Med Chem Lett. Nov. 15, 2010;20(22):6375-8.

Giordanetto et al., T-type calcium channels inhibitors: a patent review. Expert Opin Ther Pat. Jan. 2011;21(1):85-101.

Glauser et al., Ethosuximide, valproic acid, and lamotrigine in childhood absence epilepsy. N Engl J Med. Mar. 4, 2010;362(9):790-9.

Glauser et al., Ethosuximide, valproic acid, and lamotrigine in childhood absence epilepsy: initial monotherapy outcomes at 12 months. Epilepsia. Jan. 2013;54(1):141-55.

Gomora et al., Block of cloned human T-type calcium channels by succinimide antiepileptic drugs. Mol Pharmacol. Nov. 2001;60(5):1121-32.

Harding et al., The T-type calcium channel antagonist, Z944, reduces spinal excitability and pain hypersensitivity. Br J Pharmacol. Sep. 2021;178(17):3517-3532.

Hargreaves et al., A new and sensitive method for measuring thermal nociception in cutaneous hyperalgesia. Pain. Jan. 1988;32(1):77-88.

Hayashi et al., Pathophysiological significance of T-type Ca2+ channels: role of T-type Ca2+ channels in renal microcirculation. J Pharmacol Sci. Nov. 2005;99(3):221-7.

Heady et al., Molecular pharmacology of T-type Ca2+ channels. Jpn J Pharmacol. Apr. 2001;85(4):339-50.

Heo et al., T-type Ca2+ channel blockers suppress the growth of human cancer cells. Bioorg Med Chem Lett. Jul. 15, 2008;18(14):3899-901.

Huguenard, Low-threshold calcium currents in central nervous system neurons. Annu Rev Physiol. 1996;58:329-48.

Itoh et al., Synthesis and pharmacological evaluation of carboxamide derivatives as selective serotoninergic 5-HT(4) receptor agonists. Eur J Med Chem. 1999;34:329-341.

Itoh et al., Synthesis and pharmacological properties of novel benzamide derivatives acting as ligands to the 5-hydroxytryptamine 4 (5-HT4) receptor. European Journal of Medicinal Chemistry. Dec. 1999;34(12):1101-1108.

Kanuma et al., Lead optimization of 4-(dimethylamino)quinazolines, potent and selective antagonists for the melanin-concentrating hormone receptor 1. Bioorg Med Chem Lett. Sep. 1, 2005;15(17):3853-6.

Kim et al., Altered nociceptive response in mice deficient in the alpha(1B) subunit of the voltage-dependent calcium channel. Mol Cell Neurosci. Aug. 2001;18(2):235-45.

Kim et al., An experimental model for peripheral neuropathy produced by segmental spinal nerve ligation in the rat. Pain. Sep. 1992;50(3):355-363.

Lee, Z944: A first in class T-type calcium channel modulator for the treatment of pain. J Peripheral Nervous System. 2014; 19(Suppl):S10-S14.

Lee, Z944: An Oral T-type calcium channel modulator for the treatment of pain. Ion Channel Retreat. Slideshow, 11 pages, Jun. 25, 2014.

Lopez-Rodriguez et al., 3-D-QSAR/CoMFA and recognition models of benzimidazole derivatives at the 5-HT(4) receptor. Bioorg Med Chem Lett. Nov. 5, 2001;11(21):2807-11.

Lopez-Rodriguez et al., Benzimidazole derivatives. 3. 3D-QSAR/CoMFA model and computational simulation for the recognition of 5-HT(4) receptor antagonists. J Med Chem. Oct. 24, 2002;45(22):4806-15.

Lopez-Rodriguez et al., Benzimidazole derivatives. Part 1: Synthesis and structure-activity relationships of new benzimidazole-4-carboxamides and carboxylates as potent and selective 5-HT4 receptor antagonists. Bioorg Med Chem. Nov. 1999;7(11):2271-81.

Marks et al., The T-type calcium channel antagonist Z944 disrupts prepulse inhibition in both epileptic and non-epileptic rats. Neuroscience. Sep. 22, 2016;332:121-9.

McCalmont et al., Design, synthesis, and biological evaluation of novel T-Type calcium channel antagonists. Bioorg Med Chem Lett. Jul. 16, 2004;14(14):3691-5.

McGivern et al., Targeting N-type and T-type calcium channels for the treatment of pain. Drug Discov Today. Mar. 2006;11(5-6):245-53.

Miller, Multiple calcium channels and neuronal function. Science. Jan. 2, 1987;235(4784):46-52.

Papapetropoulos et al., A Phase 2 Proof-of-Concept, Randomized, Placebo-Controlled Trial of CX-8998 in Essential Tremor. Mov Disord. Aug. 2021;36(8):1944-1949.

Papapetropoulos et al., A Phase 2, Randomized, Double-Blind, Placebo-Controlled Trial of CX-8998, a Selective Modulator of the T-Type Calcium Channel in Inadequately Treated Moderate to Severe Essential Tremor: T-CALM Study Design and Methodology for Efficacy Endpoint and Digital Biomarker Selection. Front Neurol. Jun. 11, 2019;10:597, 11 pages.

Pinault et al., Cellular and network mechanisms of genetically-determined absence seizures. Thalamus Relat Syst. 2005;3(3):181-203.

PubChem CID 919963708, N-{{1-(2-(Tert-Butylamino)-2-oxoethyl)piperidin-4-yl)methyl)-3-chloro-5-fluorobenzamide hydrochloride. 9 pages, May 8, 2021.

Reich, Essential Tremor. Med Clin North Am. Mar. 2019;103(2):351-356.

Salemme et al., Serendipity meets precision: the integration of structure-based drug design and combinatorial chemistry for efficient drug discovery. Structure. Mar. 15, 1997;5(3):319-24.

Shanklin et al., Synthesis, calcium-channel-blocking activity, and antihypertensive activity of 4-(diarylmethyl)-1-[3-(aryloxy)propyl]piperidines and structurally related compounds. J Med Chem. Oct. 1991;34(10):3011-22.

Shipe et al., Design, synthesis, and evaluation of a novel 4-aminomethyl-4-fluoropiperidine as a T-type Ca2+ channel antagonist. J Med Chem. Jul. 10, 2008;51(13):3692-5.

Snutch et al., Recent advances in the development of T-type calcium channel blockers for pain intervention. Br J Pharmacol. Jun. 2018;175(12):2375-2383.

Su et al., Upregulation of a T-type Ca2+ channel causes a long-lasting modification of neuronal firing mode after status epilepticus. J Neurosci. May 1, 2002;22(9):3645-55.

Sui et al., The association between T-type Ca2+ current and outward current in isolated human detrusor cells from stable and overactive bladders. BJU Int. Feb. 2007;99(2):436-41.

Swinyard et al., Comparative assays of antiepileptic drugs in mice and rats. J Pharmacol Exp Ther. Nov. 1952; 106(3):319-30.

Taylor et al., Calcium signaling and T-type calcium channels in cancer cell cycling. World J Gastroenterol. Aug. 28, 2008;14(32):4984-91.

Tomita et al., SAR and QSAR studies on the N-terminally acylated pentapeptide agonists for GPR54. J Med Chem. Jul. 12, 2007;50(14):3222-8.

Tringham et al., T-type calcium channel blockers that attenuate thalamic burst firing and suppress absence seizures. Sci Transl Med. Feb. 15, 2012;4(121):121ra19, 13 pages.

Uebele et al., Antagonism of T-type calcium channels inhibits high-fat diet-induced weight gain in mice. J Clin Invest. Jun. 2009;119(6):1659-67.

(56) References Cited

OTHER PUBLICATIONS

Uehata et al., Calcium sensitization of smooth muscle mediated by a Rho-associated protein kinase in hypertension. Nature. Oct. 30, 1997;389(6654):990-4.
Wilen et al., Strategies in optical resolutions. Tetrahedron. 1977;33(21):2725-2736.
Wirrell et al., Long-term psychosocial outcome in typical absence epilepsy. Sometimes a wolf in sheeps' clothing. Arch Pediatr Adolesc Med. Feb. 1997;151(2):152-8.
Xiang et al., The Discovery and Characterization of ML218: A Novel, Centrally Active T-Type Calcium Channel Inhibitor with Robust Effects in STN Neurons and in a Rodent Model of Parkinson's Disease. ACS Chem Neurosci. Dec. 21, 2011;2(12):730-742.
Yaari et al., Recruitment of apical dendritic T-type Ca2+ channels by backpropagating spikes underlies de novo intrinsic bursting in hippocampal epileptogenesis. J Physiol. Apr. 15, 2007;580(Pt. 2):435-50.
Yang et al., Discovery of 1,4-substituted piperidines as potent and selective inhibitors of T-type calcium channels. J Med Chem. Oct. 23, 2008;51(20):6471-7.
Australian Office Action for Application No. 2009253797, dated Nov. 27, 2012, 4 pages.
Chinese Office Action for Application No. 200980129679.1, dated Apr. 29, 2014, 8 pages.
Chinese Office Action for Application No. 200980129679.1, dated Feb. 28, 2013.
Chinese Office Action for Application No. 200980129679.1, dated Nov. 26, 2013, 22 pages.
European Search Report for Application No. 09757002.2, dated Feb. 28, 2013, 6 pages.
Extended European Search Report for Application No. 09757002.2, dated Nov. 24, 2011, 7 pages.
International Preliminary Report on Patentability for Application No. PCT/CA2009/000768, dated Dec. 6, 2010, 7 pages.
International Search Report and Written Opinion for Application No. PCT/CA2009/000767, dated Aug. 24, 2009, 11 pages.
International Search Report and Written Opinion for Application No. PCT/CA2009/000768, dated Sep. 11, 2009, 14 pages.
International Search Report and Written Opinion for Application No. PCT/US2017/000097, dated Mar. 12, 2018, 8 pages.
International Search Report and Written Opinion for Application No. PCT/US2020/041530, dated Oct. 13, 2020, 10 pages.
International Search Report and Written Opinion for Application No. PCT/US2021/029539, dated Sep. 2, 2021, 10 pages.
Israeli Office Action for Application No. 209581, dated Oct. 2, 2013, 4 pages.
Caira, Crystalline polymorphism of organic compounds. Design of Organic Solids. 1998;198:163-208.
Noriaki, Organic Compound Crystal Preparation Handbook. Reiaki Hirayama (Ed.). Maruzen Co., Ltd. pp. 17-23, 37-40, 45-51, 57-65, Jul. 25, 2008.
Sarma et al., Solid forms of pharmaceuticals: Polymorphs, salts and cocrystals. Korean J Chem Eng. 28(2):315-322.
Japanese Office Aciton for Application No. 2022-502103, dated Jun. 25, 2024, 9 pages.
U.S. Appl. No. 17/626,437, filed Jan. 11, 2022, 2022-0241258, Published.
U.S. Appl. No. 17/387,599, filed Jul. 28, 2021, U.S. Pat. No. 11,649,207, Issued.
U.S. Appl. No. 17/387,648, filed Jul. 28, 2021, U.S. Pat. No. 11,427,540, Issued.
U.S. Appl. No. 18/746,428, filed Jun. 18, 2024, Pending.

* cited by examiner

US 12,077,502 B2

FORMULATIONS OF T-TYPE CALCIUM CHANNEL MODULATORS AND METHODS OF USE THEREOF

CROSS REFERENCE TO RELATED APPLICATIONS

This application is a continuation of U.S. patent application Ser. No. 17/387,648, filed on Jul. 28, 2021; which is a continuation of U.S. Patent Application No. PCT/US2020/041530, filed on Jul. 10, 2020; which claims priority to and the benefit of U.S. Provisional Patent Application No. 62/873,022, filed on Jul. 11, 2019, U.S. Provisional Patent Application No. 62/934,820, filed on Nov. 13, 2019, and U.S. Provisional Patent Application No. 62/958,923, filed on Jan. 9, 2020. The entire contents of each of the foregoing applications are hereby incorporated herein by reference.

BACKGROUND

T-type calcium channels are low-voltage activated ion channels that mediate the influx of calcium into cells. Aberrant function of these ion channels is associated with several diseases or conditions, including psychiatric disorder (e.g., mood disorder (e.g., major depressive disorder)), pain, tremor (e.g., essential tremor), epilepsy, or an epilepsy syndrome (e.g., absence seizures and juvenile myoclonic epilepsy). Accordingly, compounds that selectively modulate T-type calcium channel in mammals may be useful in treatment of such disease states.

SUMMARY OF THE INVENTION

Described herein are compositions and dosage forms useful for preventing and/or treating a disease or condition relating to aberrant function of a T-type calcium channel, such as epilepsy and epilepsy syndromes (e.g., absence seizures, juvenile myoclonic epilepsy, or a genetic epilepsy) and mood disorders (e.g., major depressive disorder). The present invention further comprises methods for modulating the function of a T-type calcium channel.

In one aspect, the present invention provides a pharmaceutical composition comprising the compound of formula (I) or a pharmaceutically acceptable salt thereof, and an excipient that functions to modify the release rate of the compound of formula (I) or a pharmaceutically acceptable salt thereof.

In one aspect, the present invention provides an oral dosage form comprising: the compound of formula (I) or a pharmaceutically acceptable salt thereof and a modified-release polymer (e.g., a controlled-release polymer, hydrophilic matrix polymers, e.g., an HPMC polymer as a hydrophilic matrix polymer, hydrophobic matrix polymers (e.g., ethyl cellulose, ethocel), or polyacrylate polymers (e.g., Eudragit RL100, Eudragit RS100)). In some embodiments, the dosage form comprises from about 0.9% by weight to about 40% by weight of the compound of formula (I) or a pharmaceutically acceptable salt thereof (e.g., the compound of formula (II)). In other embodiments, the dosage form comprises from about 1 mg to about 40 mg (e.g., about 5 mg, about 10 mg, about 15 mg, about 20 mg, about 25 mg, about 30 mg, about 35 mg, about 40 mg) of the compound of formula (I) or a pharmaceutically acceptable salt thereof (e.g., the compound of formula (II)).

The dosage form disclosed herein may comprise from about 10% by weight to about 70% by weight of the modified-release polymer. The dosage form disclosed herein may comprise a diluent (e.g., microcrystalline cellulose).

In another aspect, the present invention discloses an oral dosage form comprising: from about 15 mg to 25 mg of the compound of formula (I) or a pharmaceutically acceptable salt thereof (e.g., the compound of formula (II)); and from about 55 mg to 65 mg of an HPMC polymer.

In another aspect, the present invention provides an oral dosage form comprising: from about 14% by weight to about 25% by weight of the compound of formula (I) or a pharmaceutically acceptable salt thereof (e.g., the compound of formula (II)); and from about 53% by weight to about 64% by weight of an HPMC polymer.

Also provided herein is an oral dosage form comprising: from about 3 mg to 8 mg of the compound of formula (I) or a pharmaceutically acceptable salt thereof (e.g., the compound of formula (II)); and from about 55 mg to 65 mg of an HPMC polymer.

In one aspect, provided herein is an oral dosage form comprising: from about 3% by weight to about 8% by weight of the compound of formula (I) or a pharmaceutically acceptable salt thereof (e.g., the compound of formula (II)); and from about 53% to about 64% by weight of an HPMC polymer.

The present invention provides, in part, an oral (e.g., particulate) composition comprising: the compound of formula (I) or a pharmaceutically acceptable salt thereof (e.g., the compound of formula (II)); and a modified-release polymer (e.g., a controlled-release polymer, hydrophilic matrix polymers, e.g., an HPMC polymer, hydrophobic matrix polymers (e.g., ethyl cellulose, ethocel), or polyacrylate polymers (e.g., Eudragit RL100, Eudragit RS100)).

In some embodiments, the composition comprises from about 0.9% by weight to about 40% by weight of the compound of formula (I) or a pharmaceutically acceptable salt thereof (e.g., the compound of formula (II)). In certain embodiments, the composition comprises from about 1 mg to about 40 mg (e.g., about 5 mg, about 10 mg, about 15 mg, about 20 mg, about 25 mg, about 30 mg, about 35 mg, about 40 mg) of the compound of formula (I) or a pharmaceutically acceptable salt thereof (e.g., the compound of formula (II)).

Also provided herein is an oral (e.g., particulate) composition comprising: from about 15 mg to 25 mg of the compound of formula (I) or a pharmaceutically acceptable salt thereof (e.g., the compound of formula (II)); and from about 55 mg to 65 mg HPMC.

In another aspect, the present invention provides an oral (e.g., particulate) composition comprising: from about 14% by weight to about 25% by weight of the compound of formula (I) or a pharmaceutically acceptable salt thereof (e.g., the compound of formula (II)); and from about 53% to about 64% by weight of an HPMC polymer.

Provided herein, in part, is an oral (e.g., particulate) composition comprising: from about 3 mg to 8 mg of the compound of formula (I) or a pharmaceutically acceptable salt thereof (e.g., the compound of formula (II)); and from about 55 mg to 65 mg HPMC.

The present invention discloses, in part, an oral (e.g., particulate, swellable core) composition comprising: from about 3% by weight to about 8% by weight of the compound of formula (I) or a pharmaceutically acceptable salt thereof (e.g., the compound of formula (II)); and from about 53% to about 64% by weight of an HPMC polymer.

In one aspect, the present invention provides a crystalline form of the compound of formula (I) or a pharmaceutically acceptable salt thereof (e.g., the compound of formula (II)), wherein the crystalline form exhibits an X-ray powder diffraction pattern comprising peaks at the following diffraction angles (2θ): 16.2±0.2, 17.4±0.2, and 26.6±0.2.

In another aspect, the present invention provides a crystalline form of the compound of formula (I) or a pharmaceutically acceptable salt thereof (e.g., the compound of formula (II), wherein the crystalline form exhibits an X-ray powder diffraction pattern comprising peaks at the following diffraction angles (2θ): 21.9±0.2, 18.5±0.2, and 17.8±0.2.

The present invention provides, in part, a method of treating a neurological disorder in a subject in need thereof, wherein the method comprises administering to the subject the oral dosage, the composition, or the crystalline form disclosed herein. In some embodiments, the neurological disorder is epilepsy. In other embodiments, the epilepsy is juvenile epilepsy. In certain embodiments, the epilepsy is genetic epilepsy (e.g., CACNA1G related genetic generalized epilepsy). In some embodiments, the neurological disorder is absence seizure. In other embodiments, the neurological disorder is absence epilepsy (e.g., CACNA1H related absence epilepsy). In certain embodiments, the neurological disorder is epilepsy related to CACNA1G, H or I. In some embodiments, the epilepsy is childhood absence epilepsy (CAE). In other embodiments, the epilepsy is juvenile absence epilepsy (JAE). In certain embodiments, the epilepsy is Lenox-Gastaut Syndrome. In some embodiments, the neurological disorder is pain (e.g., acute pain, chronic pain, neuropathic pain, inflammatory pain, nociceptive pain, central pain; e.g., thalamic pain; or migraine). In other embodiments, the neurological disorder is tremor (e.g., essential tremor, Parkinson's tremor, or cerebellar tremor, CACNA1G related tremor). In certain embodiments, the neurological disorder is ataxia (e.g., spinocerebellar ataxia, or spinocerebellar ataxia with CACNA1G mutations). In other embodiments, the neurological disorder is tinnitus. In some embodiments, the neurological disorder is a disorder of wakefulness.

In another aspect, provided herein is a method of treating a psychiatric disorder in a subject in need thereof, wherein the method comprises administering to the subject the oral dosage, the composition, or the crystalline form disclosed herein. In some embodiments, the psychiatric disorder is a mood disorder. In other embodiments, the mood disorder is major depressive disorder.

In certain embodiments of the methods described herein, the dosage form is administered to the subject once a day. The dosage form may be administered to the subject twice a day. The dosage form may be administered to the subject every other day.

In some embodiments of the methods described herein, about 15 mg to 25 mg (e.g., about 20 mg) of the compound of formula (I) or a pharmaceutically acceptable salt thereof (e.g., the compound of formula (II)) may be administered to the subject daily or about 30 mg to 50 mg (e.g., about 40 mg) of the compound of formula (I) or a pharmaceutically acceptable salt thereof (e.g., the compound of formula (II)) is administered to the subject daily.

In certain embodiments of the methods described herein, the dosage form, upon administration to the subject, may have a reduced $C_{max}$ value than a reference oral dosage form (e.g., a dosage form with any intended release rate profile e.g., modified release rate profile, a dosage form that does not have a modified release rate profile, a dosage form that does not have a modified-release polymer, e.g., an HPMC polymer). In other embodiments of the methods disclosed herein, the dosage form, upon administration to the subject, may have a greater $t_{max}$ value than a reference oral dosage form (e.g., a dosage form with any intended release rate profile e.g., modified release rate profile, a dosage form that does not have a modified release rate profile, a dosage form that does not have a modified-release polymer, e.g., an HPMC polymer).

Also provided herein is a method of treating a generalized epileptic syndrome with absence seizures in a patient in need thereof, comprising administering to the patient a sufficient amount of the compound of formula (I) or a pharmaceutically acceptable salt thereof (e.g., the compound of formula (II)) (e.g., the oral dosage form, the composition, or the crystalline form disclosed herein) that results in reduction of the number of seizures.

In one aspect, provided herein is a method of treating a generalized epileptic syndrome with absence seizures in a patient in need thereof, comprising administering to the patient a sufficient amount of the compound of formula (I) or a pharmaceutically acceptable salt thereof (e.g., the compound of formula (II)) (e.g., the oral dosage form, the composition, or the crystalline form disclosed herein) that results in reduction of the seizure density as measured by Electroencephalogram (EEG).

Provided herein, in part, is a method of treating a generalized epileptic syndrome with absence seizures in a patient in need thereof, comprising administering to the patient a sufficient amount of the compound of formula (I) or a pharmaceutically acceptable salt thereof (e.g., the compound of formula (II)) (e.g., the oral dosage form, the composition, or the crystalline form disclosed herein) that results in reduction of the mean seizure duration as measured by EEG.

In another aspect, disclosed herein is a method of treating a generalized epileptic syndrome with absence seizures in a patient in need thereof, comprising administering to the patient a sufficient amount of the compound of formula (I) or a pharmaceutically acceptable salt thereof (e.g., the compound of formula (II) (e.g., the oral dosage form, the composition, or the crystalline form disclosed herein) that results in reduction of the cumulative seizure duration as measured by EEG.

Provided herein, in part, is a method of treating a generalized epileptic syndrome with absence seizures in a patient in need thereof, comprising administering to the patient a sufficient amount of the compound of formula (I) or a pharmaceutically acceptable salt thereof (e.g., the compound of formula (II)) (e.g., the oral dosage, the composition, or the crystalline described herein) that results in reduction of the total time with 2.5-4 Hz spike wave discharges after hyperventilation and photic stimulation challenges as measured by EEG.

In another aspect, a method of treating a generalized epileptic syndrome with absence seizures in a patient in need thereof, comprising administering to the patient a sufficient amount of the compound of formula (I) or a pharmaceutically acceptable salt thereof (e.g., the compound of formula (II)) (e.g., the oral dosage form, the composition, or the crystalline form) that results in reduction of global severity as measured by Clinical Global Impression-Severity (CGI-S) or Clinical Global Impression-Improvement (CGI-I) scores is provided herein.

Also provided herein is a method of treating an essential tremor in a patient in need thereof, comprising administering to the patient a sufficient amount of the compound of formula (I) or a pharmaceutically acceptable salt thereof (e.g., the compound of formula (II)) (e.g., the oral dosage form, the composition, or the crystalline form disclosed herein) that results in reduction of the essential tremor as assessed by The Essential Tremor Rating Assessment Scale (TETRAS) score. In some embodiments, the reduction of the essential tremor is assessed by The Essential Tremor Rating Assessment Scale (TETRAS) upper limb score. In other embodiments, the reduction of the essential tremor is assessed by TETRAS-ADL (activities of daily living). the reduction of the essential tremor is assessed by TETRAS performance subscale score or TETRAS performance individual items.

Also provided herein is a method of treating an essential tremor in a patient in need thereof, comprising administering to the patient a sufficient amount of the compound of formula (I) or a pharmaceutically acceptable salt thereof (e.g., the compound of formula (II)) (e.g., the oral dosage, the composition, or the crystalline form disclosed herein) that results in reduction of the essential tremor as assessed by accelerometer-based upper limb score.

In another aspect, provided herein is a method of treating an essential tremor in a patient in need thereof, comprising administering to the patient a sufficient amount of the compound of formula (I) or a pharmaceutically acceptable salt thereof (e.g., the compound of formula (II)) (e.g., the oral dosage form, the composition, or the crystalline form disclosed herein) that results in reduction of sigma frequency band. In some embodiments, the essential tremor is upper limb tremor.

Other objects and advantages will become apparent to those skilled in the art from a consideration of the ensuing Brief Description of the Figures, Detailed Description, Examples, and Claims.

DETAILED DESCRIPTION OF THE INVENTION

Figure 1:
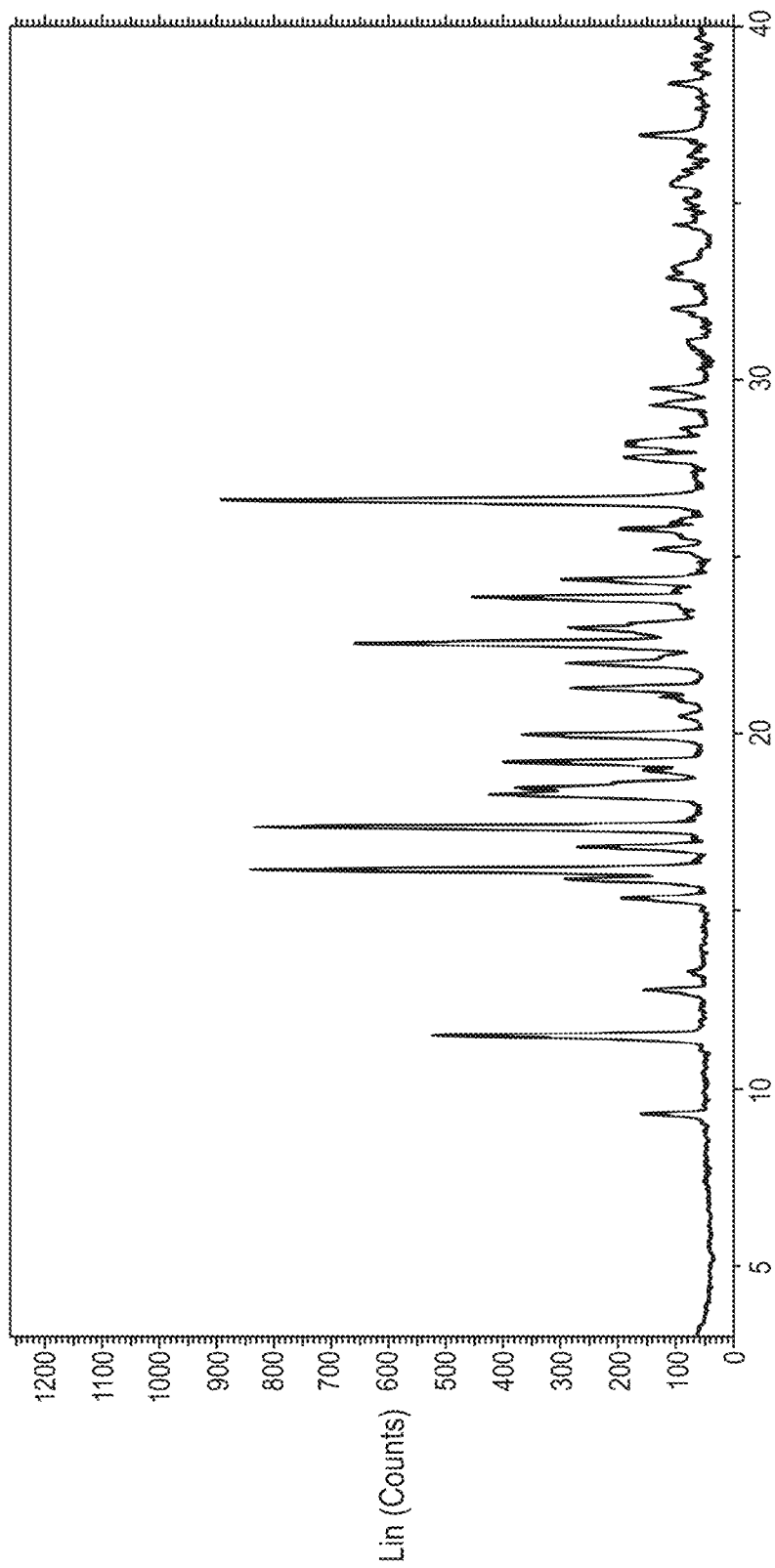
FIG. 1 is a powder X-ray diffractogram of form C of the compound of formula (II).

As generally described herein, the present invention provides compositions or dosage forms (e.g., including the compound of formula (I) or a pharmaceutically acceptable salt thereof) useful for preventing and/or treating a disease or condition relating to function of a T-type calcium channel, e.g., epilepsy or epilepsy syndromes (e.g., absence seizures, juvenile myoclonic epilepsy, or a genetic epilepsy). Methods are also presented for treating mood disorders (e.g., depression, major depressive disorder, dysthymic disorder (e.g., mild depression), bipolar disorder (e.g., I and/or II), anxiety disorders (e.g., generalized anxiety disorder (GAD), social anxiety disorder), stress, post-traumatic stress disorder (PTSD), compulsive disorders (e.g., obsessive compulsive disorder (OCD)). Methods are also presented that are useful for modulating the function of a T-type calcium channel. Methods are also presented for treating pain (e.g., acute pain, chronic pain, neuropathic pain, inflammatory pain, nociceptive pain, central pain; e.g., thalamic pain; or migraine). Methods are also presented for treating tremor (e.g., essential tremor, Parkinson's tremor, or cerebellar tremor). Methods are also presented for treating ataxia (e.g., spinocerebellar ataxia, cerebellar ataxia, or spinocerebellar ataxia with CACNA1G mutations). Methods are also presented for treating tinnitus. Methods are also presented for treating insomnia.

Definitions

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, the term "refractory" refers to a disease, disorder, or condition that does not readily yield or respond to therapy or treatment, or is not controlled by a therapy or treatment. In some embodiments, a disease, disorder, or condition described herein is refractory (e.g., refractory epilepsy or refractory absence seizures) and does not respond to standard therapy or treatment.

As used herein, a "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

The terms "disease", "disorder", and "condition" are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, stereoisomers thereof (e.g., enantiomers, diastereomers) and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "modified-release polymer" refers to a polymer that is used in a formulation (e.g., tablets and capsules) to modify the release rate of the drug upon the administration to a subject. For example, a modified-release polymer is used to dissolve a drug over time in order to be released slower and steadier into the bloodstream. For example, a modified-release polymer is a controlled-release polymer. For example, a modified-release polymer or a controlled-release polymer is an HPMC polymer. In some embodiments, a modified-release polymer may include hydrophilic matrix polymers (e.g., hypromellose, HPMC (hydroxylpropyl methylcellulose)), hydrophobic matrix polymers (e.g., ethyl cellulose, ethocel), or polyacrylate polymers (e.g., Eudragit RL100, Eudragit RS100).

The term "diluent" as used herein refers to an excipient used to increase weight and improve content uniformity. For example, diluents include cellulose derivatives (e.g., microcrystalline cellulose), starches (e.g., hydrolyzed starches, and partially pregelatinized starches), anhydrous lactose, lactose monohydrate, di-calcium phosphate (DCP), sugar alcohols (e.g., sorbitol, xylitol and mannitol)).

The term "glidant" as used herein refers to an excipient used to promote powder flow by reducing interparticle friction and cohesion. For example, glidants include fumed silica (e.g., colloidal silicon dioxide), talc, and magnesium carbonate.

The term "lubricant" as used herein refers to an excipient used to prevent ingredients from clumping together and from sticking to the tablet punches or capsule filling machine. Lubricants are also used to ensure that tablet formation and ejection can occur with low friction between the solid and die wall. For example, lubricants include magnesium stearate, calcium stearate, stearic acid, talc, silica, and fats (e.g., vegetable stearin).

The term "coating" as used herein refers to an excipient to protect tablet ingredients from deterioration by moisture in the air and make large or unpleasant-tasting tablets easier to swallow. These and other exemplary substituents are described in more detail in the Detailed Description, Examples, and Claims. The invention is not intended to be limited in any manner by the above exemplary listing of substituents.

Dosage Forms and Compositions

In one aspect, the present invention features dosage forms or compositions for the modulation of T-type calcium channels, as well as diseases, disorders, or conditions associated with function thereof (e.g., mood disorder (e.g., major depressive disorder), epilepsy or an epilepsy syndrome, e.g., absence seizures, juvenile myoclonic epilepsy, status epilepticus, or a genetic epilepsy).

In another aspect, the present invention provides a dosage form comprising a compound of formula (I):

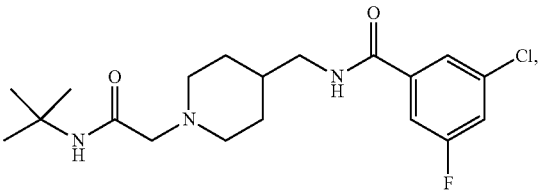 [SMILES: CC(C)(C)NC(=O)CN1CCC(CNC(=O)c2cc(F)cc(Cl)c2)CC1]

or a pharmaceutically acceptable salt (e.g., co-crystal) or solvate thereof.

In another aspect, the present invention provides a dosage form comprising a compound of formula (II):

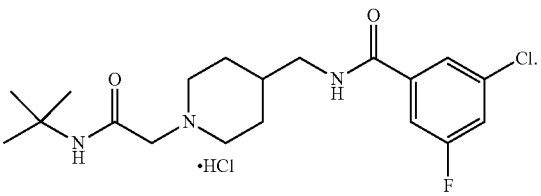 [SMILES: CC(C)(C)NC(=O)CN1CCC(CNC(=O)c2cc(F)cc(Cl)c2)CC1 ; Cl]

Modified-Release Dosage Forms and Compositions

In one aspect, the present invention provides a pharmaceutical composition comprising the compound of formula (I) or a pharmaceutically acceptable salt thereof, and an excipient that functions to modify the release rate of the compound of formula (I) or a pharmaceutically acceptable salt thereof. In some embodiments, the pharmaceutical composition may be a swellable core technology formulations.

In one aspect, the present disclosure provides an oral dosage form comprising: the compound of formula (I) or a pharmaceutically acceptable salt thereof (e.g., the compound of formula (II)); and a modified-release polymer (e.g., a controlled-release polymer, hydrophilic matrix polymers, e.g., an HPMC polymer, hydrophobic matrix polymers (e.g., ethyl cellulose, ethocel), or polyacrylate polymers (e.g., Eudragit RL100, Eudragit RS100)).

In one aspect, the present invention provides a dosage form or composition comprising the compound of formula (I) or a pharmaceutically acceptable salt thereof (e.g., the compound of formula (II)) and a modified-release polymer (e.g., a controlled-release polymer, hydrophilic matrix polymers, e.g., an HPMC polymer, hydrophobic matrix polymers (e.g., ethyl cellulose, ethocel), or polyacrylate polymers (e.g., Eudragit RL100, Eudragit RS100)), for example, in an amount sufficient to modify the release rate of the compound of formula (I) or a pharmaceutically acceptable salt thereof (e.g., the compound of formula (II)) upon an administration to the subject.

In some embodiments, the dosage form comprises from about 0.9% by weight to about 40% by weight (e.g., from about 0.9% by weight to about 30%, from about 1% by weight to about 25% by weight, from about 2% by weight to about 25% by weight, from about 3% by weight to about 20% by weight, from about 4% by weight to about 20% by weight, from about 5% by weight to about 20% by weight, from about 5% by weight to about 15% by weight, from about 5% by weight to about 10% by weight, or about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 40% by weight) of the compound of formula (I) or a pharmaceutically acceptable salt thereof (e.g., the compound of formula (II)). In some embodiments, the dosage form comprises about 30% by weight to about 40% by weight of the compound of formula (I) or a pharmaceutically acceptable salt thereof (e.g., the compound of formula (II)).

In some embodiments, the dosage form comprises from about 14% by weight to about 25% by weight of the compound of formula (I) or a pharmaceutically acceptable salt thereof (e.g., the compound of formula (II)). In some embodiments, the dosage form comprises from about 19% by weight to about 20% by weight of the compound of formula (I) or a pharmaceutically acceptable salt thereof (e.g., the compound of formula (II)). In some embodiments, the dosage form comprises from about 21% by weight to about 22% by weight of the compound of formula (I) or a pharmaceutically acceptable salt thereof (e.g., the compound of formula (II)). In some embodiments, the dosage form comprises from about 4% by weight to about 15% by weight of the compound of formula (I) or a pharmaceutically acceptable salt thereof (e.g., the compound of formula (II)). In some embodiments, the dosage form comprises from about 4% by weight to about 10% by weight of the compound of formula (I) or a pharmaceutically acceptable salt thereof (e.g., the compound of formula (II)). In some embodiments, the dosage form comprises form about 4% by weight to about 5% by weight of the compound of formula (I) or a pharmaceutically acceptable salt thereof (e.g., the compound of formula (II)). In some embodiments, the dosage form comprises from about 5% by weight to about 6% by weight of the compound of formula (I) or a pharmaceutically acceptable salt thereof (e.g., the compound of formula (II)). In some embodiments, the dosage form comprises from about 9% by weight to about 10% by weight of the compound of formula (I) or a pharmaceutically acceptable salt thereof (e.g., the compound of formula (II)).

In another aspect, the present invention provides a dosage form or composition comprising from about 1 mg to about 40 mg (e.g., about 5 mg, about 10 mg, about 15 mg, about 20 mg, about 25 mg, about 30 mg, about 35 mg, about 40 mg) of the compound of formula (I) or a pharmaceutically acceptable salt thereof (e.g., the compound of formula (II)) and a modified-release polymer (e.g., a controlled-release polymer, hydrophilic matrix polymers, e.g., an HPMC polymer, hydrophobic matrix polymers (e.g., ethyl cellulose, ethocel), or polyacrylate polymers (e.g., Eudragit RL100, Eudragit RS100)), for example, in an amount sufficient to modify the release rate of the compound of formula (I) or a pharmaceutically acceptable salt thereof (e.g., the compound of formula (II)) upon an administration to the subject.

In other embodiments, the dosage form comprises from about 4 mg to about 6 mg (e.g., about 5 mg) of the compound of formula (I) or a pharmaceutically acceptable salt thereof (e.g., the compound of formula (II)). In certain embodiments, the dosage form comprises from about 15 mg to about 25 mg (e.g., about 20 mg) of the compound of formula (I) or a pharmaceutically acceptable salt thereof (e.g., the compound of formula (II)). In some embodiments, the dosage form comprises from about 5 mg to about 15 mg (e.g., about 10 mg) of the compound of formula (I) or a pharmaceutically acceptable salt thereof (e.g., the compound of formula (II)). In other embodiments, the dosage form comprises from about 25 mg to about 35 mg (e.g., about 30 mg) of the compound of formula (I) or a pharmaceutically acceptable salt thereof (e.g., the compound of formula (II)). In certain embodiments, the dosage form comprises from about 35 mg to about 45 mg (e.g., about 40 mg) of the compound of formula (I) or a pharmaceutically acceptable salt thereof (e.g., the compound of formula (II).

In some embodiments, the dosage form comprises from about 55 mg to 65 mg of a modified-release polymer (e.g., an HPMC polymer). In some embodiments, the dosage form comprises from about 10% by weight to about 70% by weight of the modified-release polymer (e.g., an HPMC polymer). In some embodiments, the dosage form comprises from about 50% by weight to about 60% by weight of the modified-release polymer (e.g., an HPMC polymer).

In some embodiments, the dosage form further comprises a diluent. In some embodiments, the diluent comprises microcrystalline cellulose. In some embodiments, the dosage form comprises from about 15 mg to 40 mg (e.g., from about 15 mg to about 25 mg, from about 20 mg to about 25 mg, from about 25 mg to about 30 mg, from about 30 mg to about 40 mg) microcrystalline cellulose. In some embodiments, the dosage form comprises from about 15 mg to about 25 mg microcrystalline cellulose. In some embodiments, the dosage form comprises from about 30 mg to about 40 mg microcrystalline cellulose. In some embodiments, the dosage form comprises from about 15% to about 35% by weight (e.g., from about 15% to about 20%, from about 20% to about 25%, from 25% to about 30%, from 30% to about 35% by weight) microcrystalline cellulose.

In some embodiments, the dosage form further comprises a glidant. In some embodiments, the glidant comprises colloidal silicon dioxide. In some embodiments, the dosage form further comprises a lubricant. In some embodiments, the lubricant comprises magnesium stearate. In some embodiments, the dosage form further comprises a coating.

In some embodiments, about 80% of the compound of formula (I) is released within 7 hours upon administration to a subject. In certain embodiments, about 80% of the compound of formula (I) is released in 7 hours using USP apparatus type-I, media containing 900 mL 0.1 M HCl, and a paddle speed of 100 rpm.

In some embodiments, the dosage form, upon administration to a subject, has a reduced $C_{max}$ value than a reference oral dosage form (e.g., a dosage form with any intended release rate profile e.g., modified release rate profile, a dosage form that does not have a modified release rate profile, a dosage form that does not have a modified-release polymer, e.g., an HPMC polymer). In some embodiments, the dosage form, upon administration to a subject, has a greater $t_{max}$ value than a reference oral dosage form (e.g., a dosage form with any intended release rate profile e.g., modified release rate profile, a dosage form that does not have a modified release rate profile, a dosage form that does not have a modified-release polymer, e.g., an HPMC polymer).

In other embodiments, the dosage form is administered to a patient once daily. In certain embodiments, the dosage form is administered to a patient twice daily. In some embodiments, the dosage form is a tablet. In other embodiments, the dosage form is a capsule. In certain embodiments, the dosage form is a suspension.

In another aspect, the present invention provides an oral dosage form comprising: from about 15 mg to 25 mg of the compound of formula (I) or a pharmaceutically acceptable salt thereof (e.g., the compound of formula (II)); and from about 55 mg to 65 mg of an HPMC polymer.

In another aspect, the present invention provides an oral dosage form comprising: from about 14% by weight to about 25% by weight of the compound of formula (I) or a pharmaceutically acceptable salt thereof (e.g., the compound of formula (II)); and from about 53% to about 64% by weight of an HPMC polymer.

In another aspect, the present invention provides an oral dosage form comprising: from about 3 mg to 8 mg of the compound of formula (I) or a pharmaceutically acceptable salt thereof (e.g., the compound of formula (II)); and from about 55 mg to 65 mg of an HPMC polymer.

In another aspect, the present invention provides an oral dosage form comprising: from about 3% by weight to about 8% by weight of the compound of formula (I) or a pharmaceutically acceptable salt thereof (e.g., the compound of formula (II)); and from about 53% to about 64% by weight of an HPMC polymer.

In another aspect, the present invention provides an oral (e.g., particulate) composition comprising: the compound of formula (I) or a pharmaceutically acceptable salt thereof (e.g., the compound of formula (II)); and a modified-release polymer (e.g., a controlled-release polymer, e.g., an HPMC polymer as a hydrophilic matrix polymer).

In some embodiments, the composition comprises from about 0.9% by weight to about 40% by weight of the compound of formula (I) or a pharmaceutically acceptable salt thereof (e.g., the compound of formula (II)). In some embodiments, the composition comprises from about 14% by weight to about 25% by weight of the compound of formula (I) or a pharmaceutically acceptable salt thereof (e.g., the compound of formula (II)). In some embodiments, the composition comprises about 19% by weight to about 20% by weight of the compound of formula (I) or a pharmaceutically acceptable salt thereof (e.g., the compound of formula (II)). In some embodiments, the composition comprises about 21% by weight to about 22% by weight of the compound of formula (I) or a pharmaceutically acceptable salt thereof (e.g., the compound of formula (II)). In some embodiments, the composition comprises from about 4% by weight to about 15% by weight of the compound of formula (I) or a pharmaceutically acceptable salt thereof (e.g., the compound of formula (II)). In some embodiments, the composition comprises from about 4% by weight to about 10% by weight of the compound of formula (I) or a pharmaceutically acceptable salt thereof (e.g., the compound of formula (II)). In some embodiments, the composition comprises about 4% by weight to about 5% by weight of the compound of formula (I) or a pharmaceutically acceptable salt thereof (e.g., the compound of formula (II)). In some embodiments, the composition comprises about 5% by weight to about 6% by weight of the compound of formula (I) or a pharmaceutically acceptable salt thereof (e.g., the compound of formula (II)). In some embodiments, the composition comprises about 9% by weight to about 10% by weight of the compound of formula (I) or a pharmaceutically acceptable salt thereof (e.g., the compound of formula (II)).

In some embodiments, the composition comprises from about 1 mg to about 40 mg (e.g., about 5 mg, about 10 mg, about 15 mg, about 20 mg, about 25 mg, about 30 mg, about 35 mg, about 40 mg) of the compound of formula (I) or a pharmaceutically acceptable salt thereof (e.g., the compound of formula (II)). In certain embodiments, the composition comprises from about 4 mg to about 6 mg (e.g., about 5 mg) of the compound of formula (I) or a pharmaceutically acceptable salt thereof (e.g., the compound of formula (II)). In other embodiments, the composition comprises from about 15 mg to about 25 mg (e.g., about 20 mg) of the compound of formula (I) or a pharmaceutically acceptable salt thereof (e.g., the compound of formula (II)).

In some embodiments, the composition comprises from about 55 mg to 65 mg of the modified-release polymer. In some embodiments, the composition comprises from about 10% by weight to about 70% by weight of the modified-release polymer. In some embodiments, the composition comprises from about 50% by weight to about 60% by weight of the modified-release polymer.

In some embodiments, the composition comprises a diluent. In some embodiments, the diluent comprises microcrystalline cellulose. In other embodiments, the composition comprises from about 15 mg to 40 mg (e.g., from about 15 mg to about 25 mg, from about 20 mg to about 25 mg, from about 25 mg to about 30 mg, from about 30 mg to about 40 mg), microcrystalline cellulose. In some embodiments, the composition comprises from about 15% to about 35% by weight (e.g., from about 15% to about 20%, from about 20% to about 25%, from 25% to about 30%, from 30% to about 35% by weight) microcrystalline cellulose.

In some embodiments, the composition comprises from about 15 mg to about 25 mg microcrystalline cellulose. In some embodiments, the composition comprises from about 30 mg to about 40 mg microcrystalline cellulose. In some embodiments, the composition further comprises a glidant. In some embodiments, the glidant comprises colloidal silicon dioxide. In some embodiments, the composition further comprises a lubricant. In some embodiments, the lubricant comprises magnesium stearate. In some embodiments, the composition further comprises a coating. In some embodiments, the compound of formula (I) or (II) is stable within the formulation at about 25° C. at 60% relative humidity for at least 24 months. In some embodiments, the compound is stable at about 25° C. at 60% relative humidity for at least 36 months. In some embodiments, the compound is stable at about 25° C. at 60% relative humidity for at least 48 months.

In other embodiments, the compound is stable at about 25° C. at 60% relative humidity for at least 60 months. In some embodiments, the compound is stable at about 40° C. at 75% relative humidity for at least 6 months.

In another aspect, the present invention provides an oral (e.g., particulate) composition comprising: from about 15 mg to 25 mg of the compound of formula (I) or a pharmaceutically acceptable salt thereof (e.g., the compound of formula (II)); and from about 55 mg to 65 mg HPMC.

In another aspect, the present invention provides an oral (e.g., particulate) composition comprising: from about 14% by weight to about 25% by weight of the compound of formula (I) or a pharmaceutically acceptable salt thereof (e.g., the compound of formula (II)); and from about 53% to about 64% by weight of an HPMC polymer.

In another aspect, the present invention provides an oral (e.g., particulate) composition comprising: from about 3 mg to 8 mg of the compound of formula (I) or a pharmaceutically acceptable salt thereof (e.g., the compound of formula (II)); and from about 55 mg to 65 mg HPMC.

In another aspect, the present invention provides an oral (e.g., particulate) composition comprising: from about 3% by weight to about 8% by weight of the compound of formula (I) or a pharmaceutically acceptable salt thereof (e.g., the compound of formula (II)); and from about 53% to about 64% by weight of an HPMC polymer.

In some embodiments of the oral dosage forms or compositions described herein, the compound of formula (I) or a pharmaceutically acceptable salt thereof (e.g., the compound of formula (II)) is a crystalline form. In certain embodiments, the crystalline form is a crystalline form as described herein.

Crystalline Form of the Compound of Formula (II)

Also provided herein is a crystalline form of the compound of formula (II), wherein the crystalline form exhibits an X-ray powder diffraction pattern comprising peaks at the following diffraction angles (2θ): 16.2±0.2, 17.4±0.2, and 26.6±0.2.

Figure 2:
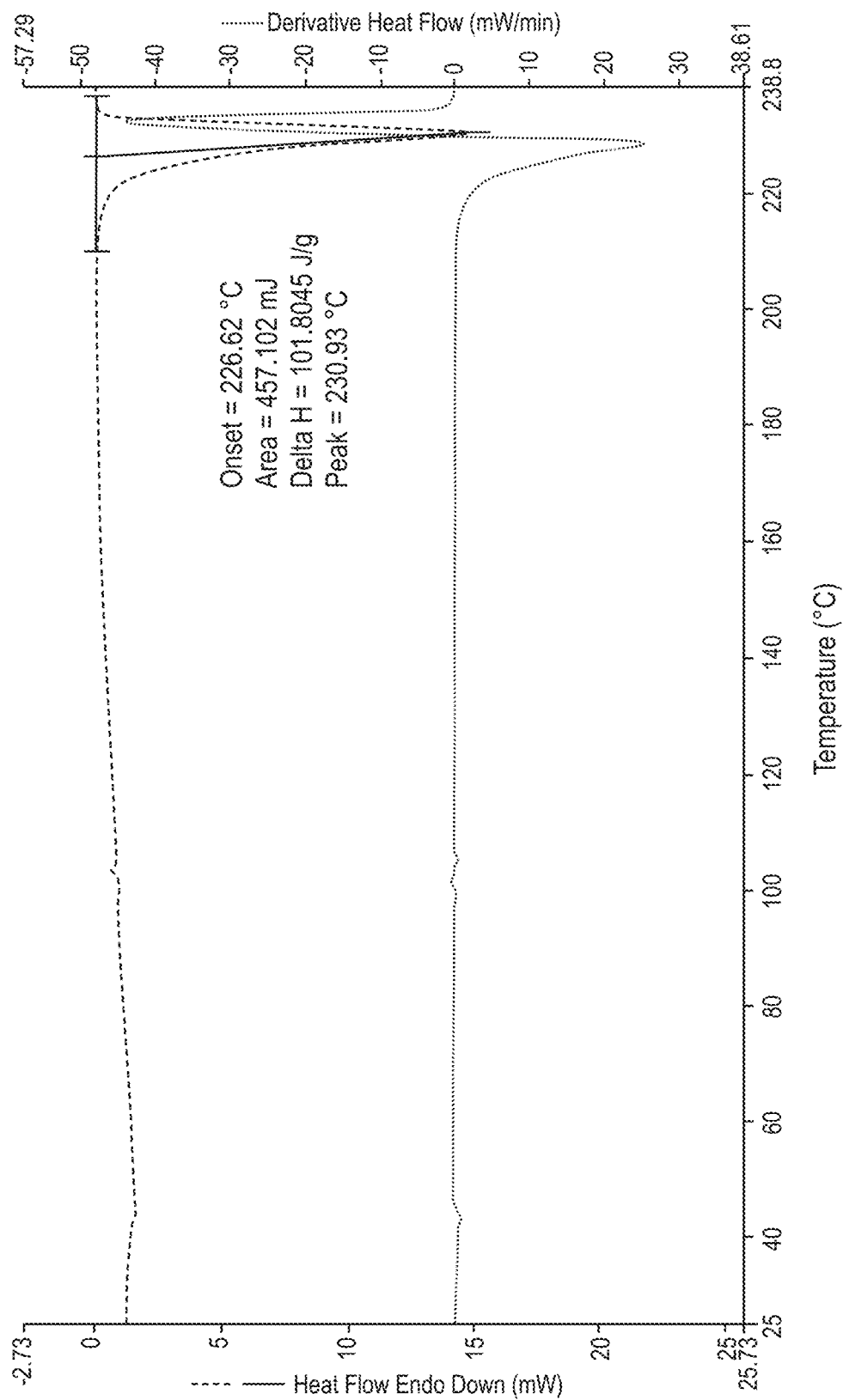
FIG. 2 is a differential scanning calorimetry (DSC) thermogram of form C of the compound of formula (II).

In some embodiments, the crystalline form exhibits an X-ray powder diffraction pattern comprising peaks at the following diffraction angles (2θ): 11.5±0.2, 16.2±0.2, 17.4±0.2, 22.6±0.2, and 26.6±0.2. In other embodiments, the crystalline form exhibits an X-ray powder diffraction pattern comprising peaks at the following diffraction angles (2θ): 11.5±0.2, 16.2±0.2, 17.4±0.2, 18.3±0.2, 18.5±0.2, 19.2±0.2, 20.0±0.2, 22.6±0.2, 23.9±0.2, and 26.6±0.2. In certain embodiments, the crystalline form has a X-ray powder diffraction pattern substantially the same as depicted in FIG. 1. In some embodiments, the powder X-ray diffraction pattern was obtained using Cu Kα radiation. In certain embodiments, the crystalline form has a melting point onset as determined by differential scanning calorimetry at about 226.6° C. In some embodiments, the crystalline form has a differential scanning calorimetry curve substantially the same as shown in FIG. 2.

In another aspect, provided herein is a crystalline form of the compound of formula (II), wherein the crystalline form exhibits an X-ray powder diffraction pattern comprising peaks at the following diffraction angles (2θ): 21.9±0.2, 18.5±0.2, and 17.8±0.2.

Figure 7:
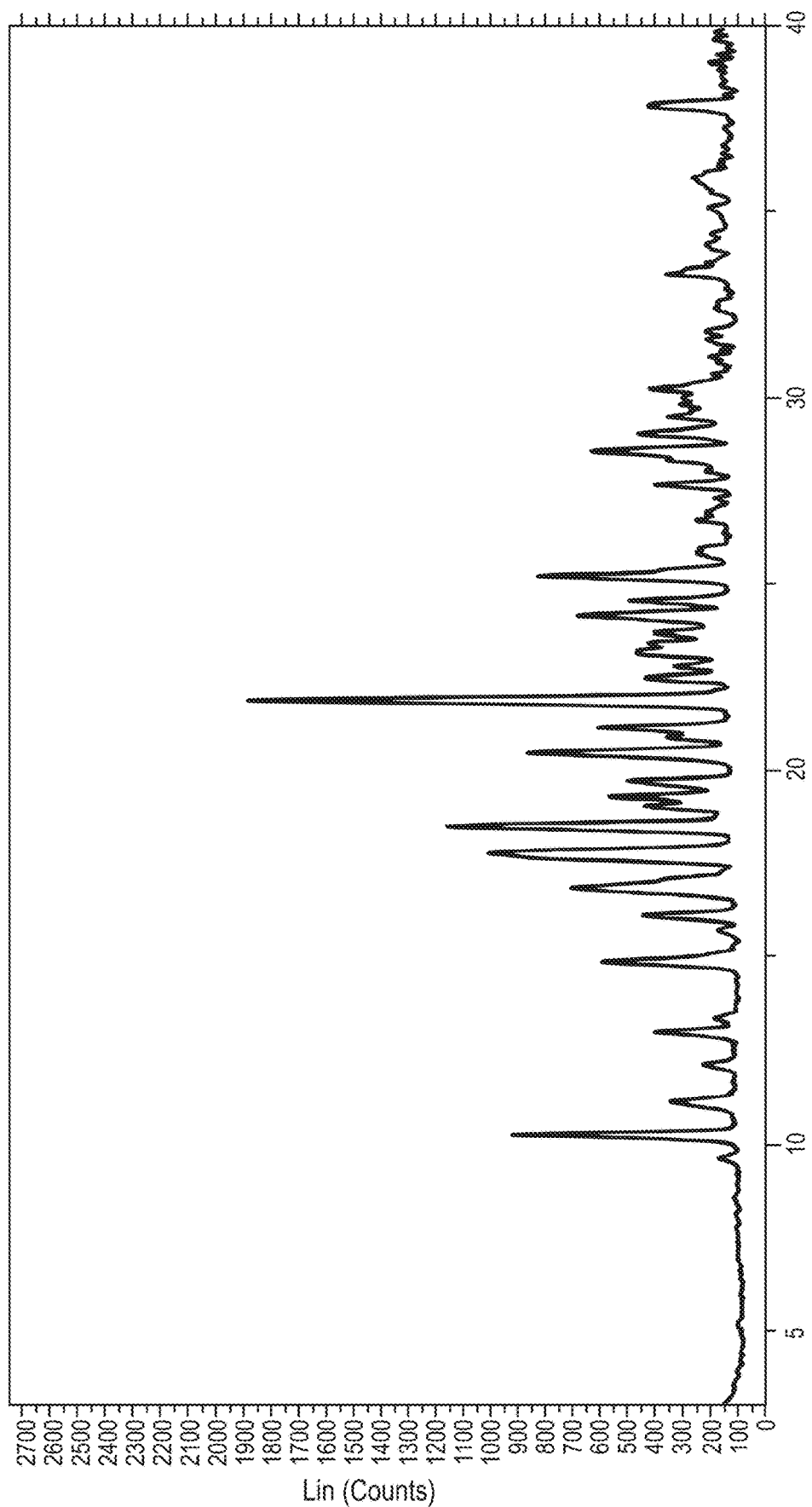
FIG. 7 is a powder X-ray diffractogram of pattern B of the compound of formula (II).
Figure 8A:
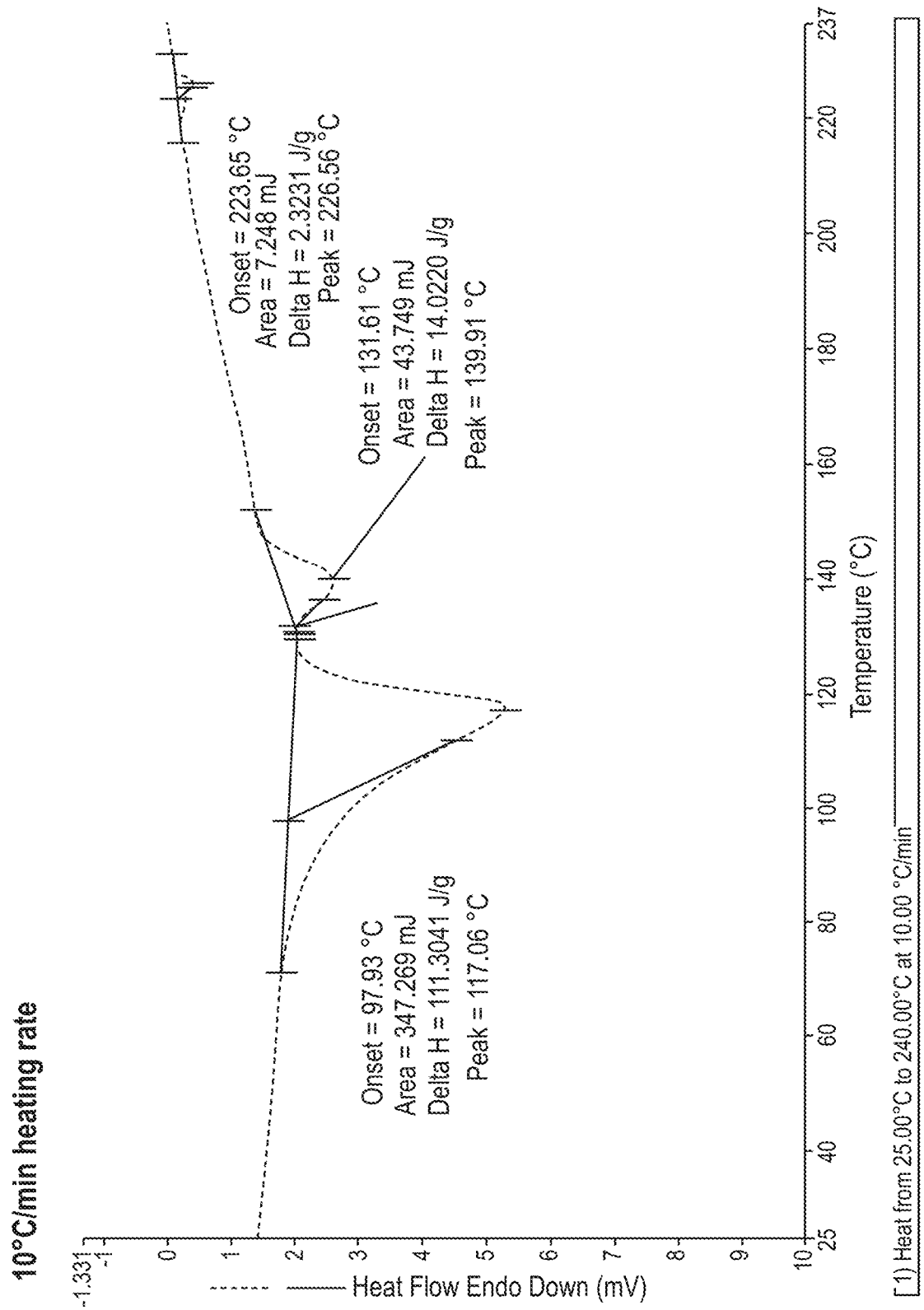
FIG. 8A is a differential scanning calorimetry (DSC) thermogram of pattern B of the compound of formula (II) at a heating rate of 10° C./min.
Figure 8B:
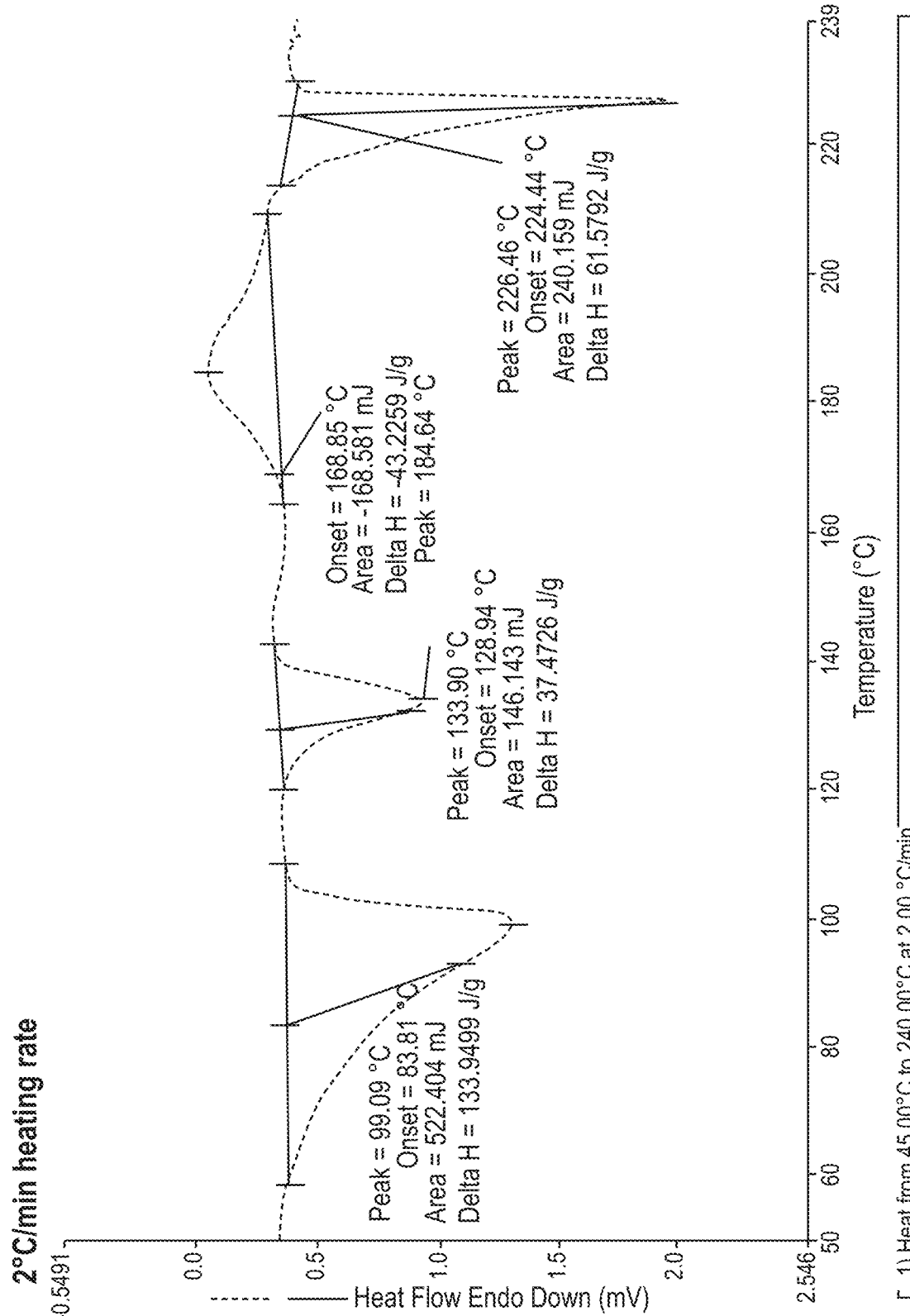
FIG. 8B is a DSC thermogram of pattern B of the compound of formula (II) at a heating rate of 2° C./min.

In some embodiments, the crystalline form exhibits an X-ray powder diffraction pattern comprising peaks at the following diffraction angles (2θ): 21.9±0.2, 18.5±0.2, 17.8±0.2, 10.2±0.2, and 20.5±0.2. In other embodiments, the crystalline form exhibits an X-ray powder diffraction pattern comprising peaks at the following diffraction angles (2θ): 21.9±0.2, 18.5±0.2, 17.8±0.2, 10.2±0.2, 20.5±0.2, 25.2±0.2, 16.9±0.2, 24.2±0.2, 28.6±0.2, and 21.2±0.2. In certain embodiments, the crystalline form has a X-ray powder diffraction pattern substantially the same as depicted in FIG. 7. In some embodiments, the powder X-ray diffraction pattern was obtained using Cu Kα radiation. In certain embodiments, the crystalline form has a melting point onset as determined by differential scanning calorimetry at about 97.9, 131.6, 223.7, 83.8, 128.9, 168.9, or 224.4° C. In some embodiments, the crystalline form has a differential scanning calorimetry curve substantially the same as shown in FIG. 8.

Immediate-Release Formulations

In another aspect, the present invention provides a dosage form or composition comprising the compound of formula (I) or a pharmaceutically acceptable salt thereof (e.g., the compound of formula (II)), where the compound of formula (I) or a pharmaceutically acceptable salt thereof (e.g., the compound of formula (II)) is released immediately upon an administration to the subject.

Also provided herein is an oral capsule for immediate release comprising: from about 15 mg to about 20 mg of the compound of formula (I) or a pharmaceutically acceptable salt thereof (e.g., the compound of formula (II)); and from about 75 mg to 85 mg diluent; from about 2 mg to 10 mg binder; from about 1% to about 5% disintegrant; and from about 0.1 mg to 5 mg lubricant.

Administrations

In some embodiments, the dosage form is administered to the subject more than once a day (e.g., twice a day, three times a day, or four times a day).

In some embodiments, the dosage form is administered to the subject once a day (e.g., one 20 mg tablet per day, two 20 mg tablets a day, three 20 mg tablets a day). In some embodiments, the dosage form is administered to the subject twice a day. In some embodiments, the dosage form is administered to the subject every other day. In certain embodiments, about 1 mg to 40 mg of the compound of formula (I) or a pharmaceutically acceptable salt thereof (e.g., the compound of formula (II)) is administered to the subject daily. In other embodiments, about 15 mg to 25 mg of the compound of formula (I) or a pharmaceutically acceptable salt thereof (e.g., the compound of formula (II)) is administered to the subject daily. In certain embodiments, about 30 mg to 40 mg of the compound of formula (I) or a pharmaceutically acceptable salt thereof (e.g., the compound of formula (II)) is administered to the subject daily.

In some embodiments, the dosage form, upon administration to the subject, has a reduced $C_{max}$ value than a reference oral dosage form (e.g., a dosage form with any intended release rate profile e.g., modified release rate profile, a dosage form that does not have a modified release rate profile, a dosage form that does not have a modified-release polymer, e.g., an HPMC polymer). In some embodiments, the dosage form, upon administration to the subject, has a greater $t_{max}$ value than a reference oral dosage form (e.g., a dosage form with any intended release rate profile e.g., modified release rate profile, a dosage form that does not have a modified release rate profile, a dosage form that does not have a modified-release polymer, e.g., an HPMC polymer).

Methods of Treatment

Described herein are compositions including the compound of formula (I) or a pharmaceutically acceptable salt thereof (e.g., the compound of formula (II)) and their use to treat a disease, disorder, or condition relating to function of T-type calcium channel.

In one aspect, provided herein is a method of treating a neurological disorder in a subject in need thereof, wherein the method comprises administering to the subject the oral dosage form or oral composition disclosed herein. In some embodiments, the subject has a mutation in one or both of the T-type calcium channel genes CACNA1H and CACNA1G. In some embodiments, the neurological disorder is epilepsy. In some embodiments, the epilepsy is juvenile epilepsy. In some embodiments, the epilepsy is genetic epilepsy. In some embodiments, the neurological disorder is absence seizure. In some embodiments, the neurological disorder is pain (e.g., acute pain, chronic pain, neuropathic pain, inflammatory pain, nociceptive pain, central pain; e.g., thalamic pain; or migraine). In some embodiments, the neurological disorder is tremor (e.g., essential tremor, Parkinson's tremor, or cerebellar tremor). In other embodiments, the neurological disorder is characterized by tremor but Parkinson's disease is not a tremor per se. In some embodiments, the neurological disorder is ataxia (e.g., spinocerebellar ataxia, or spinocerebellar ataxia with CACNA1G mutations). In some embodiments, the neurological disorder is tinnitus. In certain embodiments, the neurological disorder is a disorder of wakefulness.

In some embodiments, a composition provided by the present invention is effective in the treatment of tremor (e.g., essential tremor). In some embodiments, a composition provided by the present invention is effective in the treatment of an epilepsy or epilepsy syndrome, e.g., absence seizures, juvenile myoclonic epilepsy, status epilepticus, or a genetic epilepsy. Compositions of the invention may also modulate all T-type calcium channels, e.g., Cav3.1, Cav3.2, and/or Cav3.3. In some embodiments, a composition provided by the present invention is effective in the treatment of a psychiatric disorder, e.g., mood disorder, e.g., major depressive disorder.

In another aspect, provided herein is a method of treating a psychiatric disorder in a subject in need thereof, wherein the method comprises administering to the subject the oral dosage form disclosed herein. In some embodiments, the psychiatric disorder is a mood disorder. In some embodiments, the mood disorder is major depressive disorder.

Epilepsy and Epilepsy Syndromes

The compositions described herein are useful in the treatment of epilepsy and epilepsy syndromes. Epilepsy is a CNS disorder in which nerve cell activity in the brain becomes disrupted, causing seizures which can manifest as abnormal movements, periods of unusual behavior, sensations and sometimes loss of consciousness. Seizure symptoms will vary widely, from a simple blank stare for a few seconds to repeated twitching of their arms or legs during a seizure.

Epilepsy may involve a generalized seizure or a partial or focal seizure. All areas of the brain are involved in a generalized seizure. A person experiencing a generalized seizure may cry out or make some sound, stiffen for several seconds to a minute and then have rhythmic movements of the arms and legs. The eyes are generally open, the person may appear not to be breathing and actually turn blue. The return to consciousness is gradual and the person maybe confused from minutes to hours. The following are the main types of generalized seizures: tonic-clonic, tonic, clonic, myoclonic, myoclonic-tonic-clonic, myoclonic-atonic, atonic, and absence (typical, atypical, myoclonic, eyelid myoclonia) seizures, and epileptic spasms. In a partial or focal seizure, only part of the brain is involved, so only part of the body is affected. Depending on the part of the brain having abnormal electrical activity, symptoms may vary.

Epilepsy, as described herein, includes a generalized, partial, complex partial (e.g., seizures involving only part of the brain, but where consciousness is compromised), tonic clonic, clonic, tonic, refractory seizures, status epilepticus, absence seizures, febrile seizures, or temporal lobe epilepsy.

The compositions described herein may also be useful in the treatment of epilepsy syndromes. Severe syndromes with diffuse brain dysfunction caused, at least partly, by some aspect of epilepsy, are also referred to as epileptic encephalopathies. These are associated with frequent seizures that are resistant to treatment and severe cognitive dysfunction, for instance West syndrome.

In some embodiments, the epilepsy syndrome comprises epileptic encephalopathy, Dravet syndrome, Angelman syndrome, CDKL5 disorder, frontal lobe epilepsy, infantile spasms, West's syndrome, Juvenile Myoclonic Epilepsy, Landau-Kleffner syndrome, Lennox-Gastaut syndrome, Ohtahara syndrome, PCDH19 epilepsy, or Glut1 deficiency. In some embodiments, the epilepsy syndrome is childhood absence epilepsy (CAE). In some embodiments, the epilepsy syndrome is juvenile absence epilepsy (JAE). In some embodiments, the epilepsy syndrome is Lennox-Gastaut syndrome. In some embodiments, the epilepsy syndrome is SLC6A1 epileptic encephalopathy. In some embodiments, the epilepsy syndrome is associated with mutations in the genes that code for T-type calcium channels (e.g., CACNA1G, EEF1A2, and GABRG2 for genetic generalized epilepsy (GGE) and LGI1, TRIM3, and GABRG2 for non-acquired focal epilepsy (NAFE)). Am J Hum Genet. 2019 Aug. 1; 105(2):267-28. In some embodiments, the epilepsy syndrome is Doose syndrome or myoclonic astatic epilepsy. In some embodiments, the epilepsy syndrome is epileptic encephalopathy with continuous spike and wave during sleep (CSWS). In some embodiments, the epilepsy syndrome is Landau Kleffner Syndrome (LKS). In some embodiments, the epilepsy syndrome is Jeavons syndrome.

Absence Seizures

Absence seizures are one of the most common seizure types in patients with idiopathic generalised epilepsy (IGE) (Berg et al., Epilepsia 2000). Absence seizures are relatively brief, non-convulsive seizures characterised by abrupt onset of loss of awareness and responsiveness, usually lasting between 10-30 seconds in duration, with a rapid return to normal consciousness without post-ictal confusion. The seizures are characterised on an accompanying EEG recording by the abrupt onset and offset of generalised 1-6 Hz (e.g., 3 Hz) spike and wave discharges. Absence seizure often occur multiple times per day, interrupt learning and psychosocial functioning, and present a risk of injury because of the frequent episodes of loss of awareness. Typically, absence seizures begin in early childhood and remit by teenage years. However, in a minority of patients they persist into adulthood where they are often drug resistant, and may be accompanied by other seizure types such as generalised tonic-clonic seizures. In these adult patients, the absence seizures are usually highly disabling, in particular by disqualifying the sufferer from obtaining a motor vehicle license or pursuing occupations and hobbies in which the seizures-associated periods of loss of awareness pose a safety risk, and are associated with significant psychosocial disabilities (Wirrell et al., 1997).

While there is a common perception that absence seizures are relatively "easy" to treat, a randomised control trial in patients with childhood absence epilepsy showed that even the most effective anti-epileptic drugs, ethosuximide and valproate, only completely controlled the seizures in 53% and 58% of patients respectively at 16 weeks as assessed by video-EEG recordings (Glauser et al., 2010), and 45% and 44% respectively at 12 months (Glauser et al., 2013). Lamotrigine, the other AED commonly used to treat absence seizures, only controlled the seizures in 29% of patients at 16 weeks, and 21% of patients at 12 months. Furthermore, both ethosuximide and valproate are commonly associated with intolerable side effects (occurring in 24% of patients treated with either of these drugs) (Glauser et al., 2010), and the latter is now generally considered to be contraindicated in girls and women of childbearing potential. Other treatment options for absence seizures are limited, with only benzodiazepines having established efficacy—and these are commonly poorly tolerated due to sedative and cognitive side effects. Absence seizures persisting into adult life are particularly difficult to treat, with patients often being treated with multiple drugs resulting in significant side-effects without attaining seizure control.

There is abundant evidence that low threshold (T-type) calcium channels play a critical role in the generation and maintenance of absence seizures, being a key component of the oscillatory burst firing that occurs in thalamocortical neurones during absence seizures (Pinault and O'Brien, 1997). In some embodiments, the present invention features a method for treating absence seizures with a composition described herein. In some embodiments, the absence seizures are refractory absence seizures. In some embodiments, the absence seizures are refractory to an anti-epileptic drug (e.g., ethosuximide, valproic acid, or lamotrigine).

In some embodiments, the subject has epilepsy. In some embodiments, the absence seizures are atypical absence seizures. In some embodiments, the absence seizures comprise adult absence seizures, juvenile absence seizures, or childhood absence seizures.

In some embodiments, the methods described herein further comprise identifying a subject having absence seizures.

In another aspect, the present disclosure provides a method of treating a generalized epileptic syndrome with absence seizures in a patient in need thereof, comprising administering to the patient a sufficient amount of the compound of formula (I) or a pharmaceutically acceptable salt thereof (e.g., the compound of formula (II)) that results in reduction of the number of seizures.

Also provided herein is a method of treating a generalized epileptic syndrome with absence seizures in a patient in need thereof, comprising administering to the patient a sufficient amount of the compound of formula (I) or a pharmaceutically acceptable salt thereof (e.g., the compound of formula (II)) that results in reduction of the mean or total seizure duration.

Also provided herein is a method of treating a generalized epileptic syndrome with absence seizures in a patient in need thereof, comprising administering to the patient a sufficient amount of the compound of formula (I) or a pharmaceutically acceptable salt thereof (e.g., the compound of formula (II)) that results in reduction of the seizure frequency, duration or both as measured by Electroencephalogram (EEG).

A contemplated method includes a method of treating a generalized epileptic syndrome with absence seizures in a patient in need thereof, comprising administering to the patient a sufficient amount of the compound of formula (I) or a pharmaceutically acceptable salt thereof (e.g., the compound of formula (II)) that results in reduction of the mean seizure duration as measured by EEG.

Provided herein, in part, is a method of treating a generalized epileptic syndrome with absence seizures in a patient in need thereof, comprising administering to the patient a sufficient amount of the compound of formula (I) or a pharmaceutically acceptable salt thereof (e.g., the compound of formula (II)) that results in reduction of the cumulative seizure duration as measured by EEG.

In one aspect, the present disclosure provides a method of treating a generalized epileptic syndrome with absence seizures in a patient in need thereof, comprising administering to the patient a sufficient amount of the compound of formula (I) or a pharmaceutically acceptable salt thereof (e.g., the compound of formula (II)) that results in reduction of the total time with 2.5-4 Hz spike wave discharges after hyperventilation and photic stimulation challenges as measured by EEG.

A method of treating a generalized epileptic syndrome with absence seizures in a patient in need thereof, comprising administering to the patient a sufficient amount of the compound of formula (I) that results in reduction of global severity as measured by Clinical Global Impression-Severity (CGI-S) or Clinical Global Impression-Improvement (CGI-I) scores is also provided herein. CGI-S is a 7-point scale test to rate the severity of the patient's illness at the time of assessment, relative to the clinician's past experience with patients with the same diagnosis. CGI-I is a 7-point scale test to evaluate the improvement of the patient's illness relative to the baseline.

In another aspect, the present disclosure provides a method of treating a generalized epileptic syndrome with absence seizures in a patient in need thereof, comprising administering to the patient a sufficient amount of the compound of formula (I) or a pharmaceutically acceptable salt thereof (e.g., the compound of formula (II)) that results in reduction of the number of seizures.

Also provided herein is a method of treating a generalized epileptic syndrome with absence seizures in a patient in need thereof, comprising administering to the patient a sufficient amount of the compound of formula (I) or a pharmaceutically acceptable salt thereof (e.g., the compound of formula (II)) that results in reduction of the seizure density as measured by Electroencephalogram (EEG).

A contemplated method includes a method of treating a generalized epileptic syndrome with absence seizures in a patient in need thereof, comprising administering to the patient a sufficient amount of the compound of formula (I) or a pharmaceutically acceptable salt thereof (e.g., the compound of formula (II)) that results in reduction of the mean seizure duration as measured by EEG.

Provided herein, in part, is a method of treating a generalized epileptic syndrome with absence seizures in a patient in need thereof, comprising administering to the patient a sufficient amount of the compound of formula (I) or a pharmaceutically acceptable salt thereof (e.g., the compound of formula (II)) that results in reduction of the cumulative seizure duration as measured by EEG.

In one aspect, the present disclosure provides a method of treating a generalized epileptic syndrome with absence seizures in a patient in need thereof, comprising administering to the patient a sufficient amount of the compound of formula (I) or a pharmaceutically acceptable salt thereof (e.g., the compound of formula (II)) that results in reduction of the total time with 2.5-4 Hz spike wave discharges after hyperventilation and photic stimulation challenges as measured by EEG.

A method of treating a generalized epileptic syndrome with absence seizures in a patient in need thereof, comprising administering to the patient a sufficient amount of the compound of formula (I) that results in reduction of global severity as measured by Clinical Global Impression-Severity (CGI-S) or Clinical Global Impression-Improvement (CGI-I) scores is also provided herein. CGI-S is a 7-point scale test to rate the severity of the patient's illness at the time of assessment, relative to the clinician's past experience with patients with the same diagnosis. CGI-I is a 7-point scale test to evaluate the improvement of the patient's illness relative to the baseline.

In another aspect, the present disclosure provides a method of treating a generalized epileptic syndrome with absence seizures in a patient in need thereof, comprising administering to the patient a sufficient amount of the compound of formula (I) or a pharmaceutically acceptable salt thereof (e.g., the compound of formula (II)) that results in reduction of the number of seizures.

Also provided herein is a method of treating a generalized epileptic syndrome with absence seizures in a patient in need thereof, comprising administering to the patient a sufficient amount of the compound of formula (I) that results in reduction of the seizure density as measured by Electroencephalogram (EEG).

A contemplated method includes a method of treating a generalized epileptic syndrome with absence seizures in a patient in need thereof, comprising administering to the patient a sufficient amount of the compound of formula (I) or a pharmaceutically acceptable salt thereof (e.g., the compound of formula (II)) that results in reduction of the mean seizure duration as measured by EEG.

Provided herein, in part, is a method of treating a generalized epileptic syndrome with absence seizures in a patient in need thereof, comprising administering to the patient a sufficient amount of the compound of formula (I) or a pharmaceutically acceptable salt thereof (e.g., the compound of formula (II)) that results in reduction of the cumulative seizure duration as measured by EEG.

In one aspect, the present disclosure provides a method of treating a generalized epileptic syndrome with absence seizures in a patient in need thereof, comprising administering to the patient a sufficient amount of the compound of formula (I) or a pharmaceutically acceptable salt thereof (e.g., the compound of formula (II)) that results in reduction of the total time with 2.5-4 Hz spike wave discharges after hyperventilation and photic stimulation challenges as measured by EEG.

A method of treating a generalized epileptic syndrome with absence seizures in a patient in need thereof, comprising administering to the patient a sufficient amount of the compound of formula (I) or a pharmaceutically acceptable salt thereof (e.g., the compound of formula (II)) that results in reduction of global severity as measured by Clinical Global Impression-Severity (CGI-S) or Clinical Global Impression-Improvement (CGI-I) scores is also provided herein. CGI-S is a 7-point scale test to rate the severity of the patient's illness at the time of assessment, relative to the clinician's past experience with patients with the same diagnosis. CGI-I is a 7-point scale test to evaluate the improvement of the patient's illness relative to the baseline.

Genetic Epilepsies

In some embodiments, the epilepsy or epilepsy syndrome is a genetic epilepsy or a genetic epilepsy syndrome. In some embodiments, the epilepsy or epilepsy syndrome is genetic generalized epilepsy. In some embodiments, epilepsy or an epilepsy syndrome comprises epileptic encephalopathy, epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, and KCNT1 epileptic encephalopathy.

In some embodiments, the methods described herein further comprise identifying a subject having epilepsy or an epilepsy syndrome (e.g., epileptic encephalopathy, epileptic encephalopathy with SCN1A, SCN2A, SCN8A mutations, early infantile epileptic encephalopathy, Dravet syndrome, Dravet syndrome with SCN1A mutation, generalized Epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, and KCNT1 epileptic encephalopathy) prior to administration of a composition described herein.

In one aspect, the present invention features a method of treating epilepsy or an epilepsy syndrome (e.g., epileptic encephalopathy, epileptic encephalopathy with SCN1A, SCN2A, SCN8A mutations, early infantile epileptic encephalopathy, Dravet syndrome, Dravet syndrome with SCN1A mutation, generalized Epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, and KCNT1 epileptic encephalopathy) comprising administering to a subject in need thereof a composition described herein.

A composition of the present invention may also be used to treat an epileptic encephalopathy, wherein the subject has a mutation in one or more of ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRB3, GABRG2, GNAO1, GOSR2, GRIN1, GRIN2A, GRIN2B, HCN1, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, RELN, SCARB2, SCN1A, SCN1B, SCN2A, SCN8A, SCN9A, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, and WWOX.

In some embodiments, the methods described herein further comprise identifying a subject having a mutation in one or more of ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRB3, GABRG2, GNAO1, GOSR2, GRIN1, GRIN2A, GRIN2B, HCN1, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, RELN, SCARB2, SCN1A, SCN1B, SCN2A, SCN8A, SCN9A, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, WWOX, CACNA1G, CACNA1H, and CACNA1I prior to administration of a composition described herein.

A composition of the present invention may also be used to treat an epileptic encephalopathy, wherein the subject has a mutation in one or more of ADSL, ALDH5A1, ALDH7A1, ALG13, ARG1, ARHGEF9, ARX, ATP1A2, ATP1A3, ATRX, BRAT1, C12orf57, CACNA1A, CACNA2D2, CARS2, CASK, CDKL5, CHD2, CHRNA2, CHRNA4, CHRNB2, CLCN4, CLN2 (TPP1), CLN3, CLN5, CLN6, CLN8, CNTNAP2, CSTB, CTSD, DDC, DEPDC5, DNAJC5, DNM1, DOCK7, DYRK1A, EEF1A2, EFHC1, EHMT1, EPM2A, FARS2, FOLR1, FOXG1, FRRS1L, GABBR2, GABRA1, GABRB2, GABRB3, GABRG2, GAMT, GATM, GLRA1, GNAO1, GOSR2, GRIN1, GRIN2A, GRIN2B, HCN1, HNRNPU, IER3IP1, IQSEC2, ITPA, JMJD1C, KANSL1, KCNA2, KCNB1, KCNC1, KCNH2, KCNJ10, KCNMA1, KCNQ2, KCNQ3, KCNT1, KCTD7, LGI1, LIAS, MBD5, MECP2, MEF2C, MFSD8, MOCS1, MOCS2, MTOR, NEDD4L, NEXMIF, NGLY1, NHLRC1, NPRL3, NRXN1, PACS1, PCDH19, PIGA, PIGN, PIGO, PLCB1, PNKD, PNKP, PNPO, POLG, PPT1, PRICKLE1, PRIMA1, PRRT2, PURA, QARS, RELN, ROGDI, SATB2, SCARB2, SCN1A, SCN1B, SCN2A, SCN3A, SCN8A, SCN9A, SERPINI1, SGCE, SIK1, SLC12A5, SLC13A5, SLC19A3, SLC25A12, SLC25A22, SLC2A1, SLC35A2, SLC6A1, SLC6A8, SLC9A6, SMC1A, SNX27, SPATA5, SPTAN1, ST3GAL5, STRADA, STX1B, STXBP1, SUOX, SYN1, SYNGAP1, SYNJ1, SZT2, TBC1D24, TCF4, TPK1, TSC1, TSC2, UBE3A, WDR45, WWOX, ZDHHC9, ZEB2, ABAT, ARHGEF15, ATP6AP2, CACNA1H, CACNB4, CASR, CERS1, CNTN2, CPA6, DIAPH1, FASN, GABRD, GAL, GPHN, KCNA1, KCND2, KCNH5, KPNA7, LMNB2, NECAP1, PIGG, PIGQ, PIK3AP1, PRDM8, PRICKLE2, RBFOX1, RBFOX3, RYR3, SCN5A, SETD2, SLC35A3, SNAP25, SRPX2, ST3GAL3, TBL1XR1, AMT, GCSH, GLDC, FLNA, PTEN, and RANBP2.

In some embodiments, the methods described herein further comprise identifying a subject having a mutation in one or more of ADSL, ALDH5A1, ALDH7A1, ALG13, ARG1, ARHGEF9, ARX, ATP1A2, ATP1A3, ATRX, BRAT1, C12orf57, CACNA1A, CACNA2D2, CARS2, CASK, CDKL5, CHD2, CHRNA2, CHRNA4, CHRNB2, CLCN4, CLN2 (TPP1), CLN3, CLN5, CLN6, CLN8, CNTNAP2, CSTB, CTSD, DDC, DEPDC5, DNAJC5, DNM1, DOCK7, DYRK1A, EEF1A2, EFHC1, EHMT1, EPM2A, FARS2, FOLR1, FOXG1, FRRS1L, GABBR2, GABRA1, GABRB2, GABRB3, GABRG2, GAMT, GATM, GLRA1, GNAO1, GOSR2, GRIN1, GRIN2A, GRIN2B, HCN1, HNRNPU, IER3IP1, IQSEC2, ITPA, JMJD1C, KANSL1, KCNA2, KCNB1, KCNC1, KCNH2, KCNJ10, KCNMA1, KCNQ2, KCNQ3, KCNT1, KCTD7, LGI1, LIAS, MBD5, MECP2, MEF2C, MFSD8, MOCS1, MOCS2, MTOR, NEDD4L, NEXMIF, NGLY1, NHLRC1, NPRL3, NRXN1, PACS1, PCDH19, PIGA, PIGN, PIGO, PLCB1, PNKD, PNKP, PNPO, POLG, PPT1, PRICKLE1, PRIMA1, PRRT2, PURA, QARS, RELN, ROGDI, SATB2, SCARB2, SCN1A, SCN1B, SCN2A, SCN3A, SCN8A, SCN9A, SERPINI1, SGCE, SIK1, SLC12A5, SLC13A5, SLC19A3, SLC25A12, SLC25A22, SLC2A1, SLC35A2, SLC6A1, SLC6A8, SLC9A6, SMC1A, SNX27, SPATA5, SPTAN1, ST3GAL5, STRADA, STX1B, STXBP1, SUOX, SYN1, SYNGAP1, SYNJ1, SZT2, TBC1D24, TCF4, TPK1, TSC1, TSC2, UBE3A, WDR45, WWOX, ZDHHC9, ZEB2, ABAT, ARHGEF15, ATP6AP2, CACNA1H, CACNB4, CASR, CERS1, CNTN2, CPA6, DIAPH1, FASN, GABRD, GAL, GPHN, KCNA1, KCND2, KCNH5, KPNA7, LMNB2, NECAP1, PIGG, PIGQ, PIK3AP1, PRDM8, PRICKLE2, RBFOX1, RBFOX3, RYR3, SCN5A, SETD2, SLC35A3, SNAP25, SRPX2, ST3GAL3, TBL1XR1, AMT, GCSH, GLDC, FLNA, PTEN, and RANBP2.

A composition of the present invention may also be used to treat an epileptic encephalopathy, wherein the subject has a mutation in one or more of ADSL, ALDH5A1, ALDH7A1, ALG13, ARHGEF9, ARX, ASNS, ATP1A2, ATP1A3, ATP6AP2, ATRX, BRAT1, CACNA1A, CASK, CDKL5, CHD2, CHRNA2, CHRNA4, CHRNA7, CHRNB2, CLCN4, CLN3, CLN5, CLN6, CLN8, CNTNAP2, CSTB, CTNNB1, CTSD (CLN10), CTSF, DDX3X, DEPDC5, DNAJC5 (CLN4B), DNM1, DYRK1A, EEF1A2, EHMT1, EPM2A, FLNA, FOLR1, FOXG1, FRRS1L, GABBR2, GABRA1, GABRB2, GABRB3, GABRG2, GAMT, GATM, GLDC, GNAO1, GOSR2, GRIN1, GRIN2A, GRIN2B, HNRNPU, IQSEC2, KANSL1, KCNA2, KCNB1, KCNC1, KCNH1, KCNJ10, KCNMA1, KCNQ2, KCNQ3, KCNT1, KCTD7 (CLN14), KDM6A, KIAA2022, LGI1, MAGI2, MBD5, MECP2, MEF2C, MFSD8 (CLN7), NALCN, NGLY1, NHLRC1 (EPM2B), NPRL3. NR2F1, NRXN1, PACS1, PCDH19, PIGA PIGO, PIGV, PLCB1, PNKP, PNPO, POLG, PPP2R5D, PPT1 (CLN1), PRRT2, PURA, QARS, SATB2, SCARB2, SCN1A, SCN1B, SCN2A, SCN8A, SLC13A5, SLC19A3, SLC25A22, SLC2A1, SLC6A1, SLC6A8, SLC9A6, SMC1A, SPATA5, SPTAN1, STX1B, STXBP1, SYNGAP1, SZT2, TBC1D24, TBL1XR1, TCF4, TPP1 (CLN2), TSC1, TSC2, UBE3A, WDR45, WWOX, and ZEB2.

In some embodiments, the methods described herein further comprise identifying a subject having a mutation in one or more of ADSL, ALDH5A1, ALDH7A1, ALG13, ARHGEF9, ARX, ASNS, ATP1A2, ATP1A3, ATP6AP2, ATRX, BRAT1, CACNA1A, CASK, CDKL5, CHD2, CHRNA2, CHRNA4, CHRNA7, CHRNB2, CLCN4, CLN3, CLN5, CLN6, CLN8, CNTNAP2, CSTB, CTNNB1, CTSD (CLN10), CTSF, DDX3X, DEPDC5, DNAJC5 (CLN4B), DNM1, DYRK1A, EEF1A2, EHMT1, EPM2A, FLNA, FOLR1, FOXG1, FRRS1L, GABBR2, GABRA1, GABRB2, GABRB3, GABRG2, GAMT, GATM, GLDC, GNAO1, GOSR2, GRIN1, GRIN2A, GRIN2B, HNRNPU, IQSEC2, KANSL1, KCNA2, KCNB1, KCNC1, KCNH1, KCNJ10, KCNMA1, KCNQ2, KCNQ3, KCNT1, KCTD7 (CLN14), KDM6A, KIAA2022, LGI1, MAGI2, MBD5, MECP2, MEF2C, MFSD8 (CLN7), NALCN, NGLY1, NHLRC1 (EPM2B), NPRL3. NR2F1, NRXN1, PACS1, PCDH19, PIGA PIGO, PIGV, PLCB1, PNKP, PNPO, POLG, PPP2R5D, PPT1 (CLN1), PRRT2, PURA, QARS, SATB2, SCARB2, SCN1A, SCN1B, SCN2A, SCN8A, SLC13A5, SLC19A3, SLC25A22, SLC2A1, SLC6A1, SLC6A8, SLC9A6, SMC1A, SPATA5, SPTAN1, STX1B, STXBP1, SYNGAP1, SZT2, TBC1D24, TBL1XR1, TCF4, TPP1 (CLN2), TSC1, TSC2, UBE3A, WDR45, WWOX, and ZEB2.

A composition of the present invention may also be used to treat an epileptic encephalopathy, wherein the subject has a mutation in one or more of ALDH7A1, ARHGEF9, ARX, ATP13A2, ATP1A2, CACNA1A, CASK, CDKL5, CHD2, CHRNA2, CHRNA4, CHRNB2, CLN3, CLN5, CLN6, CLN8, CNTNAP2, CRH, CSTB, CTSD, CTSF, DCX, DEPDC5, DNAJC5, DNM1, DYNC1H1, DYRK1A, EEF1A2, EPM2A, FLNA, FOLR1, FOXG1, GABRA1, GABRB3, GABRG2, GAMT, GATM, GNAO1, GOSR2, GRIN1, GRIN2A, GRIN2B, GRN, HCN1, HNRNPU, IQSEC2, KCNA2, KCNC1, KCNJ10, KCNQ2, KCNQ3, KCNT1, KCTD7, KIAA2022, LGI1, MECP2, MEF2C, MFSD8, NHLRC1, NRXN1, PCDH19, PIGA, PLCB1, PNKP, PNPO, POLG, PPT1, PRICKLE1, PRRT2, PURA, SCARB2, SCN1A, SCN1B, SCN2A, SCN8A, SIK1, SLC13A5, SLC25A22, SLC2A1, SLC35A2, SLC6A1, SLC9A6, SMC1A, SNAP25, SPTAN1, ST3GAL3, STX1B, STXBP1, SYN1, SYNGAP1, SZT2, TBC1D24, TBL1XR1, TCF4, TPP1, TSC1, TSC2, UBE3A, WDR45, and ZEB2.

In some embodiments, the methods described herein further comprise identifying a subject having a mutation in one or more of ALDH7A1, ARHGEF9, ARX, ATP13A2, ATP1A2, CACNA1A, CASK, CDKL5, CHD2, CHRNA2, CHRNA4, CHRNB2, CLN3, CLN5, CLN6, CLN8, CNTNAP2, CRH, CSTB, CTSD, CTSF, DCX, DEPDC5, DNAJC5, DNM1, DYNC1H1, DYRK1A, EEF1A2, EPM2A, FLNA, FOLR1, FOXG1, GABRA1, GABRB3, GABRG2, GAMT, GATM, GNAO1, GOSR2, GRIN1, GRIN2A, GRIN2B, GRN, HCN1, HNRNPU, IQSEC2, KCNA2, KCNC1, KCNJ10, KCNQ2, KCNQ3, KCNT1, KCTD7, KIAA2022, LGI1, MECP2, MEF2C, MFSD8, NHLRC1, NRXN1, PCDH19, PIGA, PLCB1, PNKP, PNPO, POLG, PPT1, PRICKLE1, PRRT2, PURA, SCARB2, SCN1A, SCN1B, SCN2A, SCN8A, SIK1, SLC13A5, SLC25A22, SLC2A1, SLC35A2, SLC6A1, SLC9A6, SMC1A, SNAP25, SPTAN1, ST3GAL3, STX1B, STXBP1, SYN1, SYNGAP1, SZT2, TBC1D24, TBL1XR1, TCF4, TPP1, TSC1, TSC2, UBE3A, WDR45, and ZEB2.

Mood Disorders

Also provided herein are methods for treating a psychiatric disorder such as a mood disorder, for example clinical depression, postnatal depression or postpartum depression, perinatal depression, atypical depression, melancholic depression, psychotic major depression, catatonic depression, seasonal affective disorder, dysthymia, double depression, depressive personality disorder, recurrent brief depression, minor depressive disorder, bipolar disorder or manic depressive disorder, depression caused by chronic medical conditions, treatment-resistant depression, refractory depression, suicidality, suicidal ideation, or suicidal behavior. In some embodiments, the method described herein provides therapeutic effect to a subject suffering from depression (e.g., moderate or severe depression). In some embodiments, the mood disorder is associated with a disease or disorder described herein (e.g., neuroendocrine diseases and disorders, neurodegenerative diseases and disorders (e.g., epilepsy), movement disorders, tremor (e.g., Parkinson's Disease), women's health disorders or conditions).

Clinical depression is also known as major depression, major depressive disorder (MDD), severe depression, unipolar depression, unipolar disorder, and recurrent depression, and refers to a mental disorder characterized by pervasive and persistent low mood that is accompanied by low self-esteem and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and make an individual feel as if life is not worth living.

Peripartum depression refers to depression in pregnancy. Symptoms include irritability, crying, feeling restless, trouble sleeping, extreme exhaustion (emotional and/or physical), changes in appetite, difficulty focusing, increased anxiety and/or worry, disconnected feeling from baby and/or fetus, and losing interest in formerly pleasurable activities.

Postnatal depression (PND) is also referred to as postpartum depression (PPD) and refers to a type of clinical depression that affects women after childbirth. Symptoms can include sadness, fatigue, changes in sleeping and eating habits, reduced sexual desire, crying episodes, anxiety, and irritability. In some embodiments, the PND is a treatment-resistant depression (e.g., a treatment-resistant depression as described herein). In some embodiments, the PND is refractory depression (e.g., a refractory depression as described herein).

In some embodiments, a subject having PND also experienced depression, or a symptom of depression during pregnancy. This depression is referred to herein as perinatal depression. In an embodiment, a subject experiencing perinatal depression is at increased risk of experiencing PND.

Atypical depression (AD) is characterized by mood reactivity (e.g., paradoxical anhedonia) and positivity, significant weight gain or increased appetite. Patients suffering from AD also may have excessive sleep or somnolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt.

Psychotic major depression (PMD) or psychotic depression refers to a major depressive episode, in particular of melancholic nature, where the individual experiences psychotic symptoms such as delusions and hallucinations.

Catatonic depression refers to major depression involving disturbances of motor behavior and other symptoms. An individual may become mute and stuporose, and either is immobile or exhibits purposeless or bizarre movements.

Seasonal affective disorder (SAD) refers to a type of seasonal depression wherein an individual has seasonal patterns of depressive episodes coming on in the fall or winter.

Dysthymia refers to a condition related to unipolar depression, where the same physical and cognitive problems are evident. They are not as severe and tend to last longer (e.g., at least 2 years).

Double depression refers to fairly depressed mood (dysthymia) that lasts for at least 2 years and is punctuated by periods of major depression.

Depressive Personality Disorder (DPD) refers to a personality disorder with depressive features.

Recurrent Brief Depression (RBD) refers to a condition in which individuals have depressive episodes about once per month, each episode lasting 2 weeks or less and typically less than 2-3 days.

Minor depressive disorder or minor depression refers to a depression in which at least 2 symptoms are present for 2 weeks.

Bipolar disorder or manic depressive disorder causes extreme mood swings that include emotional highs (mania or hypomania) and lows (depression). During periods of mania the individual may feel or act abnormally happy, energetic, or irritable. They often make poorly thought out decisions with little regard to the consequences. The need for sleep is usually reduced. During periods of depression there may be crying, poor eye contact with others, and a negative outlook on life. The risk of suicide among those with the disorder is high at greater than 6% over 20 years, while self-harm occurs in 30-40%. Other mental health issues such as anxiety disorder and substance use disorder are commonly associated with bipolar disorder.

Depression caused by chronic medical conditions refers to depression caused by chronic medical conditions such as cancer or chronic pain, chemotherapy, chronic stress.

Treatment-resistant depression refers to a condition where the individuals have been treated for depression, but the symptoms do not improve. For example, antidepressants or psychological counseling (psychotherapy) do not ease depression symptoms for individuals with treatment-resistant depression. In some cases, individuals with treatment-resistant depression improve symptoms, but come back. Refractory depression occurs in patients suffering from depression who are resistant to standard pharmacological treatments, including tricyclic antidepressants, MAOIs, SSRIs, and double and triple uptake inhibitors and/or anxiolytic drugs, as well as non-pharmacological treatments (e.g., psychotherapy, electroconvulsive therapy, vagus nerve stimulation and/or transcranial magnetic stimulation).

Post-surgical depression refers to feelings of depression that follow a surgical procedure (e.g., as a result of having to confront one's mortality). For example, individuals may feel sadness or empty mood persistently, a loss of pleasure or interest in hobbies and activities normally enjoyed, or a persistent felling of worthlessness or hopelessness.

Mood disorder associated with conditions or disorders of women's health refers to mood disorders (e.g., depression) associated with (e.g., resulting from) a condition or disorder of women's health (e.g., as described herein).

Suicidality, suicidal ideation, suicidal behavior refers to the tendency of an individual to commit suicide. Suicidal ideation concerns thoughts about or an unusual preoccupation with suicide. The range of suicidal ideation varies greatly, from e.g., fleeting thoughts to extensive thoughts, detailed planning, role playing, incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, saying goodbye to people as if they won't be seen again.

Symptoms of depression include persistent anxious or sad feelings, feelings of helplessness, hopelessness, pessimism, worthlessness, low energy, restlessness, difficulty sleeping, sleeplessness, irritability, fatigue, motor challenges, loss of interest in pleasurable activities or hobbies, loss of concentration, loss of energy, poor self-esteem, absence of positive thoughts or plans, excessive sleeping, overeating, appetite loss, insomnia, self-harm, thoughts of suicide, and suicide attempts. The presence, severity, frequency, and duration of symptoms may vary on a case to case basis. Symptoms of depression, and relief of the same, may be ascertained by a physician or psychologist (e.g., by a mental state examination).

In some embodiments, the mood disorder is selected from depression, major depressive disorder, bipolar disorder, dysthymic disorder, anxiety disorders, stress, post-traumatic stress disorder, bipolar disorder, and compulsive disorders. In some embodiments, the mood disorder is major depressive disorder.

In some embodiments, the method comprises monitoring a subject with a known depression scale, e.g., the Hamilton Depression (HAM-D) scale, the Clinical Global Impression-Improvement Scale (CGI), and the Montgomery-Asberg Depression Rating Scale (MADRS). In some embodiments, a therapeutic effect can be determined by reduction in Hamilton Depression (HAM-D) total score exhibited by the subject. The therapeutic effect can be assessed across a specified treatment period. For example, the therapeutic effect can be determined by a decrease from baseline in HAM-D total score after administering a composition described herein (e.g., 12, 24, or 48 hours after administration; or 24, 48, 72, or 96 hours or more; or 1 day, 2 days, 14 days, 21 days, or 28 days; or 1 week, 2 weeks, 3 weeks, or 4 weeks; or 1 month, 2 months, 6 months, or 10 months; or 1 year, 2 years, or for life).

In some embodiments, the subject has a mild depressive disorder, e.g., mild major depressive disorder. In some embodiments, the subject has a moderate depressive disorder, e.g., moderate major depressive disorder. In some embodiments, the subject has a severe depressive disorder, e.g., severe major depressive disorder. In some embodiments, the subject has a very severe depressive disorder, e.g., very severe major depressive disorder. In some embodiments, the baseline HAM-D total score of the subject (i.e., prior to treatment with a composition described herein), is at least 24. In some embodiments, the baseline HAM-D total score of the subject is at least 18. In some embodiments, the baseline HAM-D total score of the subject is between and including 14 and 18. In some embodiments, the baseline HAM-D total score of the subject is between and including 19 and 22. In some embodiments, the HAM-D total score of the subject before treatment with a composition described herein is greater than or equal to 23. In some embodiments, the baseline score is at least 10, 15, or 20. In some embodiments, the HAM-D total score of the subject after treatment with a composition described herein is about 0 to 10 (e.g., less than 10; 0 to 10, 0 to 6, 0 to 4, 0 to 3, 0 to 2, or 1.8). In some embodiments, the HAM-D total score after treatment with a composition described herein is less than 10, 7, 5, or 3. In some embodiments, the decrease in HAM-D total score is from a baseline score of about 20 to 30 (e.g., 22 to 28, 23 to 27, 24 to 27, 25 to 27, 26 to 27) to a HAM-D total score at about 0 to 10 (e.g., less than 10; 0 to 10, 0 to 6, 0 to 4, 0 to 3, 0 to 2, or 1.8) after treatment with a composition described herein. In some embodiments, the decrease in the baseline HAM-D total score to HAM-D total score after treatment with a composition described herein is at least 1, 2, 3, 4, 5, 7, 10, 25, 40, or 50). In some embodiments, the percentage decrease in the baseline HAM-D total score to HAM-D total score after treatment with a composition described herein is at least 50% (e.g., 60%, 70%, 80%, or 90%). In some embodiments, the therapeutic effect is measured as a decrease in the HAM-D total score after treatment with a composition described herein relative to the baseline HAM-D total score.

In some embodiments, the method of treating a depressive disorder, e.g., major depressive disorder provides a therapeutic effect (e.g., as measured by reduction in Hamilton Depression Score (HAM-D)) within 14, 10, 4, 3, 2, or 1 days, or 24, 20, 16, 12, 10, or 8 hours or less. In some embodiments, the method of treating the depressive disorder, e.g., major depressive disorder, provides a therapeutic effect (e.g., as determined by a statistically significant reduction in HAM-D total score) within the first or second day of the treatment with a composition described herein. In some embodiments, the method of treating the depressive disorder, e.g., major depressive disorder, provides a therapeutic effect (e.g., as determined by a statistically significant reduction in HAM-D total score) within less than or equal to 14 days since the beginning of the treatment with a composition described herein. In some embodiments, the method of treating the depressive disorder, e.g., major depressive disorder, provides a therapeutic effect (e.g., as determined by a statistically significant reduction in HAM-D total score) within less than or equal to 21 days since the beginning of the treatment with a composition described herein. In some embodiments, the method of treating the depressive disorder, e.g., major depressive disorder, provides a therapeutic effect (e.g., as determined by a statistically significant reduction in HAM-D total score) within less than or equal to 28 days since the beginning of the treatment with a composition described herein. In some embodiments, the therapeutic effect is a decrease from baseline in HAM-D total score after treatment with a composition described herein. In some embodiments, the HAM-D total score of the subject before treatment with a composition described herein is at least 24. In some embodiments, the HAM-D total score of the subject before treatment with a composition described herein is at least 18. In some embodiments, the HAM-D total score of the subject before treatment with a composition described herein is between and including 14 and 18. In some embodiments, the decrease in HAM-D total score after treating the subject with a composition described herein relative to the baseline HAM-D total score is at least 10. In some embodiments, the decrease in HAM-D total score after treating the subject with a composition described herein relative to the baseline HAM-D total score is at least 15. In some embodiments, the HAM-D total score associated with treating the subject with a composition described herein is no more than a number ranging from 6 to 8. In some embodiments, the HAM-D total score associated with treating the subject with a composition described herein is no more than 7.

In some embodiments, the method provides therapeutic effect (e.g., as measured by reduction in Clinical Global Impression-Improvement Scale (CGI)) within 14, 10, 4, 3, 2, or 1 days, or 24, 20, 16, 12, 10, or 8 hours or less. In some embodiments, the CNS-disorder is a depressive disorder, e.g., major depressive disorder. In some embodiments, the method of treating the depressive disorder, e.g., major depressive disorder provides a therapeutic effect within the second day of the treatment period. In some embodiments, the therapeutic effect is a decrease from baseline in CGI score at the end of a treatment period (e.g., 14 days after administration).

In some embodiments, the CNS-disorder is a depressive disorder, e.g., major depressive disorder. In some embodiments, the method of treating the depressive disorder, e.g., major depressive disorder provides a therapeutic effect within the second day of the treatment period. In some embodiments, the therapeutic effect is a decrease from baseline in MADRS score at the end of a treatment period (e.g., 14 days after administration).

A therapeutic effect for major depressive disorder can be determined by a reduction in Montgomery-Asberg Depression Rating Scale (MADRS) score exhibited by the subject. For example, the MADRS score can be reduced within 4, 3, 2, or 1 days; or 96, 84, 72, 60, 48, 24, 20, 16, 12, 10, 8 hours or less. The Montgomery-Åsberg Depression Rating Scale (MADRS) is a ten-item diagnostic questionnaire (regarding apparent sadness, reported sadness, inner tension, reduced sleep, reduced appetite, concentration difficulties, lassitude, inability to feel, pessimistic thoughts, and suicidal thoughts) which psychiatrists use to measure the severity of depressive episodes in patients with mood disorders.

Pain

The dosage forms and compositions described herein may be useful in the treatment of pain. In some embodiments, the pain comprises acute pain, chronic pain, neuropathic pain, inflammatory pain, nociceptive pain, central pain (e.g., thalamic pain), or migraine. In some embodiments, the pain comprises acute pain or chronic pain. In some embodiments, the pain comprises neuropathic pain, inflammatory pain, or nociceptive pain. In some embodiments, the pain comprises central pain (e.g., thalamic pain). In some embodiments, the pain comprises migraine.

In some embodiments, the methods described herein further comprise identifying a subject having pain (e.g., acute pain, chronic pain, neuropathic pain, inflammatory pain, nociceptive pain, central pain (e.g., thalamic pain), or migraine) prior to administration of a dosage form or composition described herein (e.g., a dosage form or composition including a compound of Formula (I) or a pharmaceutically acceptable salt thereof (e.g., the compound of formula (II))).

Tremor

The methods described herein can be used to treat tremor, for example a dosage or composition disclosed herein can be used to treat cerebellar tremor or intention tremor, dystonic tremor, essential tremor, orthostatic tremor, parkinsonian tremor, physiological tremor, or rubral tremor. Tremor includes hereditary, degenerative, and idiopathic disorders such as Wilson's disease, Parkinson's disease, and essential tremor, respectively; metabolic diseases; peripheral neuropathies (associated with Charcot-Marie-Tooth, Roussy-Levy, diabetes mellitus, complex regional pain syndrome); toxins (nicotine, mercury, lead, CO, Manganese, arsenic, toluene); drug-induced (neuroleptics tricyclics, lithium, cocaine, alcohol, adrenaline, bronchodilators, theophylline, caffeine, steroids, valproate, amiodarone, thyroid hormones, vincristine); and psychogenic disorders. Clinical tremor can be classified into physiologic tremor, enhanced physiologic tremor, essential tremor syndromes (including classical essential tremor, primary orthostatic tremor, and task- and position-specific tremor), dystonic tremor, parkinsonian tremor, cerebellar tremor, Holmes' tremor (i.e., rubral tremor), palatal tremor, neuropathic tremor, toxic or drug-induced tremor, and psychogenic tremor. The tremor may be familial tremor.

Tremor is an involuntary, rhythmic, muscle contraction and relaxation that can involve oscillations or twitching of one or more body parts (e.g., hands, arms, eyes, face, head, vocal folds, trunk, legs).

Cerebellar tremor or intention tremor is a slow, broad tremor of the extremities that occurs after a purposeful movement. Cerebellar tremor is caused by lesions in or damage to the cerebellum resulting from, e.g., tumor, stroke or other focal lesion disease (e.g., multiple sclerosis)) or a neurodegenerative disease Dystonic tremor occurs in individuals affected by dystonia, a movement disorder in which sustained involuntary muscle contractions cause twisting and repetitive motions and/or painful and abnormal postures or positions. Dystonic tremor may affect any muscle in the body. Dystonic tremors occur irregularly and often can be relieved by complete rest or certain sensory manuervers.

Essential tremor or benign essential tremor is the most common type of tremor. Essential tremor may be mild and nonprogressive in some, and may be slowly progressive, starting on one side of the body but typically affecting both sides. The hands are most often affected, but the head, voice, tongue, legs, and trunk may also be involved. Tremor frequency may decrease as the person ages, but severity may increase. Heightened emotion, stress, fever, physical exhaustion, or low blood sugar may trigger tremors and/or increase their severity. Symptoms generally evolve over time and can be both visible and persistent following onset.

Orthostatic tremor is characterized by fast (e.g., greater than 12 Hz) rhythmic muscle contractions that occurs in the legs and trunk immediately after standing. Cramps are felt in the thighs and legs and the patient may shake uncontrollably when asked to stand in one spot. Orthostatic tremor may occur in patients with essential tremor.

Parkinsonian tremor is caused by damage to structures within the brain that control movement. Parkinsonian tremor is typically seen as a "pill-rolling" action of the hands that may also affect the chin, lips, legs, and trunk. Onset of parkinsonian tremor typically begins after age 60. Movement starts in one limb or on one side of the body and can progress to include the other side.

Rubral tremor is characterized by coarse slow tremor which can be present at rest, at posture, and with intention. The tremor is associated with conditions that affect the red nucleus in the midbrain, such as a stroke.

In some embodiments, the tremor is selected from essential tremor, Parkinson's tremor, or Cerebellar tremor.

In another aspect, provided herein is a method of treating an essential tremor in a patient in need thereof, comprising administering to the patient a sufficient amount of the compound of formula (I) that results in reduction of the essential tremor as assessed by The Essential Tremor Rating Assessment Scale (TETRAS) score. The term "The Essential Tremor Rating Assessment Scale (TETRAS)" as used herein refers to a scale developed to quantify severity of essential tremor and its impact on daily activities. It has an activities of daily living (ADL) section and a performance section. The ADL section has 12 items rated between 0 to 4, and the performance section has 9 items rated between 0 to 4.

In some embodiments, the reduction of the essential tremor is assessed by The Essential Tremor Rating Assessment Scale (TETRAS) upper limb score.

In some embodiments, the reduction of the essential tremor is assessed by TETRAS performance subscale score or TETRAS performance individual items.

In another aspect, provided herein is a method of treating an essential tremor in a patient in need thereof, comprising administering to the patient a sufficient amount of the compound of formula (I) that results in reduction of the essential tremor as assessed by accelerometer-based score, e.g., accelerometer-based upper limb score.

In some embodiments, the essential tremor is upper limb tremor.

In another aspect, provided herein is a method of treating an essential tremor in a patient in need thereof, comprising administering to the patient a sufficient amount of the compound of formula (I) that results in reduction of the essential tremor as assessed by CGI score.

The efficacy of the compound or composition described herein for treating essential tremor can be measured by the methods described in the following references: Ferreira, J. J. et al., "MDS Evidence-Based Review of Treatments for Essential Tremor." *Mov. Disord.* 2019 July; 34(7):950-958; Elble, R. et al., "Task Force Report: Scales for Screening and Evaluating Tremor." *Mov. Disord.* 2013 November; 28(13): 1793-800. Deuschl G. et al. "Treatment of patients with essential tremor." *Lancet Neurol.* 2011; 10: 148-61. Reich S. G. et al. "Essential Tremor." *Med. Clin. N. Am.* 103 (2019) 351-356. The disclosures of the references are herein incorporated in their entirety.

Ataxia

Ataxia, including both cerebellar ataxia and spinal ataxia (e.g., posterior spinal ataxia), generally involves the loss or failure of coordination. Patients exhibiting ataxia may have difficulty regulating the force, range, direction, velocity, and rhythm involved in posture, balance, and limb movement. Ataxia of the trunk, for example, can result in increased postural sway, and an inability to maintain the center of gravity over the base of support. Ataxia and primary or secondary symptoms of ataxic gait and tremor of the limbs may be accompanied by speech disturbance, dysphagia, abnormal ventilation and speech, and involuntary eye movements, dystonia, pyramidal or extrapyramidal symptoms, thereby substantially interfering with the activities of daily life.

As noted above, ataxia may result from a wide range of underlying diseases and conditions in a patient, including cerebellar and neurodegenerative disorders and diseases resulting from chronic or long-term exposure to toxins. Symptoms of ataxia may result from a wide range of diseases, disorders, and environmental factors, including infectious diseases, metabolic diseases, neurodegenerative diseases, genetic diseases, vascular diseases, neoplastic diseases, demyelinating diseases, neuromuscular diseases, and diseases resulting from long-term or chronic exposure to toxins (including drugs and alcohol), among a variety of others; in one embodiment, for example, the ataxia is the result of a metabolic disease, a neurodegenerative disease, a vascular disease, a neuromuscular disease, or a disease resulting from long-term or chronic exposure to toxins. Diseases, disorders, syndromes, and conditions that may result in ataxic symptoms that may be treated according to the methods described herein include, but are not limited to, amyotrophic lateral sclerosis, benign paroxysmal positional vertigo, cerebellar ataxia type 1 (autosomal recessive), cerebellar ataxias (autosomal recessive), cerebellar ataxias (dominant pure), cerebellar cortical atrophy, cerebellar degeneration (subacute), cerebellar dysfunction, cerebellar hypoplasia, cerebellar hypoplasia (endosteal sclerosis), cerebellar hypoplasia (tapetoretinal degeneration), cerebelloparenchymal autosomal recessive disorder 3, cerebelloparenchymal disorder V, cerebellum agenesis (hydrocephaly), cerebral amyloid angiopathy (familial), cerebral palsy, demyelinating disorder, dorsal column conditions, dysautonomia, dysequilibrium syndrome, dysethesis, endocrine diseases, diseases caused by chronic exposure to toxins (e.g., alcohol, drugs, antiepileptics, neuroleptics), Fragile X/Tremor ataxia syndrome, Friedreich's ataxia, frontal lobe dysfunction, genetic diseases, granulomatous angiitis of the central nervous system, Hallervorden-Spatz disease, hereditary motor and sensory neuropathy, hydrocephalus (e.g., low or normal pressure), hypotonia, congenital nystagmus, ataxia and abnormal auditory brainstem response, infantile onset spinocerebellar ataxia, Machado-Joseph disease, Meniere's disease, metabolic disorders, Miller Fisher Syndrome, Minamata disease, multiple sclerosis, muscular dystrophy, Myoclonus-ataxia, neurodegenerative diseases, olivopontocerebellar atrophy, paraneoplastic disorders, parkinsonism (atypical), peroneal muscular atrophy, phenyloin toxicity, posterior column ataxia with retinitis pigmentosa, post-polio syndrome, severe damage to the brain (caused by, e.g., head injury, brain surgery, multiple sclerosis or cerebral palsy, chronic alcohol/drug abuse, chronic exposure to toxins, viral infections, or brain tumor), spastic hemiparesis, spastic paraplegia 23, spastic paraplegia glaucoma precocious puberty, SPG, spinocerebellar ataxia, spinocerebellar ataxia (amyotrophy—deafness), spinocerebellar ataxia (dysmorphism), spinocerebellar ataxia 11, spinocerebellar ataxia 17, spinocerebellar ataxia 20, spinocerebellar ataxia 25, spinocerebellar ataxia 29, spinocerebellar ataxia 42, spinocerebellar ataxia 3, spinocerebellar ataxia (autosomal recessive 1), spinocerebellar ataxia (autosomal recessive 3), spinocerebellar ataxia (autosomal recessive 4), spinocerebellar ataxia (autosomal recessive 5), spinocerebellar ataxia (autosomal recessive, with axonal neuropathy), spinocerebellar ataxia (Machado-Joseph type II), spinocerebellar ataxia (X-linked, 2), spinocerebellar ataxia (X-linked, 3), spinocerebellar ataxia (X-linked, 4), spinocerebellar degenerescence (book type), stroke (e.g., acute or hemorrhagic), vertebral artery dissection, vertebral-basilar insufficiency, and diseases caused by vitamin deficiencies, among a variety of others. In one embodiment, the ataxia is the result of a disease selected from Spinocerebellar ataxia, Friedriech's ataxia, and fragile X/tremor ataxia syndrome. In another particular embodiment, the ataxia is the result of Spinocerebellar ataxia or fragile X/tremor ataxia syndrome.

Tinnitus

Methods of treating tinnitus in a subject in need thereof using a disclosed dosage form or composition is provided. Tinnitus is a condition in which those affected perceive sound in one or both ears or in the head when no external sound is present. Often referred to as "ringing" in the ears, tinnitus can occur intermittently or consistently with a perceived volume ranging from low to painfully high. However, the perceived volume of tinnitus can vary from patient to patient where an objective measure of tinnitus volume in one patient may be perceived as painful but, in another patient, the same volume may be perceived as subtle.

Sleep Disorders

Methods of treating or preventing sleep disorder (e.g., narcolepsy) using a dosage or composition disclosed herein are provided herein. For example, a sleep disorder may be a central disorder of hypersomnolence, narcolepsy type I, narcolepsy type II, idiopathic hypersomnia, Kleine-Levin syndrome, hypersomnia due to a medical disorder, hypersomnia due to a medication or substance, hypersomnia associated with a psychiatric disorder, insufficient sleep syndrome, circadian rhythm sleep-wake disorders, delayed sleep-wake phase disorder, advanced sleep-wake phase disorder, irregular sleep-wake rhythm, non-24-hour sleep-wake rhythm disorder, shift work disorder, jet lag disorder, circadian rhythm sleep-wake disorder not otherwise specified (NOS).

Combination Therapy

A dosage form or composition described herein (e.g., for use in modulating a T-type calcium ion channel) may be administered in combination with another agent or therapy. A subject to be administered a compound disclosed herein may have a disease, disorder, or condition, or a symptom thereof, that would benefit from treatment with another agent or therapy. These diseases or conditions can relate to epilepsy or an epilepsy syndrome (e.g., absence seizures, juvenile myoclonic epilepsy, or a genetic epilepsy) or tremor (e.g., essential tremor).

Antiepilepsy Agents

Anti-epilepsy agents include brivaracetam, carbamazepine, clobazam, clonazepam, diazepam, divalproex, eslicarbazepine, ethosuximide, ezogabine, felbamate, gabapentin, lacosamide, lamotrigine, levetiracetam, lorazepam, oxcarbezepine, permpanel, phenobarbital, phenytoin, pregabalin, primidone, rufinamide, tigabine, topiramate, valproic acid, vigabatrin, zonisamide.

Analgesics

Analgesics are therapeutic agents that are used to relieve pain. Examples of analgesics include opiates and morphinomimetics, such as fentanyl and morphine; paracetamol; NSAIDs, and COX-2 inhibitors. Given the ability of the compounds of the invention to treat pain via inhibition of T-type calcium channels (e.g., Cav3.1, Cav3.2, and Cav3.3), combination with analgesics are particularly envisioned.

Tremor Medications

Tremor medications include propranolol, primidone, clonazepam, diazepam, lorazepam, alprazolam, gabapentin, topiramate, topamax, neurontin, atenolol, klonopin, alprazolam, nebivolol, carbidopa/levodopa, clonazepam, hydrochlorothiazide/metoprolol, gabapentin enacarbil, labetalol, lactulose, lamotrigine, metoprolol, nadolol, hydrochlorothiazide, and zonisamide.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1: Analysis of Crystallinity of the Compound of Formula (II) by X-Ray Power Diffraction Polymorph screening of the compound of formula (II) was carried out and a stable solid state form (referred to as form C) was identified. Crystallinity of form C was analyzed by X-ray powder diffraction (XRPD).

The XRPD analysis was performed using Bruker D8 ADVANCE and the following conditions.

Bragg Brentano geometry.
2θ range: 3° to 40°.
Step size: 0.02°.
Step time: 0.25 sec.
Slits: 0.3.
Sample rotation on: 15 rpm.
Copper $K_\alpha$ radiation.
Zero background silicon filled sample holder was used.

The powder X-ray diffractogram of form C of the compound of formula (II) is shown in FIG. 1. The positions and relative intensities of the largest 10 peaks of the XRPD pattern of form C are shown in Table 1. The sample is highly crystalline and shows no evidence of any baseline offset indicative of significant amorphicity.

TABLE 1

| XRPD peak list (10 strongest reflections) for form C | | | |
|---|---|---|---|
| Peak | d spacing (Å) | °2θ | % Relative intensity |
| 1 | 3.3 | 26.6 | 100 |
| 2 | 5.5 | 16.2 | 94.2 |
| 3 | 5.1 | 17.4 | 93.5 |
| 4 | 3.9 | 22.6 | 73.8 |
| 5 | 7.7 | 11.5 | 58.6 |
| 6 | 3.7 | 23.9 | 50.8 |
| 7 | 4.8 | 18.3 | 47.5 |
| 8 | 4.6 | 19.2 | 44.7 |

TABLE 1-continued

XRPD peak list (10 strongest reflections) for form C

| Peak | d spacing (Å) | °2θ | % Relative intensity |
|---|---|---|---|
| 9 | 4.8 | 18.5 | 42.4 |
| 10 | 4.4 | 20.0 | 41.1 |

Preparation of Form C

A solution of the free base of the compound of formula (I) was cooled to 0° C. to 10° C. over 1 hour. Ethyl acetate/HCl (10-12%, 53.5 L, prepared in house from ethyl acetate and anhydrous HCl gas) was slowly added to the batch over 30 minutes while maintaining the temperature between 0° C. and 10° C. The batch was warmed to 25° C. to 30° C. over 1.25 hours and was held at this temperature for 4 hours. Vacuum (600-700 mmHg) was applied and the batch was distilled below 33° C. for 6.25 hours at which point the volume of the distillate was 115 L. The batch was cooled to 25° C. to 30° C. and diisopropyl ether (53.5 L, 5 vol.) was added. The batch was held at 25° C. to 30° C. with stirring for 2 hours, then filtered through a Nutsche filter NF202 under nitrogen atmosphere and sucked dry for 30 minutes. The cake was slurry/washed twice with diisopropyl ether (10.7 L, 1 vol) and suck dried for 30 minutes to 1 hour. This material was dried in a vacuum drier VD201 at 65° C. to 70° C. under vacuum (600-650 mmHg) for 12 hours, until the water content of the cake was not more than 2.0 wt %, to give form C of the compound of formula (II) (10.01 kg, 90% yield, 0.45% water by KF).

The polymorph screening identified another stable solid state form (referred to as pattern B). Crystallinity of form B was analyzed by X-ray powder diffraction (XRPD).

The XRPD analysis was performed using Bruker D8 ADVANCE and the same conditions as described above.

The powder X-ray diffractogram for form B of the compound of formula (II) is shown in FIG. 7. The positions and relative intensities of the largest 10 peaks of the XRPD pattern of form C are shown in Table 2. The sample is highly crystalline and shows no evidence of any baseline offset indicative of significant amorphicity.

TABLE 2

XRPD peak list (10 strongest reflections) for form B

| Peak | d spacing (Å) | °2θ | % Relative intensity |
|---|---|---|---|
| 1 | 4.1 | 21.9 | 100 |
| 2 | 4.8 | 18.5 | 61.5 |
| 3 | 5.0 | 17.8 | 53.5 |
| 4 | 8.6 | 10.2 | 49 |
| 5 | 4.3 | 20.5 | 46.1 |
| 6 | 3.5 | 25.2 | 44.1 |
| 7 | 5.3 | 16.9 | 37.7 |
| 8 | 3.7 | 24.2 | 36.5 |
| 9 | 3.1 | 28.6 | 33.9 |
| 10 | 4.2 | 21.2 | 32.4 |

Preparation of Form B
Preparation of Material Showing Diffraction Pattern B from Ethyl Acetate by Controlled Solvent Evaporation Approximately 200 mg of compound of formula (II) was placed in a 30 to 50 mL glass vial/beaker. 20 mL of ethyl acetate was added and the sample was vortex mixed/sonicated for approximately one minute until a clear solution was obtained. The solution was filtered through a syringe filter (Durapore PVDF 0.22 μm centrifuge filter from Millipore) to remove potential seeds of the input solid state form. The solution was then stirred open to the environment at ambient conditions for 48 hours.

Example 2: Thermal Properties of Form C and Pattern B of the Compound of Formula (II)

Form C of the compound of formula (II) was further analyzed by differential scanning calorimetry (DSC), thermogravimetric analysis (TGA), and hot stage microscopy (HSM). The compound has a high melting point and does not undergo any physical or chemical changes below 180° C.

DSC

The DSC of form C of the compound of formula (II) was analyzed using Perkin Elmer Diamond DSC and the following conditions.

Aluminum pans under nitrogen purge gas.
Sample size: 1 to 5 mg.
Temperature range: 25° C. to 250° C.
Heating rate: 2° C./min, 5° C./min, 10° C./min.

The DSC thermogram for form C of the compound of formula (II) is shown in FIG. 2. A summary of the data obtained in shown in Table 3. The obtained thermogram shows a single sharp endotherm with an onset temperature of 226.6° C. due to melting of form C.

TABLE 3

DSC data obtained for form C of the compound of formula (II)

| Parameter | Event 1 (endothermic) |
|---|---|
| onset temp (° C.) | 226.6 |
| peak temp (° C.) | 230.9 |
| ΔH (J/g) | 101.8 |

TGA

The TGA analysis was conducted using perkin elmer Pyris 1 and the following conditions.

Platinum pan under nitrogen purge gas.
Sample size: 2 to 4 mg.
Temperature range: ambient to 300° C.
Heating rate: 10° C./min.

Figure 3:
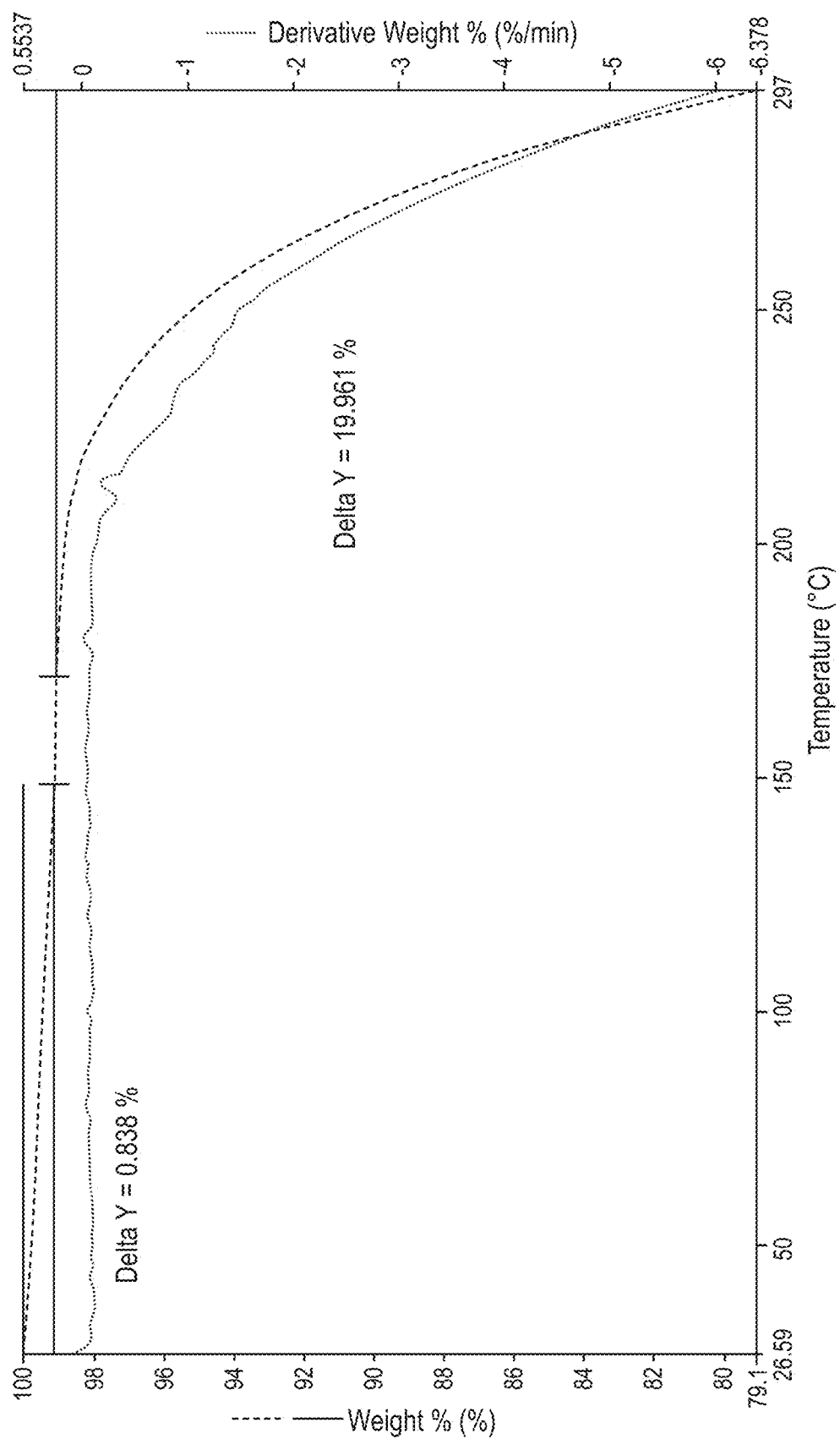
FIG. 3 is a thermogravimetric analysis (TGA) thermogram of form C of the compound of formula (II).

The TGA thermogram (FIG. 3) shows weight loss of approximately 0.8% w/w when heating from ambient to 150° C., indicating that form C of the compound of formula (II) is not a hydrate or solvate (the theoretical weight loss for monohydrate is 4.1% w/w).

TABLE 4

TGA data obtained for form C of the compound of formula (II)

| Event | Weight loss |
|---|---|
| 1 | 0.8% w/w (ambient to 150° C.) |
| 2 | 20.0% w/w (175° C. to 300° C.) |

HSM

Figure 4:
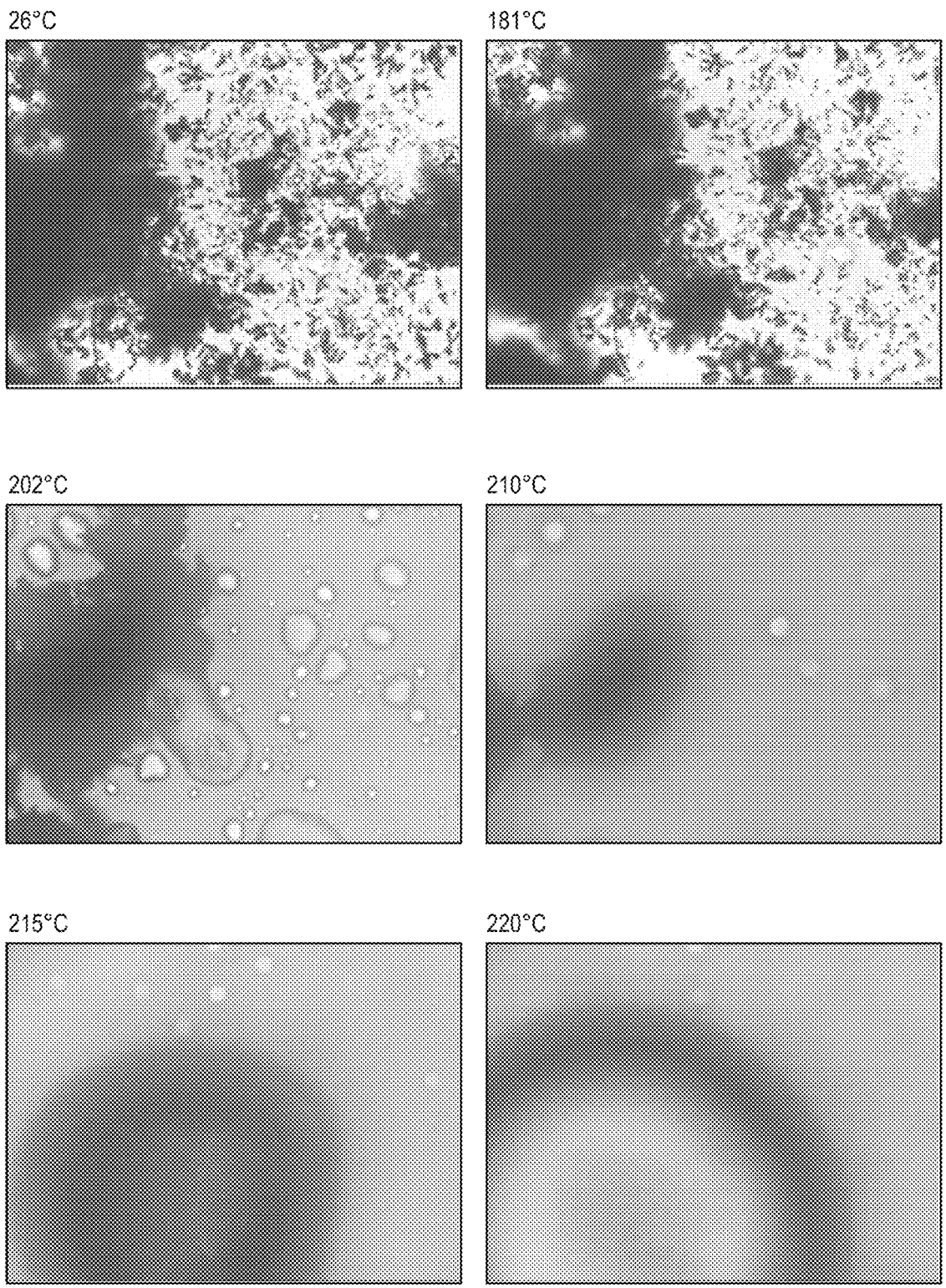
FIG. 4 is a hot stage microscopy (HSM) photomicrographs of form C of the compound of formula (II).

The HSM on form C of the compound of formula (II) was conducted at ambient temperature to 300° C. (no sample equilibrium) with 10° C./min or 20° C./min heating rate. FIG. 4 shows the HSM photomicrographs of form C of the compound of formula (II). The experiment confirmed that the material remained unchanged up to approximately 180° C. The material began to melt at approximately 201° C. and the melt of the final particle was complete at approximately 215° C. The endothermic event seen in the DSC thermogram with an onset temperature of 227° C. corresponded to the melt. Pattern B of the compound of formula (II) was further analyzed by differential scanning calorimetry (DSC), thermogravimetric analysis (TGA), and hot stage microscopy (HSM).

The DSC thermograms for Pattern B material at heating rates of 10° C./min and 2° C./min are shown in FIG. 8. A summary of the data obtained is shown in Table 4. The DSC thermogram with heating rate 10° C./min showed three endothermic events. The first endotherm with an onset temperature of approximately 98° C. can be assigned to the weight loss event seen in the TGA experiment (75° C. to 125° C.) likely to be due to water or solvent loss. A slower heating rate of 2° C./min was used to investigate the thermal events seen at higher temperatures. The DSC thermogram recorded with heating rate 2° C./min obtained shows four major events, three endothermic and one exothermic events. The first endothermic event (onset temperature 84° C.) is likely to be due to water or solvent loss. The second event (onset temperature 129° C.) due to melting of the dehydrated or desolvated form of the compound. An exothermic event (onset temperature 169° C.) was observed following this melt which corresponded to crystallisation seen in HSM (likely to give Pattern C material). The final endothermic event (onset temperature 224° C.) was shown to be a melt by HSM and corresponds to the melt of Pattern C material.

TABLE 4

DSC data obtained for pattern B of the compound of formula (II)

10° C./min heating rate

| Parameter | Event 1 (endothermic) | Event 2 (endothermic) | Event 3 (endothermic) |
|---|---|---|---|
| Onset temperature (° C.) | 97.9 | 131.6 | 223.7 |
| Peak temperature (° C.) | 117.1 | 139.9 | 226.6 |
| ΔH (J/g) | 111.3 | 14.0 | 2.3 |

2° C./min heating rate

| Parameter | Event 1 (endothermic) | Event 2 (endothermic) | Event 3 (exothermic) | Event 4 (endothermic) |
|---|---|---|---|---|
| Onset temperature (° C.) | 83.8 | 128.9 | 168.9 | 224.4 |
| Peak temperature (° C.) | 99.1 | 133.9 | 184.6 | 226.5 |
| ΔH (J/g) | 134.0 | 37.5 | −43.2 | 61.6 |

Figure 9:
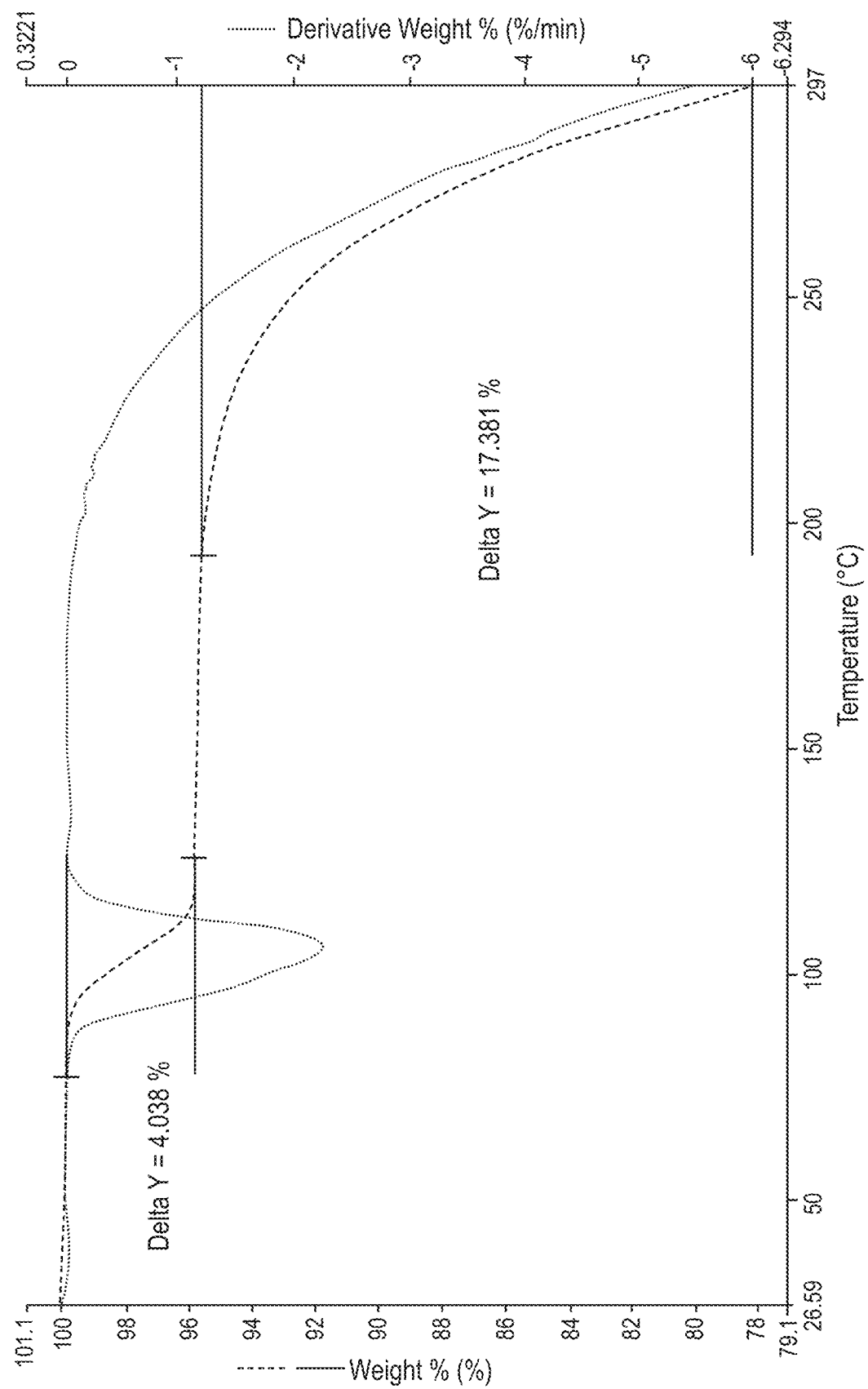
FIG. 9 is a thermogravimetric analysis (TGA) thermogram of pattern B of the compound of formula (II).

The TGA thermogram for Pattern B material is shown in FIG. 9. A summary of the data obtained is shown in Table 5. The TGA thermogram shows a step-wise weight loss typical of hydrates of approximately 4.0% w/w over the temperature range 75° C. to 125° C. The theoretical weight for a monohydrate is 4.1%; indicating that Pattern B is a possible hydrate. It is not likely to be a solvate as it comes from different solvents and different solvates are unlikely to give the same diffraction pattern. This weight loss event, corresponds to first endotherm observed in the DSC thermogram. A significant weight loss of approximately 17% w/w was observed over a temperature range of 195° C. to 300° C. Examination of the residue from the experiment showed it to be a brown mass, indicating degradation had occurred. Hot stage microscopy confirmed a melt at approximately 200° C. followed by decomposition.

TABLE 5

TGA data obtained for pattern B of the compound of formula (II)

| Event | Weight loss |
|---|---|
| 1 | 4.0% w/w (75° C. to 125° C.) |
| 2 | 17.4% w/w (195° C. to 300° C.) |

Figure 10:
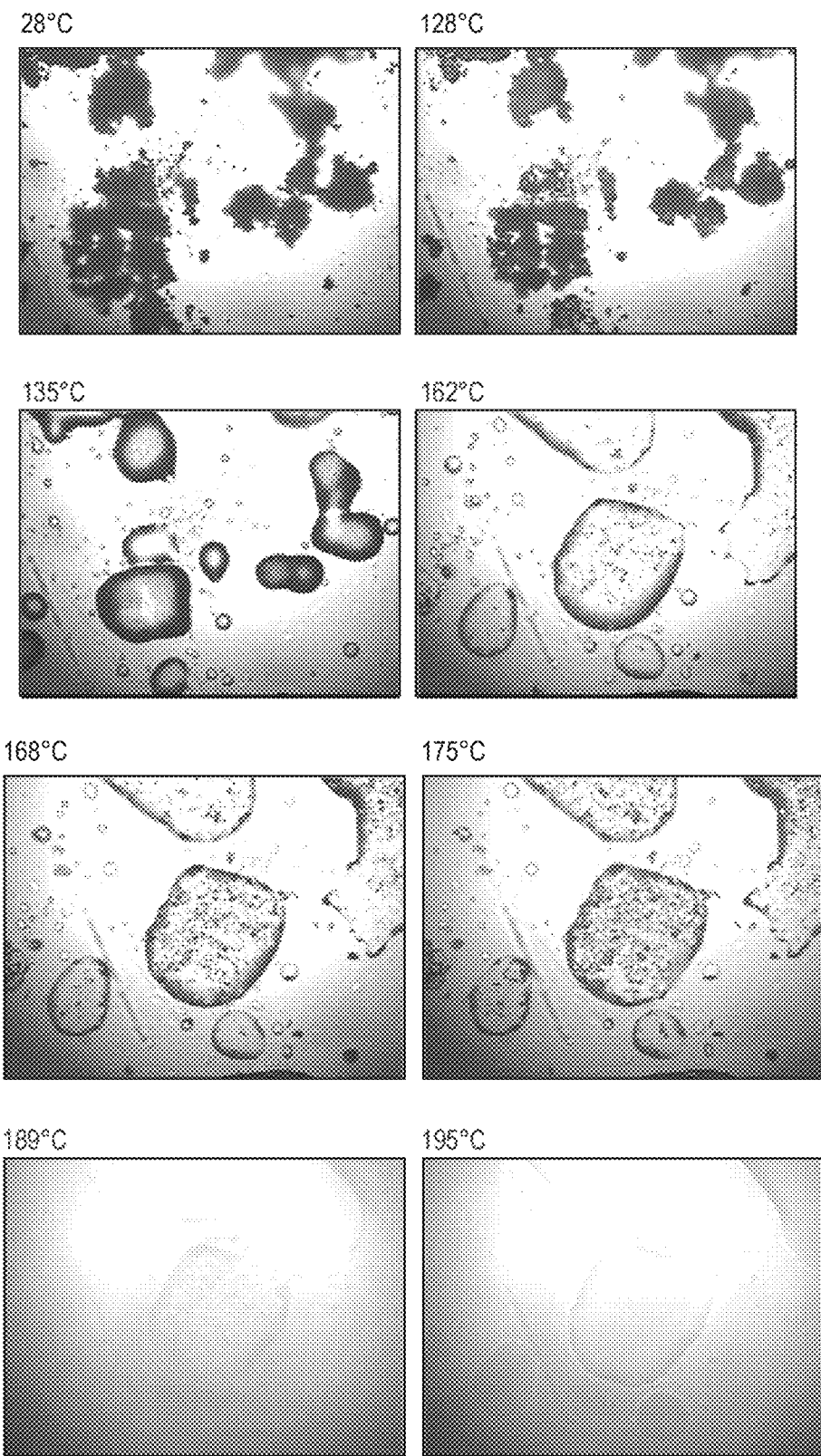
FIG. 10 is a hot stage microscopy (HSM) photomicrographs of pattern B of the compound of formula (II).

HSM on Pattern B material showed the appearance of the material to be unchanged up to a temperature of 128° C. The material began to melt at 128° C. and the melt of the final particle was complete at a temperature of approximately 135° C. (see FIG. 10). This confirms the event with an onset temperature of 227° C. observed in DSC was due to a melt. Recrystallization from the melt was observed between 161° C. to 175° C., while change in the colour of the melt was observed concurrently with the melting of the recrystallized solid between 189° C. to 195° C.

Degradation of the compound may occur differently during HSM when compared to DSC. HSM is carried out under an atmosphere of air; DSC is carried out under an inert atmosphere of nitrogen. Therefore oxidative processes may occur during HSM which will not occur during DSC.

Example 3: Modified Release Tablet Formulations of the Compound of Formula (II)

Formulations

In a Phase 1, single-, ascending-dose study of immediate-release ("IR") capsules central nervous system (CNS)-related events and psychiatric-related adverse events were the most commonly reported adverse events and typically occurred around the time of maximum plasma concentrations (Tmax). In a subsequent cohort within the same study, administration of 40 mg of IR capsules as four 10-mg doses at 2-hour intervals reduced the mean Cmax value by ~50% of the value that was observed after administration of a single, oral 40-mg dose of the compound of formula (II) and mild headache and mild somnolence were the only adverse events that were reported after the split dose. Given these findings, modified-release ("MR") tablet formulations of the compound of formula (II) were developed in an attempt to reduce the Cmax of a given dose, while maintaining the overall AUC.

The composition of the immediate release capsule of the compound of formula (II) is provided in Table 6 below.

TABLE 6

Formulation of the compound of formula (II) for immediate release capsules

| Ingredients | Formulation |
|---|---|
| the compound of formula (II) (HCl salt, form C) | 20.00 mg |
| Hypromellose | 5.50 mg |
| Microcrystalline cellulose | 41.35 mg |
| Mannitol | 39.30 mg |
| Croscarmellose sodium | 2.75 mg |
| Magnesium stearate | 1.10 mg |
| Opaque white size# 4 hard gelatin capsules | 1 each |
| Total weight | 110 mg |

Three initial tablet formulations of the compound of formula (II) (form C) with different release rate profiles were prepared: formulation 1 (about 80% of the compound of formula (I) is released within 2 hours after an administration to a subject), formulation 2 (80% release rate of 5 hours), and formulation 3 (80% release rate of 7 hours). The compositions of the formulations are shown in Table 7. Each tablet contains 20 mg of the compound of formula (II).

TABLE 7

Formulation of the compound of formula (II) for modified release tablets

| Ingredients | Formulation 1 (80% release rate of 2 hours) | Formulation 2 (80% release rate of 5 hours) | Formulation 3 (80% release rate of 7 hours) |
| --- | --- | --- | --- |
| the compound of formula (II) (form C) | 20.00 mg | 20.00 mg | 20.00 mg |
| Microcrystalline cellulose | 28.75 mg | 18.75 mg | 19.50 mg |
| Mannitol | 28.75 mg | 18.75 mg | 0 mg |
| Hypromellose | 20.00 mg | 40.00 mg | 58.00 mg |
| Colloidal silicon dioxide | 1.50 mg | 1.50 mg | 1.50 mg |
| Magnesium stearate | 1.00 mg | 1.00 mg | 1.00 mg |
| Opadry white 03K580000 | 3.00 mg | 3.00 mg | 3.00 mg |
| Total weight | 103.00 mg | 103.00 mg | 103.00 mg |

Manufacturing Process

The process to prepare the modified release tablets consists of 6 sequential steps: 1) sifting of all ingredients (the compound of formula (I) or a pharmaceutically acceptable salt thereof, e.g., formula (II), and excipients), 2) blending of the compound of formula (I) or a pharmaceutically acceptable salt thereof, e.g., the compound of formula (II) with excipients (including intra granular lubrication), 3) roller compaction (including milling), 4) extra granular lubrication, 5) tablet compression, and 6) tablet coating.

Example 4: Pharmacokinetic Studies of the Modified Release Tablets

Modified release tablets of the compound of formula (II) were developed in an attempt to mitigate some of the adverse effects seen with immediate release capsules of the compound of formula (II). The reduction in $C_{max}$ and the delay in $t_{max}$ of three modified release tablet formulations of the compound of formula (II), relative to the immediate release capsule formulation of the compound of formula (II), were evaluated under fasting conditions in healthy volunteers in a Phase 1 study.

The Phase 1 study was a randomized, open-label, 4-way crossover study. Eligible subjects were randomized to 1 of 4 treatment sequences and received single 20-mg doses (the compound of formula (II)) of the immediate release capsule formulation of the compound of formula (II) and single 20-mg doses of the following 3 modified release tablet formulations of the compound of formula (II) in the fasted state: formulation 1 (80% release rate within 2 hours), formulation 2 (80% release rate within 5 hours), and formulation 3 (80% release rate within 7 hours). Study treatments were administered at 4 separate study visits each of which was separated from the previous one by a minimum 1-week washout period.

Figure 5:
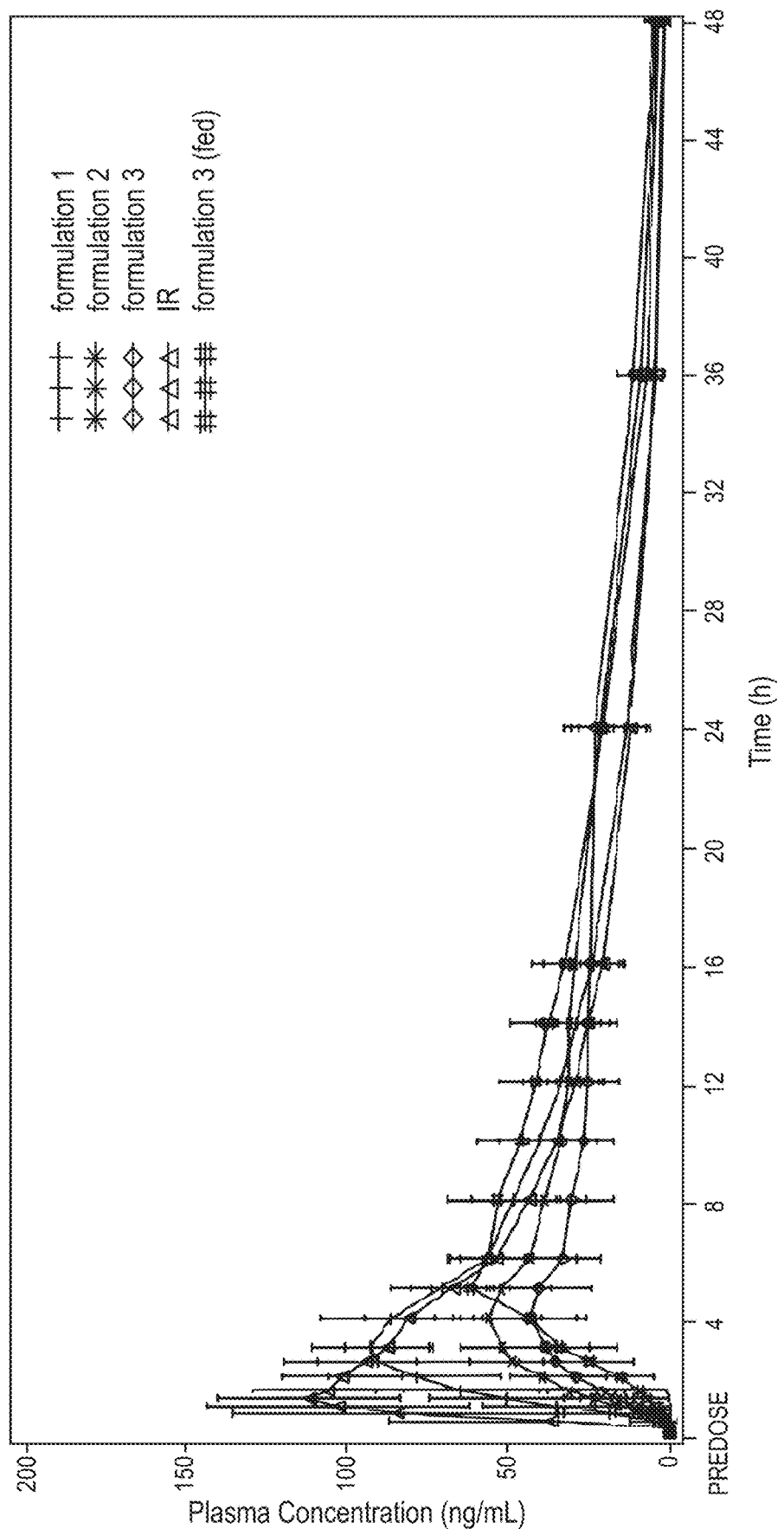
FIG. 5 is a graph showing mean concentration-time profiles of the compound of formula (I) after single 20 mg oral doses of the modified-release tablets and immediate-release capsule of the compound of formula (II).

FIG. 5 shows mean concentration-time profiles of the compound of formula (I), after single 20-mg oral doses of the modified-release tablets and immediate-release capsule of the compound of formula (II).

After administration of 20 mg of the compound of formula (II) in the fasted state, plasma concentrations of the compound of formula (I) were quantifiable by 0.75 hours after administration of each of the modified release tablet formulations of the compound of formula (II) and after administration of the immediate release capsule formulation in the fasted state (FIG. 5). After reaching $C_{max}$, plasma concentrations of the compound of formula (I) declined in a biphasic manner after administration of both the immediate release capsule and formulation 1 tablet in the fasted state. Plasma concentrations plateaued after reaching $C_{max}$ and then declined in a monophasic manner after administration of formulation 2 and formulation 3 tablets in the fasted state. The compound of formula (I) remained quantifiable for a minimum of 36 hours after administration of the immediate release capsule and formulation 1 tablet, and for the duration of the 48-hour sampling period after administration of formulation 2 and formulation 3 tablets.

The formulation 3 tablet in the fed state had declining plasma concentrations in a biphasic manner after reaching $C_{max}$. The compound of formula (I) remained quantifiable for the duration of the 48-hour sampling period after administration of the formulation 3 tablet in the fed states. (FIG. 5).

Table 8 summarizes the median $t_{max}$, the observed geometric mean $C_{max}$, the observed geometric mean $AUC_{last}$, and the $AUC_{inf}$ for the immediate release capsule, formulation 1 tablet (release rate of 2 hours), formulation 2 tablet (release rate of 5 hours), and formulation 3 tablet (release rate of 7 hours). The modified release formulations with longer release rates providing delayed $t_{max}$ values and reduced $C_{max}$ concentrations relative to the immediate release capsule while maintaining overall exposure as assessed by $AUC_{last}$. The observed $t_{1/2}$ was similar for all formulations at approximately 8 to 10 hours. There was no evidence to suggest that the rate of absorption influenced $t_{1/2}$. Intra-subject variability associated with $AUC_{last}$ was similar amongst the three modified release tablet formulations.

TABLE 8

Geometric mean values (CV % geometric mean) of pharmacokinetic parameters of the compound of formula (II) after single oral 20 mg doses of modified-release tablets and immediate-release capsule (Study Phase 1)

| | Modified Release Tablet Formulation | | | Immediate |
| --- | --- | --- | --- | --- |
| Parameter | Formulation 1 [Fasted] (N = 18) | Formulation 2 [Fasted] (N = 18) | Formulation 3 [Fasted] (N = 18) | Release Capsule [Fasted] (N = 18) |
| $t_{lag}$ (h)[1] | 0.250 (0.00-0.52) | 0.250 (0.25-0.50) | 0.250 (0.25-0.50) | 0.250 (0.00-0.50) |
| $t_{max}$ (h)[1] | 3.000 (1.50-5.00) | 4.000 (1.50-5.00) | 4.000 (2.50-24.00) | 1.250 (0.50-3.15) |
| $C_{max}$ (ng/mL) | 95.1 (25.4) | 56.4 (27.6) | 44.5 (35.9) | 127 (26.5) |
| $AUC_{last}$ (ng * h/mL) | 1020 (31.4) | 1010 (29.4) | 910 (29.9) | 1040 (24.0) |
| $AUC_{inf}$ (ng * h/mL) | 1050 (32.1) | 1050 (31.2) | 961 (35.1) | 1060 (24.9) |

TABLE 8-continued

Geometric mean values (CV % geometric mean) of pharmacokinetic parameters of the compound of formula (II) after single oral 20 mg doses of modified-release tablets and immediate-release capsule (Study Phase 1)

| | Modified Release Tablet Formulation | | | Immediate Release Capsule [Fasted] (N = 18) |
|---|---|---|---|---|
| Parameter | Formulation 1 [Fasted] (N = 18) | Formulation 2 [Fasted] (N = 18) | Formulation 3 [Fasted] (N = 18) | |
| $AUC_{extrap}$ (%) | 1.91 (64.1) | 4.18 (42.7) | 5.71 (57.5) | 1.81 (51.1) |
| t½ (h) | 8.146 (18.5) | 9.349 (13.2) | 10.059 (15.2) | 7.948 (17.7) |
| Cl/F (mL/h) | 319 (32.1) | 317 (31.2) | 347 (35.1) | 315 (24.9) |
| $V_z/F$ (mL) | 225 (25.3) | 256 (25.8) | 302 (29.1) | 217 (16.2) |

Abbreviations: $AUC_{extrap}$, percentage of the area extrapolated beyond the last quantifiable plasma concentration; $AUC_{inf}$, area under the plasma concentration-time curve from time of dosing to infinity; $AUC_{last}$, area under the plasma concentration-time curve from time of dosing to the last measurable concentration; $C_{max}$, maximum (peak) plasma drug concentration; CV %, coefficient of variation expressed as a percentage; t½, terminal elimination half-life; M = modified-release, $t_{lag}$, time prior to the first measurable (non-zero) concentration; $t_{max}$, time to reach maximum (peak) plasma drug concentration; $V_z/F$, apparent volume of distribution after oral administration.
[1]Median (range).

Of the 18 subjects who received single, oral 20-mg doses of the 3 modified release tablet formulations (formulations 1-3) or the IR capsule (see Example 4) in the fasted state, 17 subjects (94.4%) experienced at least one adverse event after administration of any of the formulations (Table 9). At least one drug-related adverse event was reported in 15 of the 18 subjects (83.3%). No severe or serious adverse events were reported, and none of the subjects discontinued treatment with the study drug because of adverse events.

Consistent with the expected lower Cmax exposure of the compound of formula (I) for the MR tablets relative to the IR capsule, the percentage of subjects who experienced at least one adverse event and the percentage of subjects who experienced at least one drug-related adverse event were fewer after administration of each of the MR tablets than after administration of the IR capsule (Table 9). Among the MR tablets, the percentage of subjects who experienced any adverse event and the percentage of subjects who experienced any drug-related adverse event were smallest for the formulation 3:

At least one adverse event was reported in 33.3% of the subjects after administration of the formulation 3 tablet, in 44.4% of the subjects after administration of the formulation 2, in 61.1% after administration of the formulation 1 tablet, and in 72.2% of the subjects after administration of the IR capsule.

At least one drug-related adverse event was reported in 16.7% of the subjects after administration of the formulation 3, in 44.4% of the subjects after administration of the formulation 2, in 44.4% after administration of the formulation 1, and in 72.2% of the subjects after administration of the IR capsule.

The increase in percentage of subjects who experienced any adverse event and any drug-related adverse event was concentration dependent and, in general, correlated with the ordering of Cmax (formulation 3<formulation 2<formulation 1<IR capsule)"

TABLE 9

Overall Summary of Treatment-Emergent Adverse Events After Single Oral 20-mg Doses of Tablets (formulations 1-3) and Immediate-Release Capsule in Fasted State (Safety Population)

| | MR Tablet Formulation | | | IR | All |
|---|---|---|---|---|---|
| Number (%) of Subjects With | Formulation 1 (N = 18) n (%) | Formulation 2 (N = 18) n (%) | Formulation 3 (N = 18) n (%) | Capsule (N = 18) n (%) | Formulations (N = 18) n (%) |
| At least one TEAE | 11 (61 1) | 8 (44 4) | 6 (33 3) | 13 (72 2) | 17 (94.4) |
| At least one drug-related TEAE[1] | 8 (44 4) | 8 (44 4) | 3 (16.7) | 13 (72.2) | 15 (83.3) |
| With at least one severe TEAE | 0 | 0 | 0 | 0 | 0 |
| With at least one SAE | 0 | 0 | 0 | 0 | 0 |
| With at least one TEAE leading to discontinuation of study drug | 0 | 0 | 0 | 0 | 0 |

Abbreviations: IR = immediate release, MR = modified release, SAE = serious adverse event, TEAE treatment-emergent adverse event

[1]Drug-related adverse events are those for which the investigator assessed the relationship to the study drug as possible, probable, or certain. Source

Example 5: Pharmacokinetic Studies of the Modified Release Tablets

This was a 2-part, Phase 1 double blind, placebo controlled trial to assess the safety, tolerability, PK, and PD (including the KSS, the KDT, the SQSQ and 24-hour EEG recordings), of single, ascending (Part A: 20, 40, and 60 mg)) and multiple, ascending (Part B: 20 and 40 mg for 8 days) doses of the 20 mg tablet (formulation 3) in healthy participants. Based on the results of this trial, following single oral doses of the 20 mg tablet formulation (formulation 3), exposure to the compound of formula (I) increased with dose over the dose range from 20 mg to 60 mg. Variability in Cmax and AUC increased with increasing dose following a single oral dose of the 20 mg tablet formulation (formulation 3).

In this study, single and multiple (daily for 8 days) doses of 20 and 40 mg were well tolerated. A single 60 mg administered to 6 healthy volunteers was not tolerated. 5 of the 6 participants were nauseated and 3 of the 6 participants vomited.

TABLE 10

Geometric Mean Values (Geometric CV %) After Single Oral Doses of 20 mg Tablet Formulation 3 (Part A)

| | Dose group | | |
|---|---|---|---|
| Parameter | 20 mg [20 mg formulation 3 Tablet × 1] (N = 6) | 40 mg [20 mg formulation 3 Tablet × 2] (N = 6) | 60 mg [20 mg formulation 3 Tablet × 3] (N = 6) |
| $t_{lag}$ (h)[1] | 0.250 (0.25-0.50) | 0.250 (0.25-0.75) | 0.250 (0.25-0.25) |
| $t_{max}$ (h)[1] | 8.50 (2.0-24.0) | 3.50 (3.0-5.0) | 5.50 (5.0-14.0) |
| $C_{max}$ (ng/mL) | 39.8 (13.0) | 85.8 (32.0) | 130 (59.3) |
| $AUC_{last}$ (ng * h/mL) | 853 (16.8) | 1730 (29.0) | 2570 (44.6) |
| $AUC_{24}$ (ng * h/mL) | 578 (14.2) | 1210 (30.5) | 1910 (42.9) |
| $AUC_{inf}$ (ng * h/mL) | 887 (19.3)[2] | 1840 (30.5) | 2470 (43.9)[2] |
| $t_{1/2}$ (h) | 5.034 (104.1)[2] | 5.282 (39.7) | 3.299 (136.4)[2] |
| Cl/F (mL/min) | 9.518 (28.4)[2] | 9.334 (18.9) | 10.246 (56.9) |
| $V_z/F$ (L) | 376 (19.3)[2] | 363 (30.5) | 405 (43.9)[2] |

$AUC_{24}$ = area under the plasma concentration-time curve from time of dosing to 24 hours after dosing, $AUC_{inf}$ = area under the plasma concentration-time curve from time of dosing to infinity, $AUC_{last}$ = area under the plasma concentration-time curve from time of dosing to the last measurable concentration, $C_{max}$ = maximum (peak) plasma drug concentration, CL/F = apparent total clearance of the drug from plasma after oral administration, CV % = percent coefficient of variation, % $AUC_{extrap}$ = area under the plasma concentration-time curve extrapolated from time t to infinity as a percentage of the total area under the curve, MR = modified-release, $t_{1/2}$ = elimination half-life, $t_{lag}$ = lag time, $t_{max}$ = time of maximum (peak) plasma drug concentration, $V_z/F$ = apparent volume of distribution during terminal phase after oral administration.
[1]Median (range).
[2]n = 5.

Pharmacokinetic properties of multiple 20 and 40 mg doses of the 20 mg tablet (formulation 3) were determined on day 1 and 8 of dosing (Table 11). Based on the results of this trial, following once daily dosing with the 20 mg tablet formulation for 8 days, exposure to the compound of formula (II) increased with dose over the dose range of 20 to 40 mg. Variability in Cmax and AUC increased somewhat within the dose range studied. Steady state was achieved by day 5 of repeated daily dosing over the dose range 20 to 40 mg. An approximately 2 fold increase in Cmax was observed over the 8 days of dosing.

TABLE 11

Geometric Mean Values (Geometric CV %) of Plasma Pharmacokinetic Parameters After Single and Multiple Oral Doses of 20 mg Tablet Formulation (formulation 3) (Part B)

| | Dose group | | | |
|---|---|---|---|---|
| | 20 mg [20 mg Tablet x 1 (formulation 3)] (N = 6) | | 40 mg [mg Tablet x 2 (formulation 3)] (N = 6) | |
| Parameter | Day 1 | Day 8 | Day 1 | Day 8 |
| $t_{lag}$ (h)[1] | 0.250 (0.25-0.25) | 0.00 (0.00-0.00) | 0.250 (0.25-0.50) | 0.00 (0.00-0.00) |
| $t_{max}$ (h)[1] | 14.000 (5.00-23.92) | 1.500 (1.25-3.00) | 2.750 (1.50-12.00) | 1.750 (1.50-5.00) |
| $C_{max}$ (ng/mL) | 38.5 (22.6) | 66.5 (25.2) | 70.3 (37.9) | 138 (47.1) |
| $C_{min,ss}$ (ng/mL) | NA | 34.6 (27.6) | NA | 55.3 (49.0) |
| $C_{avg,ss}$ (ng/mL) | NA | 46.8 (27.2) | NA | 86.1 (46.4) |
| $AUC_{\tau,ss}$ (ng · h/mL)[2] | 689 (27.2) | 1120 (27.2) | 1050 (44.0) | 2070 (46.4) |
| $t_{1/2,ss}$ (h) | NC | 10.545 (16.5) | NA | 9.956 (14.4) |
| $Cl/F_{ss}$ (mL/min) | NA | 297 (27.2) | NA | 322 (46.4) |
| $V_z/F_{ss}$ (L) | NA | 271 (21.3) | NA | 278 (33.2) |
| Fluctuation (%) | NA | 67.369 (15.4) | NA | 94.771 (21.1) |
| Rac AUC | NA | 1.631 (25.0) | NA | 1.961 (22.4) |
| Rac $C_{max}$ | NA | 1.729 (20.1) | NA | 1.967 (22.6) |

Abbreviations: $AUC_{24}$ = area under the plasma concentration-time curve from time of dosing to 24 hours after dosing, $AUC_\tau$ = area under the plasma concentration-time curve during a dosing interval, $C_{avg}$ = average drug concentration during multiple dose administration, $C_{max}$ = maximum (peak) plasma drug concentration, $C_{min}$ = minimum plasma drug concentration, CL/F = apparent total clearance of the drug from plasma after oral administration, CV % = percent coefficient of variation, MR = modified-release, NA = not applicable, NC = not calculated, Rac AUC = accumulation ratio calculated from $AUC_{\tau,ss}$ and $AUC_\tau$, Rac $C_{max}$ = accumulation ratio calculated from $C_{max,ss}$, ss = steady state, $t_{1/2}$ = elimination half-life, $t_{lag}$ = lag time, $t_{max}$ = time of maximum (peak) plasma drug concentration, $V_z/F$ = apparent volume of distribution during terminal phase after oral administration.
[1]Median (range).
[2]Labeled as $AUC_{24}$ on day 1

The T-type calcium channels expressed in the thalamus are critically involved in the generation and modulation of sleep spindles which are prominent thalamocortical oscillations during NREM sleep. Sleep spindles are detected in the EEG as the sigma frequency band (11-15 Hz). Hence a decrease of power in the sigma frequency band in this trial is indicative the compound of formula (I)-mediated blockade of T-type calcium channels in the thalamocortical circuit.

Example 6: Modified Release Tablet Formulations 4 and 5 of the Compound of Formula (I)

Formulations 4 and 5 supplied as a coated matrix modified release (MR) tablets are designed to release approximately 80% of the drug substance within 7 hours. The compositions for the clinical batches of the product (formulations 4 and 5) are shown in Table 12. Each active tablet will contain the drug substance equivalent to 5 or 20 mg of the compound of formula (I), corresponding to about about 5.475 mg or 21.90 mg of the compound of formula (II), respectively.

TABLE 12

Formulation of the compound of formula (I) for modified release tablets containing 5 mg or 20 mg of the compound of formula (I)

| Ingredients | formulation 4 | formulation 5 |
|---|---|---|
| the compound of formula (II) (HCl salt, form C)[a] | 5.5 mg | 21.9 mg |
| Hypromellose | 58.0 mg | 58.0 mg |
| Microcrystalline cellulose[b] | 34.0 mg | 17.6 mg |
| Colloidal silicon dioxide | 1.5 mg | 1.5 mg |
| Magnesium stearate | 1.0 mg | 1.0 mg |
| Opadry white 03K580000 | 3.0 mg | 3.0 mg |
| Total weight | 103 mg | 103 mg |

[a]Quantity of formula (I) is adjusted for free base
[b]Quantity of Microcrystalline Cellulose (Avicel PH101) compensated accordingly for quantity of formula (I)

The dissolution method used to assess release is a chromatographic detection method using USP apparatus type-I. The dissolution parameters and high performance liquid chromatography (HPLC) conditions for assessing the release are shown below.

TABLE 13

Dissolution Parameters

| Dissolution media | 0.1N Hydrochloric acid |
|---|---|
| Media Volume | 900 mL |
| Rotation Speed | 100 RPM |
| Media Temperature | 37° C. ± 0.5° C. |
| Dissolution apparatus | USP type-I (Basket) |
| Sampling Volume | 10 mL |
| Replenishing Volume | 10 mL |
| Sampling | Manual, with 10 µm full flow PVDF in-line filter or Auto sampler with 10 µm full flow PVDF in-line filter followed by 0.45 µm nylon filter |

TABLE 14

Chromatographic conditions

| Column | Waters X-Bridge C18 (150 × 4.6 mm; 5 µm) |
|---|---|
| Mobile Phase-A | 25 mM potassium dihydrogen phosphate pH 3.0 |
| Mobile phase-B | Acetonitrile |
| Column temperature | 35° C. |
| Auto sampler temperature | Ambient |
| Injection volume | 50 µL |
| Flow rate | 1.5 mL/min |
| Detection | 230 nm |
| Diluent | Use dissolution media as diluent. |
| Run time | 8 minutes |
| Needle wash | Water:Methanol (20:80% v/v) |

TABLE 15

Gradient Program

| Time (Minutes) | Mobile Phase-A % | Mobile Phase-B % |
|---|---|---|
| 0.00 | 67 | 33 |
| 1.50 | 67 | 33 |
| 4.00 | 55 | 45 |
| 4.10 | 67 | 33 |
| 8.00 | 67 | 33 |

Manufacturing Process

The MR tablets are manufactured by sifting and blending of the excipients, including lubricant. The blend is granulated by roller compaction and milling of the ribbon compact. The granules are lubricated and then compressed into tablets. The tablets are then film coated.

A number of quality attributes are monitored in process, during release testing and on stability. These include hardness, friability, appearance, assay, related substances, content uniformity, water content and dissolution.

Additional formulations (formulations 6-9) are provided in Table 16.

TABLE 16

Formulation of the compound of formula (I) for modified release tablets containing 10, 15, 30, and 40 mg of the compound of formula (I)

| Ingredients | formulation 6 | formulation 7 | Formulation 8 | Formulation 9 |
|---|---|---|---|---|
| the compound of formula (II) (HCl salt, form C)[a] | 11.0 mg | 16.4 mg | 32.9 mg | 43.8 mg |
| Hypromellose | 58.0 mg | 58.0 mg | 87.0 mg | 116.0 mg |
| Microcrystalline cellulose[b] | 28.6 mg | 23.1 mg | 26.4 mg | 35.2 mg |
| Colloidal silicon dioxide | 1.5 mg | 1.5 mg | 2.3 mg | 3.0 mg |
| Magnesium stearate | 1.0 mg | 1.0 mg | 1.5 mg | 2.0 mg |
| Opadry white 03K580000 | 3.0 mg | 3.0 mg | 4.5 mg | 6.0 mg |
| Total weight | 103 mg | 103 mg | 155 mg | 206 mg |

[a]Quantity of formula (I) is adjusted for free base
[b]Quantity of Microcrystalline Cellulose (Avicel PH101) compensated accordingly for quantity of formula (I)

Figure 11:
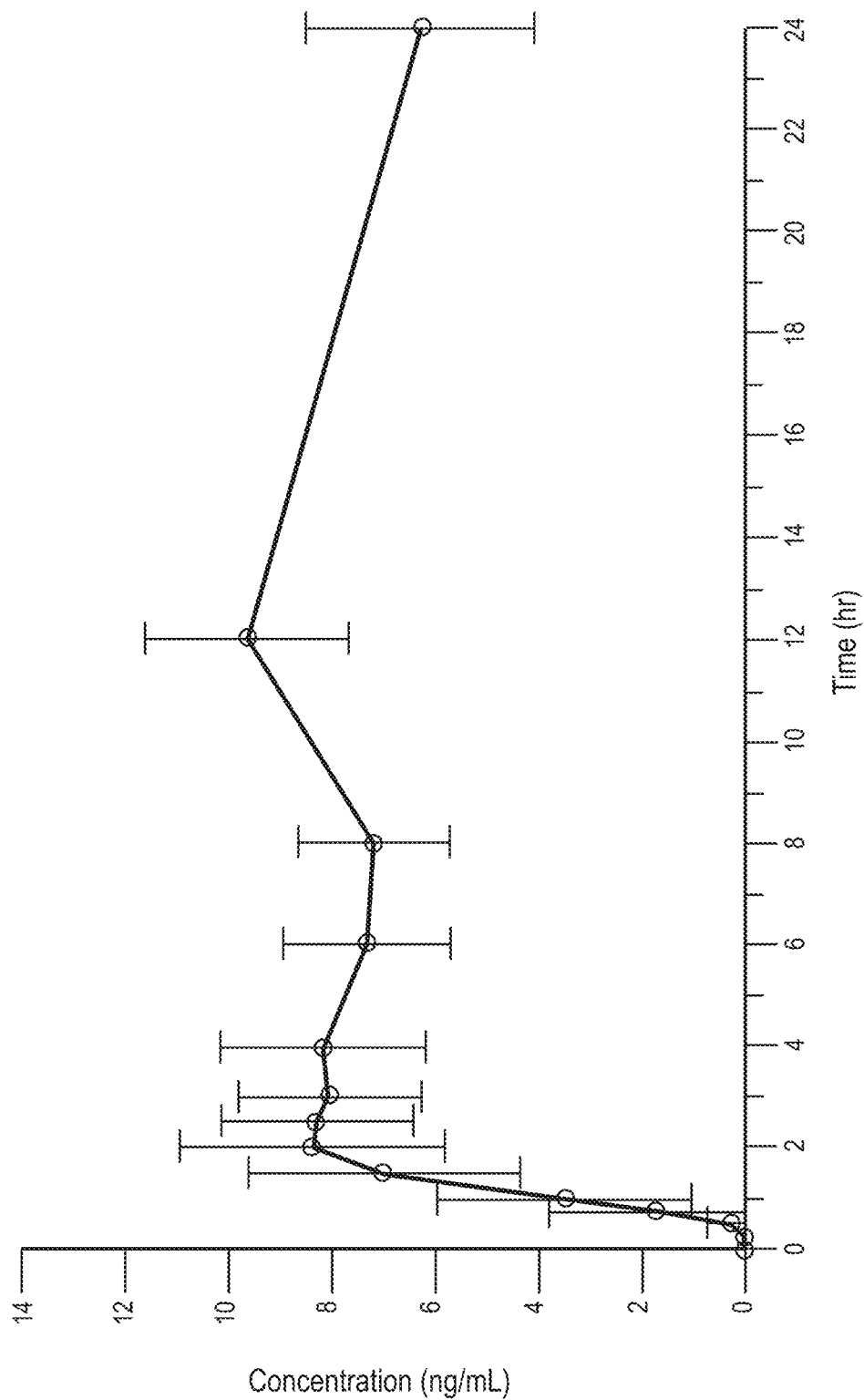
FIG. 11 shows mean (±SD) concentrations after a single oral doses of 5 mg tablet formulation 4.

After administration of a single 5 mg dose of the compound of formula (II) (formulation 4) to healthy volunteers, plasma concentrations of the free base of the compound of formula (I) (i.e., the compound of formula (II)) were quantifiable by 0.50 hours after administration of the modified release tablet formulation of the compound of formula (II). Plasma concentrations plateaued after reaching Cmax and then declined by 24 hours after administration of formulation 4. The compound of formula (I) as free base (i.e., a compound of formula (II)) remained quantifiable for the duration of the 24 hour sampling period after administration of a 5 mg dose of formulation 4. FIG. 11 shows mean (±SD) concentrations after a single oral doses of 5 mg tablet formulation 4.

TABLE 17

Geometric Mean Values (Geometric CV %) After a Single Oral Doses of 5 mg Tablet Formulation 4

| Parameter | 5 mg<br>[5 mg formulation 4 Tablet × 1]<br>(N = 8) |
|---|---|
| $t_{lag}$ (h)[1] | 0.500 (0.25-0.75) |
| $t_{max}$ (h)[1] | 12.00 (2.0-12.0) |
| $C_{max}$ (ng/mL) | 9.90 (23.3) |
| $AUC_{24}$ (ng*h/mL) | 179 (22.2) |

$AUC_{24}$ = area under the plasma concentration-time curve from time of dosing to 24 hours after dosing, $C_{max}$ = maximum (peak) plasma drug concentration, CV % = percent coefficient of variation, MR = modified-release, $t_{lag}$ = lag time, $t_{max}$ = time of maximum (peak) plasma drug concentration.
[1]Median (range).

Example 7: Long-Term Stability of the Compound of Formula (II) in the Formulation The drug product is chemically and physically stable for up to 48 months at 25° C./60% RH (Table 11) or for up to 6 months under accelerated conditions (40° C./75% RH) (Table 19). Based upon the currently available stability data, a shelf-life of 60 months has been assigned for the 20 mg drug product (formulation 3) packaged in 40 cc high-density polyethylene (HDPE) bottles when stored between 20° C. and 25° C. as per United States Pharmacopeia (USP) definition of controlled room temperature. Based on the excellent stability of the 20 mg drug product for at least 48 months and the essential identical composition of the 5 mg drug product, a shelf-life of 24 months has been assigned for the 5 mg drug product (formulation 4) packaged in 40 cc high-density polyethylene (HDPE) bottles when stored between 20° C. and 25° C.

Stability studies of MR tablets comprising the compound of formula II were performed at 25° C./60% RH. Batch size was 10,000 tablets. Each film coated tablet contained 20 mg of the compound of formula II. The tablets were packaged in 40 cc HDPE bottles containing 30 tablets with CRC cap (Table 19).

TABLE 19

Stability study data for MR tablets formulation 3 (containing 20 mg of the compound of formula (II)) at 25° C./60% over 48 months

| | Test | Specification | Initial | 1 M | 3 M | 6 M |
|---|---|---|---|---|---|---|
| 1 | Appearance | White to off white round shaped film coated tablets. | Complies | Complies | Complies | Complies |
| 2 | Assay by HPLC | 90.0-110.0% | 100.6% | 100.4% | 102.7% | 101.8% |
| 3 | | Related substances by HPLC (% w/w) | | | | |
| | Total impurities | NMT 1.5% | 0.38% | 0.37% | 0.40% | 0.38% |
| 4 | Water by KF | To be reported | 4.7% | 4.8% | 5.5% | 5.7% |

| | Test | Specification | 9 M | 12 M | 18 M | 24 M |
|---|---|---|---|---|---|---|
| 1 | Appearance | White to off white round shaped film coated tablets. | Complies | Complies | Complies | Complies |
| 2 | Assay by HPLC | 90.0-110.0% | 99.6% | 100.7% | 101.7% | 99.6% |
| 3 | | Related substances by HPLC (% w/w) | | | | |
| | Total impurities | NMT 1.5% | 0.40% | 0.40% | 0.41% | 0.45% |
| 4 | Water by KF | To be reported | 4.8% | 5.0% | 4.6% | 4.7% |

| | Test | Specification | 36 M | 48 M |
|---|---|---|---|---|
| 1 | Appearance | White to off white round shaped film coated tablets. | Complies | Complies |
| 2 | Assay by HPLC | 90.0-110.0% | 99.5% | 100.4% |
| 3 | | Related substances by HPLC (% w/w) | | |
| | Total impurities | NMT 1.5% | 0.42% | 0.72% |
| 4 | Water by KF | To be reported | 4.9% | 5.0% |

NMT-not more than;
RH-relative humidity

Stability studies of MR tablets comprising the compound of formula II were performed at 40° C./75% RH. Batch size was 10,000 tablets. Each film coated tablet contained 20 mg of the compound of formula II. The tablets were packaged in 40 cc HDPE bottles containing 30 tablets with CRC cap (Table 20).

TABLE 20

Stability study data for MR tablets formulation 3 (containing 20 mg of the compound of formula (II)) in accelerated conditions

| Test | Specification | Initial | 1 M | 3 M | 6 M |
|---|---|---|---|---|---|
| 1 Appearance | White to off white round shaped film coated tablets. | Complies | Complies | Complies | Complies |
| 2 Assay by HPLC | 90.0-110.0% | 100.6% | 99.5% | 100.2% | 101.0% |
| 3 | Related substances by HPLC (% w/w) | | | | |
| Total impurities | NMT 1.5% | 0.38% | 0.37% | 0.41% | 0.40% |
| 4 Water by KF | To be reported | 4.7% | 5.2% | 4.9% | 5.3% |

NMT-not more than;
RH-relative humidity

Stability studies of tablets of formulation 4 comprising the compound of formula (II) were performed at 25° C./60% RH. Batch size was 30,000 tablets. The tablets were packaged in 40 cc HDPE bottles containing 30 tablets with CRC cap (Table 21).

TABLE 21

Stability study data for tablets (formulation 4) at 25° C./60% RH over 3 months

| Test | Specification | Initial | 1M | 3M |
|---|---|---|---|---|
| 1 Appearance | White to off-white, round biconcave film-coated tablets, no embossing. | White, round biconcave film-coated tablets, no embossing | White, round biconcave film-coated tablets, no embossing. | White, round biconcave film-coated tablets, no embossing. |
| 2 Assay by HPLC | 90.0% to 110.0% of label claim | 97.9% | 98.9% | 96.1% |
| 3 | Related substances by HPLC (% w/w) | | | |
| Total impurities | Not more than 2.0% | 0.16% | 0.14% | 0.14% |
| 4 Water content USP <921> | To be reported | 4.3% | 4.4% | 4.4% |

Example 8: Assessment of the Safety, Tolerability, Pharmacokinetics, and Efficacy of Escalating Multiple Oral Doses in Adults with Generalized Epileptic Syndromes with Absence Seizures This open-label MAD trial will principally assess the safety and tolerability of 20 mg daily and 20 mg twice daily doses of the 20 mg tablet (formulation 3), adjunctive to standard of care. Secondary objectives include characterizing the PK, PD (sigma frequency power during NREM sleep) and effects on seizure frequency of the tablet (formulation 3).

Subjects

Subjects of this study are male or female between the ages of 18 and 60 years of age. Subjects have a clinical diagnosis of an epileptic syndrome (including, but not limited to, childhood absence seizures, juvenile absence seizures, juvenile myoclonic epilepsy, or Jeavons syndrome) with absence seizures consistent with the International League against Epilepsy Revised Classification of Seizures (2017), have absence seizures persisting despite documented trials with at least one standard anti-epileptic treatment, and have a history and electrographic evidence of absence epilepsy.

Methodology:

Each participant will complete 3 study periods: Screening, Treatment Period (up to 2 dose levels followed by a taper), and Safety Follow-up.

All participants will undergo two weeks of dosing of the compound of formula (II), followed by a taper:

Dose Level 1: 20 mg (formulation 3) every day for 7 days, and up to 14 days if 20 mg twice a day is not tolerated.

Dose Level 2: 20 mg (formulation 3) twice a day for 7 days.

Taper: If the participant tolerates the full 7 days of 20 mg twice a day, the taper will be 20 mg daily for 2 days (Day 15 and 16) followed by 20 mg every other day for 5 days (Day 17, 19, and 21). If the participant only tolerates 20 mg daily, the taper will be 20 mg every other day for 7 days (Day 15 to Day 21).

Safety and Tolerability

Safety variables include clinical laboratory evaluations, physical examination, vital signs, 12-lead ECG, the C-SSRS, and AE assessments, including event type, frequency, seriousness, severity, timing, and relationship to IP.

Pharmacokinetics

Pharmacokinetic parameters will include: maximum observed concentration (Cmax), and at steady-state (Cmax, SS), Time of Cmax (Tmax) and Cmax,SS (Tmax,SS), area under the concentration-time curve through the dosing interval (AUCtau or AUCSS), total clearance at steady-state (CLSS). Additional parameters such as half-life, accumulation and volume of distribution at steady-state (VSS) will be calculated if feasible.

Efficacy

Efficacy is evaluated by a) Number of seizures by participant reported seizure diary including absence seizures, generalized tonic-clonic seizures, and myoclonic seizures, b) EEG measures of seizure activity and pharmacodynamic effects of the compound of formula (I) including: Seizure Density (Number of bilateral synchronous symmetrical spike waves discharges of approximately 2.5-5 Hz>3 seconds in an approximately 24 hour period inclusive of seizures induced with photic stimulation and hyperventilation), Mean Seizure Duration (Average duration of 2.5-5 Hz discharges that are greater than 3 seconds in duration in a 24 hour period), Cumulative Seizure Duration (Product of Seizure Density and Mean Seizure Duration), Total time with 2.5-4 Hz spike wave discharges after hyperventilation and photic stimulation challenges, and c) Global severity as measured by CGI-S and CGI-I scores.

Example 9: Evaluation of Efficacy, Safety, Tolerability and Pharmacokinetics of the Compound of Formula (I) or a Pharmaceutically Acceptable Salt Thereof in Essential Tremor A randomised controlled trial is conducted to study the efficacy, safety, and tolerability of the compound of formula (I) in essential tremor. Each patient completes 3 study periods: Screening, Treatment period (21 or 28 days), and Safety follow-up.

Patients are males and females between the ages of 18 and 75 years old and have been diagnosed with essential tremor for at least 3 years. Patients receive a stable dose of 1 tremor medication throughout the clinical trial. Patients who had clinical evidence of psychogenic tremor, history of other medical, neurological or psychiatric condition that may explain or cause tremor, prior magnetic resonance-guided focused ultrasound or surgical intervention for essential tremor, botulinum toxin injection for essential tremor in the 6 months prior to Screening are excluded from the studies.

Patients receive 20 mg of the compound of formula (I) (formulation 3) orally once a day for 14 days and twice a day for 7 days (Part A) or 20 mg of the compound of formula (I) (formulation 3) orally once a day for 14 days and twice a day for 14 days or placebo (Part B).

Efficacy of the compound of formula (I) on upper limb tremor is assessed by The Essential Tremor Rating Assessment Scale (TETRAS) upper limb score at Baseline, on Day 21 (Part A) and Day 28 (Part B).

Efficacy of the compound of formula (I) on other measures of tremor severity is assessed by TETRAS performance subscale score and TETRAS performance individual items at Baseline, on Day 21 (Part A), and Day 28 (Part B).

Safety and tolerability of the compound of formula (I) is assessed through an integrated analysis of the following endpoints: patient and clinician-reported adverse events, vital signs, clinical laboratory results, electrocardiogram (ECG), and Columbia-Suicide Severity Rating Scale (C-SSRS) at Baseline, on Day 1, Day 7, Day 14, Day 21, and Day 28 (Part B only).

Example 10: Evaluation of Efficacy, Safety, Tolerability and Pharmacokinetics of the Compound of Formula (I) in Essential Tremor A clinical study was conducted to investigate the efficacy, safety, and tolerability of the compound of formula (I) in essential tremor. A patient who has been diagnosed with essential tremor completed 3 study periods: Screening, Treatment period (14 days), and Safety follow-up. The patient received a stable dose of 1 tremor medication throughout the clinical trial. The patient received 20 mg of the compound of formula (I) (one tablet of formulation 5) orally once a day for 7 days and 40 mg of the compound of formula (I) (two tablets of 20 mg formulation 5) orally once a day for 7 days (total of 14 days consecutively).

Efficacy of the compound of formula (I) on upper limb tremor was assessed by The Essential Tremor Rating Assessment Scale (TETRAS) upper limb score at Baseline, on Day 7, and on Day 14.

Efficacy of the compound of formula (I) on other measures of tremor severity was assessed by TETRAS performance subscale score, TETRAS performance individual items, and accelerometer at Baseline, on Day 7, and on Day 14.

Safety and tolerability of the compound of formula (I) were assessed through an integrated analysis of the following endpoints: patient and clinician-reported adverse events (e.g., dizziness or headache), vital signs, clinical laboratory results, electrocardiogram (ECG), and Columbia-Suicide Severity Rating Scale (C-SSRS) at Baseline, on Day 1, Day 7, Day 14, and Day 21.

Upper limb tremor score on the TETRAS was reduced as compared to baseline after administration of 20 mg (formulation 5) for 7 days (Day 7) and further reduction was seen after administering 40 mg (two tablets of 20 mg formulation 5) for an additional 7 days (Day 14). At Day 14, the upper limb tremor score was reduced by at least 25% as compared to the baseline. Notably, after 7 days of washout, the upper limb score increased as compared to that of Day 14 above, suggesting a gradual return to baseline dysfunction.

TETRAS performance score was reduced as compared to baseline after administration of 20 mg (formulation 5) for 7 days (Day 7) and further reduction was seen after administering 40 mg (two tablets of 20 mg formulation 5) for an additional 7 days (Day 14). At Day 14, the TETRAS performance score was reduced by at least 25% as compared to the baseline. Notably, after 7 days of washout, the performance score increased as compared to that of Day 14 above, suggesting a gradual return to baseline dysfunction.

Figure 6:
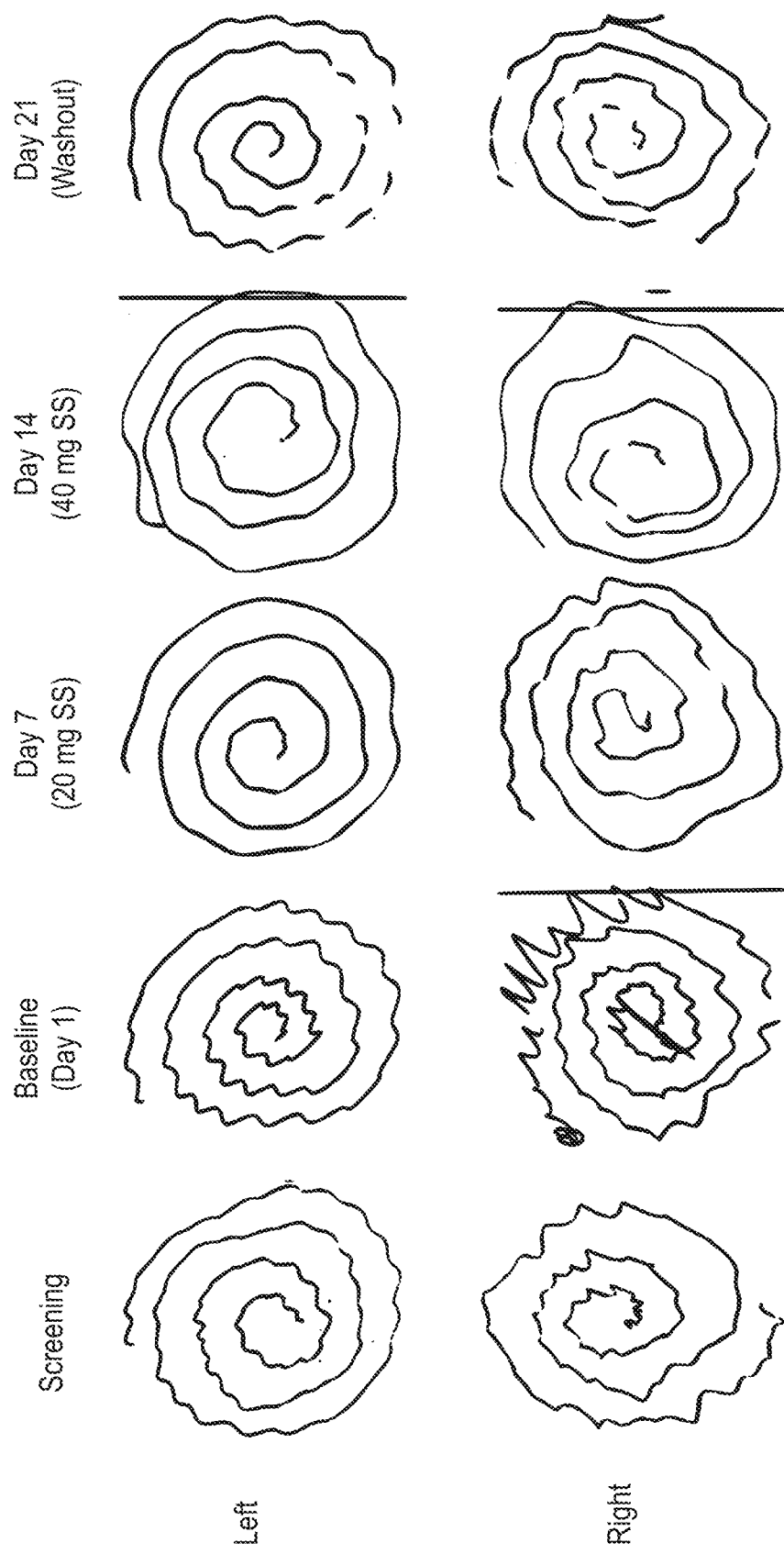
FIG. 6 shows the reduction in tremor in the Archimedes spiral task with administration of the compound of formula (II).

FIG. 6 demonstrates the reduction in tremor in the Archimedes spiral task with administration of the compound of formula (I) (formulation 5).

Kinesia ONE, an accelerometer and gyrsoscopic assessment of upper limb tremor was reduced as compared to baseline after administration of 20 mg for 7 days (Day 7) and further reduction was seen after administering 40 mg for an additional 7 days (Day 14). At Day 14, the tremor amplitude as measured by the accelerometer was reduced by at least 25% as compared to the baseline. Notably, after 7 days of washout, the tremor amplitude as measured by the accelerometer increased as compared to that of Day 14 above, suggesting a gradual return to baseline dysfunction.

The emerging data suggests that the compound of formula (I) is well tolerated and can reduce upper limb tremor amplitude and improve ADLs, such as writing skills. Physician rating scales, an accelerometer based tremor assessment tool, and patient symptom rating scales have all consistently demonstrated a reduction in symptoms with the compound of formula (I) (formulation 5) administration. In addition, participant anecdotes suggest that once lost abilities, like carrying a tray with food or drinks, can be regained after taking the compound of formula (I) (formulation 5).

A non-randomised, uncontrolled, and open-label trial is conducted to study the efficacy, safety, and tolerability of the compound of formula (I) in essential tremor. Each patient completes 3 study periods: Screening, Treatment period (14 days), and Safety follow-up. A video of the TETRAS Performance subscale is completed during Screening.

Patients are males and females between the ages of 18 and 75 years old and have been diagnosed with essential tremor. Patients receive a stable dose of 1 tremor medication throughout the clinical trial. Patients who had clinical evidence of psychogenic tremor, history of other medical, neurological or psychiatric condition that may explain or cause tremor, prior magnetic resonance-guided focused ultrasound or surgical intervention for essential tremor, botulinum toxin injection for essential tremor in the 6 months prior to Screening are excluded from the studies.

Patients receive 20 mg of the compound of formula (I) (formulation 5) orally once a day for 7 days and 40 mg of the compound of formula (I) (two tablets of 20 mg formulation 5) orally once a day for 7 days (total of 14 days consecutively).

Efficacy of the compound of formula (I) on upper limb tremor is assessed by The Essential Tremor Rating Assessment Scale (TETRAS) upper limb score at Baseline, on Day 7, and on Day 14.

Efficacy of the compound of formula (I) on other measures of tremor severity is assessed by TETRAS performance subscale score, TETRAS performance individual items, and accelerometer at Baseline, on Day 7, and on Day 14.

Efficacy of the compound of formula (I) may also be assessed by Clinical Global Impression (CGI), Clinical Global Impression-Severity (CGI-S), Clinical Global Impression-Improvement (CGI-I), and Patient Global Impression of Change (PGI-C).

Efficacy of the compound of formula (I) may also be assessed by any of the methods described herein.

Safety and tolerability of the compound of formula (I) is assessed through an integrated analysis of the following endpoints: patient and clinician-reported adverse events (e.g., dizziness or headache), vital signs, clinical laboratory results, electrocardiogram (ECG), and Columbia-Suicide Severity Rating Scale (C-SSRS) at Baseline, on Day 1, Day 7, Day 14, and Day 21.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:

1. A method of treating an essential tremor in a patient in need thereof, comprising administering to the patient a sufficient amount of an oral dosage form comprising a crystalline anhydrous Form C hydrochloride of Formula (II)

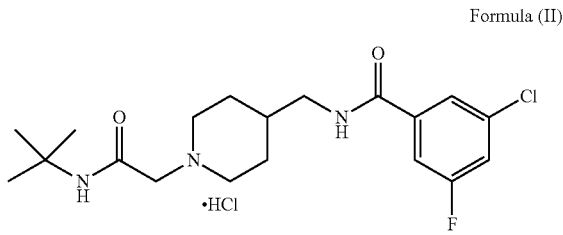 [SMILES: CC(C)(C)NC(=O)CN1CCC(CNC(=O)c2cc(F)cc(Cl)c2)CC1 ; Cl]

Formula (II)

and a modified-release polymer,
wherein the crystalline anhydrous Form C hydrochloride of Formula (II) is characterized by an X-ray powder diffraction (XRPD) pattern comprising one or more of the following peaks at the diffraction angle 2θ: 26.6±0.2, 16.2±0.2, 17.4±0.2, 22.6±0.2, and 11.5±0.2.

2. The method of claim 1, wherein the XRPD pattern comprises one or more of the following peaks at the diffraction angle 2θ: 26.6±0.2, 16.2±0.2, and 17.4±0.2.

3. The method of claim 1, wherein the XRPD pattern comprises a peak at the diffraction angle 2θ of 26.6±0.2.

4. The method of claim 3, wherein the XRPD pattern further comprises one or more of the following peaks at the diffraction angle 2θ: 16.2±0.2, 17.4±0.2, 22.6±0.2, and 11.5±0.2.

5. The method of claim 3, wherein the XRPD pattern further comprises peaks at the diffraction angle 2θ of 16.2±0.2 and 17.4±0.2.

6. The method of claim 5, wherein the XRPD pattern further comprises peaks at the diffraction angle 2θ of 22.6±0.2 and 11.5±0.2.

7. The method of claim 1, wherein the XRPD pattern further comprises one or more of the following peaks at the diffraction angle 2θ: 23.9±0.2, 18.3±0.2, 19.2±0.2, 18.5±0.2, and 20.0±0.2.

8. The method of claim 1, wherein the XRPD pattern comprises peaks at the diffraction angle 2θ of 26.6±0.2, 16.2±0.2, 17.4±0.2, 22.6±0.2, 11.5±0.2, 23.9±0.2, 18.3±0.2, 19.2±0.2, 18.5±0.2, and 20.0±0.2.

9. The method of claim 1, wherein the crystalline anhydrous Form C hydrochloride of Formula (II) has an XRPD pattern substantially as shown in FIG. 1.

10. The method of claim 1, wherein the crystalline anhydrous Form C hydrochloride of Formula (II) has a melting point onset at about 226.6° C. as determined by differential scanning calorimetry (DSC) having a heating rate of about 2° C./min.

11. The method of claim 1, wherein the crystalline anhydrous Form C hydrochloride of Formula (II) has a DSC profile substantially as shown in FIG. 2.

12. The method of claim 1, wherein the modified-release polymer is selected from the group consisting of a hydrophilic matrix polymer, a hydrophobic matrix polymer and a polyacrylate polymer.

13. The method of claim 12, wherein the modified-release polymer is a hydrophilic matrix polymer.

14. The method of claim 13, wherein the hydrophilic matrix polymer is hypromellose.

15. The method of claim 1, further comprising a diluent.

16. The method of claim 15, wherein the diluent is selected from the group consisting of a cellulose derivative, a starch, anhydrous lactose, lactose monohydrate, di-calcium phosphate (DCP), and a sugar alcohol.

17. The method of claim 16, wherein the diluent is a cellulose derivative.

18. The method of claim 17, wherein the cellulose derivative is microcrystalline cellulose.

19. The method of claim 16, wherein the diluent is a sugar alcohol.

20. The method of claim 19, wherein the sugar alcohol is selected from the group consisting of sorbitol, xylitol and mannitol.

21. The method of claim 20, wherein the diluent is mannitol.

22. The method of claim 1, further comprising a glidant.

23. The method of claim 22, wherein the glidant is selected from the group consisting of fumed silica, talc, and magnesium carbonate.

24. The method of claim 23, wherein the glidant is colloidal silicon dioxide.

25. The method of claim 1, further comprising a lubricant.

26. The method of claim 25, wherein the lubricant is selected from the group consisting of magnesium stearate, calcium stearate, stearic acid, talc, silica and fats.

27. The method of claim 26, wherein the lubricant is magnesium stearate.

28. The method of claim 1, comprising from about 0.9% to about 40% by weight of the crystalline anhydrous Form C hydrochloride.

29. The method of claim 1, wherein the method results in reduction of the essential tremor as assessed by The Essential Tremor Rating Assessment Scale (TETRAS) score.

30. The method of claim 1, wherein the method results in reduction of the essential tremor as assessed by The Essential Tremor Rating Assessment Scale (TETRAS) upper limb score.

31. The method of claim 1, wherein the method results in the reduction of the essential tremor as assessed by TETRAS-ADL (activities of daily living).

32. The method of claim 1, wherein the method results in the reduction of the essential tremor as assessed by TETRAS performance subscale score or TETRAS performance individual items.

33. The method of claim 1, wherein the method results in reduction of the essential tremor as assessed by accelerometer-based upper limb score.

34. The method of claim 1, wherein the method results in reduction of sigma frequency band.

35. The method of claim 1, wherein the essential tremor is upper limb tremor.

* * * * *